(12) United States Patent
Heike et al.

(10) Patent No.: US 8,883,498 B2
(45) Date of Patent: Nov. 11, 2014

(54) METHOD FOR INDUCING DIFFERENTIATION OF PLURIPOTENT STEM CELLS INTO SKELETAL MUSCLE OR SKELETAL MUSCLE PROGENITOR CELLS

(75) Inventors: Toshio Heike, Kyoto (JP); Tatsutoshi Nakahata, Kyoto (JP); Tomonari Awaya, Kyoto (JP)

(73) Assignee: Kyoto University, Kyoto-shi (JP)

( * ) Notice: Subject to any disclaimer, the term of this patent is extended or adjusted under 35 U.S.C. 154(b) by 13 days.

(21) Appl. No.: 13/642,650

(22) PCT Filed: Apr. 21, 2011

(86) PCT No.: PCT/JP2011/060340
§ 371 (c)(1),
(2), (4) Date: Oct. 22, 2012

(87) PCT Pub. No.: WO2011/132799
PCT Pub. Date: Oct. 27, 2011

(65) Prior Publication Data
US 2013/0040387 A1 Feb. 14, 2013

Related U.S. Application Data

(60) Provisional application No. 61/326,929, filed on Apr. 22, 2010.

(51) Int. Cl.
*C12N 5/00* (2006.01)
*C12N 5/077* (2010.01)
*A61K 35/12* (2006.01)

(52) U.S. Cl.
CPC .............. *C12N 5/0658* (2013.01); *A61K 35/12* (2013.01); *C12N 2506/45* (2013.01); *C12N 2506/02* (2013.01)
USPC ........................................................ 435/325

(58) Field of Classification Search
USPC ........................................................ 435/325
See application file for complete search history.

(56) References Cited

U.S. PATENT DOCUMENTS

2007/0238175 A1* 10/2007 Chi .............................. 435/378

OTHER PUBLICATIONS

Barberi, T., Willis, L.M., Socci, N.D., Studer, L., "Derivation of Multipotent Mesenchymal Precursors from Human Embryonic Stem Cells", PLoS Medicine 2005, vol. 2, Issue 6, pp. 0554-0560.*

Zheng, J.K., et al., "Skeletal myogenesis by human embryonic stem cells," Cell Research, vol. 16, No. 8, pp. 713 to 722, (Aug. 2006).

Barberi, T., et al., "Derivation of engraftable skeletal myoblasts from human embryonic stem cells," Nature Medicine, vol. 13, No. 5, pp. 642 to 648, (May 2007).

Chang, H., et al., "Generation of transplantable, functional satellite-like cells from mouse embryonic stem cells," The FASEB Journal, vol. 23, No. 6, pp. 1907 to 1919, (2009).

Mizuno, Y., "Production of transplantable skeletal muscle progenitor cells from mouse iPS cells," Regenerative Medicine, vol. 8 Suppl., Total 3 Pages, (2009) (with English translation).

Mizuno, Y., "The differentiation tendencey from embryonic stem cells to skeletal myocytes is different depending on the passage number," Journal of japanese Physical Therapy Association, Physical Therapy of Japan, vol. 35, No. Suppl. 2, Total 4 Pages, (Apr. 20, 2008) (with English translation).

International Search Report Issued Aug. 23, 2011 in PCT/JP11/60340 Filed Apr. 21, 2011.

Barberi, T., et al., "Derivation of engraftable skeletal myoblasts from human embryonic stem cells," vol. 13, No. 5, pp. 642 to 648, (May 2007).

* cited by examiner

*Primary Examiner* — Marcia S Noble
*Assistant Examiner* — Magdalene Sgagias
(74) *Attorney, Agent, or Firm* — Oblon, Spivak, McClelland, Maier & Neustadt, L.L.P.

(57) ABSTRACT

A method for inducing the differentiation of pluripotent stem cells into skeletal muscle or skeletal muscle progenitor cells is provided. Specifically, a method for producing artificial skeletal muscle or skeletal muscle progenitor cells from human pluripotent stem cells is provided, comprising the following steps of: (1) culturing human pluripotent stem cells by suspension culture; (2) culturing a cell population after suspension culture by adhesion culture; (3) dissociating cells after adhesion culture; and (4) culturing the dissociated cells by adhesion culture. Artificial skeletal muscle or induced skeletal muscle progenitor cells prepared by the method are also provided.

13 Claims, 4 Drawing Sheets

SEQUENCE LISTING

```
<160> NUMBER OF SEQ ID NOS: 21

<210> SEQ ID NO 1
<211> LENGTH: 3518
<212> TYPE: DNA
<213> ORGANISM: Mus musculus
<220> FEATURE:
<221> NAME/KEY: CDS
<222> LOCATION: (425)..(1528)

<400> SEQUENCE: 1
cccgagccgg cggggagccg ctccgctcca ggtggcgggc ggcgggagcg aggtgaggct      60
gcgggtggcc cgggcagggg tccccagggg actggcgggc tgcaaggctg cagactgcct     120
tcgagacagc gcgcccccgc ccggccctgc tgtgccccccg gagctgagct ccgggcggtg     180
ctggcaaagt ttgctttgaa ctcgctcccc tcagcctggt cggcccgttg cgagctgccc     240
tgagcgagct gaccccaggc caggcttccc aggagcaggg accagggcgc gggctgcaag     300
ctggtgggcc tggggagaga ccagagcccc gcagccagct gcagcgaggg actcggagcc     360
gcctcttccc tcggcgggca ccgcagtcag ctcgtctccc ccttccctcc cgcagggagc     420
```

```
ggac atg gac ttc gac tcg tat cag cac tat ttc tac gac tat gac tgc    469
     Met Asp Phe Asp Ser Tyr Gln His Tyr Phe Tyr Asp Tyr Asp Cys
     1               5                   10                  15 gga gag gat ttc tac cgc tcc acg gcg ccc agc gag gac atc tgg aag    517
Gly Glu Asp Phe Tyr Arg Ser Thr Ala Pro Ser Glu Asp Ile Trp Lys
                20                  25                  30 aaa ttc gag ctg gtg ccg tcg ccc ccc acg tcg ccg ccc tgg ggc tcc    565
Lys Phe Glu Leu Val Pro Ser Pro Pro Thr Ser Pro Pro Trp Gly Ser
            35                  40                  45 ggt ccc ggc gcc gtg gac cca gcc tct ggg att aat ccc ggg gag ccg    613
Gly Pro Gly Ala Val Asp Pro Ala Ser Gly Ile Asn Pro Gly Glu Pro
        50                  55                  60 tgg cct gga ggg ggt gcc ggg gac gag gcg gaa tct cgg ggc cat tcg    661
Trp Pro Gly Gly Gly Ala Gly Asp Glu Ala Glu Ser Arg Gly His Ser
    65                  70                  75 aaa gcc tgg ggc agg aat tat gct tcc atc att cgc cgt gac tgc atg    709
Lys Ala Trp Gly Arg Asn Tyr Ala Ser Ile Ile Arg Arg Asp Cys Met
80              85                  90                  95 tgg agc ggc ttc tcc gcc cga gaa cgg ctg gag aga gtg gtg agc gac    757
Trp Ser Gly Phe Ser Ala Arg Glu Arg Leu Glu Arg Val Val Ser Asp
                100                 105                 110 agg ctg gcc cca ggc gcg ccc cgg ggg aac ccg ccc aaa gcg ccc gct    805
Arg Leu Ala Pro Gly Ala Pro Arg Gly Asn Pro Pro Lys Ala Pro Ala
            115                 120                 125 acc ccg gac ggc act cct agt ctg gaa gcc agt aac ccg gcg ccc gcc    853
Thr Pro Asp Gly Thr Pro Ser Leu Glu Ala Ser Asn Pro Ala Pro Ala
        130                 135                 140 acc caa tgt cag ctg ggc gag ccc aag act cag gcc tgc tcc ggg tcc    901
Thr Gln Cys Gln Leu Gly Glu Pro Lys Thr Gln Ala Cys Ser Gly Ser
    145                 150                 155 gag agc ccc agc gat tct gaa ggt gaa gag att gac gtg gtg acc gtg    949
Glu Ser Pro Ser Asp Ser Glu Gly Glu Glu Ile Asp Val Val Thr Val
160                 165                 170                 175 gag aag agg cga tct ctg gac atc cga aag cca gtc acc atc acg gtg    997
Glu Lys Arg Arg Ser Leu Asp Ile Arg Lys Pro Val Thr Ile Thr Val
                180                 185                 190 cga gca gac ccc ctg gac ccc tgc atg aag cac ttc cat atc tct atc    1045
Arg Ala Asp Pro Leu Asp Pro Cys Met Lys His Phe His Ile Ser Ile
            195                 200                 205 cac caa cag cag cat aac tat gct gcc cgt ttt cct cca gaa agt tgc    1093
His Gln Gln Gln His Asn Tyr Ala Ala Arg Phe Pro Pro Glu Ser Cys
        210                 215                 220 tct caa gag ggg gat cct gag cca ggt ccc cag gaa gag gct ccg gag    1141
Ser Gln Glu Gly Asp Pro Glu Pro Gly Pro Gln Glu Glu Ala Pro Glu
    225                 230                 235 ata gaa gct ccc aag gag aaa gag gag gag gaa gag gaa gag gag gaa    1189
Ile Glu Ala Pro Lys Glu Lys Glu Glu Glu Glu Glu Glu Glu Glu Glu
240                 245                 250                 255 gaa gag att gtg agc ccc cca cct gtc gga agt gag gct ccc cag tcc    1237
Glu Glu Ile Val Ser Pro Pro Pro Val Gly Ser Glu Ala Pro Gln Ser
                260                 265                 270 tgc cac ccc aaa cct gtc agt tct gac act gag gac gtg acc aag agg    1285
Cys His Pro Lys Pro Val Ser Ser Asp Thr Glu Asp Val Thr Lys Arg
            275                 280                 285 aag aac cat aac ttc ttg gaa cga aaa agg agg aat gac ctc cgc tcc    1333
Lys Asn His Asn Phe Leu Glu Arg Lys Arg Arg Asn Asp Leu Arg Ser
        290                 295                 300 cgg ttc cta gcc ctg cgg gac cag gtt ccc acc ctg gcc agc tgc tct    1381
Arg Phe Leu Ala Leu Arg Asp Gln Val Pro Thr Leu Ala Ser Cys Ser
```

|  |  |
|---|---|
| 305 310 315 | |
| aag gcc ccc aaa gtc gtg atc ctc agc aag gcg tta gaa tac ttg cag<br>Lys Ala Pro Lys Val Val Ile Leu Ser Lys Ala Leu Glu Tyr Leu Gln<br>320 325 330 335 | 1429 |
| gct ttg gtg ggg gct gaa aag aaa atg gct aca gag aaa agg cag ctc<br>Ala Leu Val Gly Ala Glu Lys Lys Met Ala Thr Glu Lys Arg Gln Leu<br>340 345 350 | 1477 |
| cgg tgt cgg caa cag caa ctg caa aag aga atc gcg tac ctc agt ggc<br>Arg Cys Arg Gln Gln Gln Leu Gln Lys Arg Ile Ala Tyr Leu Ser Gly<br>355 360 365 | 1525 |
| tac taaccgacca gaacgcctga cttcttggtc tcacagacac aagcttattg<br>Tyr | 1578 |
| tttaacctct ctctcccttt tagtaatttg cacattttgg ttacagcggg ggggcagtc | 1638 |
| tggacagtag atcccagaat gcattgcagc cggtgtgcgc acacaataag ggcttgcatt | 1698 |
| cttggtaacc tcgaaaccca attctccctc ttccccgacc gactcatggg aatgctgtcc | 1758 |
| ttctctggcg cctttggctt ctcagcaggc agctactgag gagatttggg gtctgcttag | 1818 |
| ctcactagct cctgacgaaa ggctgacaga tgctatgcaa caggtggtgg acgttgttgg | 1878 |
| ggctgcagcc tacgtgaaat ctcacactgt gctggggctt caggctagga aaggatgctg | 1938 |
| ctctcactgc tgtctctggg gatgatctga ggacagctgg gcctggatac tgtcccccag | 1998 |
| gctccgtttt ccaggaggca agcgagctgt cccgggcgaa gacaagctcg cagacttgat | 2058 |
| cagcatggag cattacctca ccgtcagaca ctttacagta gctgtggagt ggaaaccttt | 2118 |
| aagatagatt tggatggtag gccacaccct tccctgcacg ctcaatgcta tgactttgag | 2178 |
| aaagggcttg gcctctatgt agagtctttg tctcagagtt ctctgggcct tctcagagag | 2238 |
| ggacctttct atcctcacaa gggccttttt tgtttcttcc tgcctttgtt atgcaatggc | 2298 |
| caccacagca ccctttcaca ccgaccagaa atatttcccc aggacatagg gaatgggtc | 2358 |
| acagcccagg acctggggaa gccttggcat ccccactcat gaccaacggt ccttgcccag | 2418 |
| gttttctgca gggctatttg aggcccagct tggaaccttt tctcgaggca gatagttaca | 2478 |
| aggtgcctct gaaggacaag ccctatcgct tcctctttcc cacctgcctc tctgtcagat | 2538 |
| cttgactctg tctacaatct gctggaacag tgcaaacctg tccttctcga gcaactttgc | 2598 |
| tggctctgca gccaccatcc tgattctctg ccggcctgag tcatatcctt tcccctggaa | 2658 |
| tctgggcctt acagagagat tcagggggc accgcttgca ttcacctgat gcccccagaa | 2718 |
| ggtaaactta cttcctggtg ggttgtcagt gtacctctag gaacgctact cagccaacaa | 2778 |
| ggagagtttg ctccagctgt gttctgcaac tccctgtgga atcaaagtac agccctctat | 2838 |
| cctgggaaag tcaccaagct agcagccgtc acgtgagcat ctttcaggag atcctaagct | 2898 |
| ttgcctgaaa gaagagccag cctttccaga actctaccca ggaaagcaga tctgttcctg | 2958 |
| ctggccctgg gcttggaagt aggggtacag tgtgggggac agacagtaag taacaacatg | 3018 |
| tggctctcaa aaaccagcta ccacttccaa attggctccc aactgtgatg gcctccaatt | 3078 |
| acttcctggc ctcaagtcct agaggaagct tcggaagttg ctgttgtacc tgttggggca | 3138 |
| ggacttctag gcaccaaggg actcctggaa ctatcttggg aggacaagtg gtgaacaggc | 3198 |
| taaagtctca tctgaatggc ttgtgtttta aagctgctg cggggttgta tgctgtgggc | 3258 |
| gtcttttgtt tttgtttttg cttttttttt taatactgta ttttgtatg cttttttgca | 3318 |
| aagtggtgtt aactgttttt gtataagaaa acaaaaaac aaaaaccctc ctgttgcaag | 3378 |
| ggtctggttt attttgaaag gtgcatttac ctgaaatttt gtatttagtt gtaatcatta | 3438 |

```
attgcttgat tttaaactgt tgccttctgg gacatcttct aataaaaaga tttctcaaaa    3498
aaaaaaaaaa aaaaaaaaaa                                                3518
```

<210> SEQ ID NO 2
<211> LENGTH: 368
<212> TYPE: PRT
<213> ORGANISM: Mus musculus

<400> SEQUENCE: 2

```
Met Asp Phe Asp Ser Tyr Gln His Tyr Phe Tyr Asp Tyr Asp Cys Gly
1               5                  10                  15

Glu Asp Phe Tyr Arg Ser Thr Ala Pro Ser Glu Asp Ile Trp Lys Lys
            20                  25                  30

Phe Glu Leu Val Pro Ser Pro Thr Ser Pro Pro Trp Gly Ser Gly
        35                  40                  45

Pro Gly Ala Val Asp Pro Ala Ser Gly Ile Asn Pro Gly Glu Pro Trp
    50                  55                  60

Pro Gly Gly Gly Ala Gly Asp Glu Ala Glu Ser Arg Gly His Ser Lys
65                  70                  75                  80

Ala Trp Gly Arg Asn Tyr Ala Ser Ile Ile Arg Arg Asp Cys Met Trp
                85                  90                  95

Ser Gly Phe Ser Ala Arg Glu Arg Leu Glu Arg Val Val Ser Asp Arg
            100                 105                 110

Leu Ala Pro Gly Ala Pro Arg Gly Asn Pro Lys Ala Pro Ala Thr
        115                 120                 125

Pro Asp Gly Thr Pro Ser Leu Glu Ala Ser Asn Pro Ala Pro Ala Thr
    130                 135                 140

Gln Cys Gln Leu Gly Glu Pro Lys Thr Gln Ala Cys Ser Gly Ser Glu
145                 150                 155                 160

Ser Pro Ser Asp Ser Glu Gly Glu Glu Ile Asp Val Val Thr Val Glu
                165                 170                 175

Lys Arg Arg Ser Leu Asp Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Gly Asp Pro Glu Pro Gly Pro Gln Glu Glu Ala Pro Glu Ile
225                 230                 235                 240

Glu Ala Pro Lys Glu Lys Glu Glu Glu Glu Glu Glu Glu Glu
                245                 250                 255

Glu Ile Val Ser Pro Pro Val Gly Ser Glu Ala Pro Gln Ser Cys
            260                 265                 270

His Pro Lys Pro Val Ser Ser Asp Thr Glu Asp Val Thr Lys Arg Lys
        275                 280                 285

Asn His Asn Phe Leu Glu Arg Lys Arg Arg Asn Asp Leu Arg Ser Arg
    290                 295                 300

Phe Leu Ala Leu Arg Asp Gln Val Pro Thr Leu Ala Ser Cys Ser Lys
305                 310                 315                 320

Ala Pro Lys Val Val Ile Leu Ser Lys Ala Leu Glu Tyr Leu Gln Ala
                325                 330                 335

Leu Val Gly Ala Glu Lys Lys Met Ala Thr Glu Lys Arg Gln Leu Arg
            340                 345                 350

Cys Arg Gln Gln Gln Leu Gln Lys Arg Ile Ala Tyr Leu Ser Gly Tyr
```

<210> SEQ ID NO 3
<211> LENGTH: 3624
<212> TYPE: DNA
<213> ORGANISM: Homo sapiens
<220> FEATURE:
<221> NAME/KEY: CDS
<222> LOCATION: (582)..(1673)

<400> SEQUENCE: 3

```
aatgcgcctg cagctcgcgc tcccgcgccg atcccgagag cgtccgggcc gccgtgcgcg    60
agcgagggag ggcgcgcgcg cggggggggc gcgcttgtga gtgcgggccg cgctctcggc   120
ggcgcgcatg tgcgtgtgtg ctggctgccg ggctgccccg agccggcggg gagccggtcc   180
gctccaggtg gcgggcggct ggagcgaggt gaggctgcgg gtggccaggg cacgggcgcg   240
ggtcccgcgg tgcgggctgg ctgcaggctg ccttctgggc acgcgcgcc  cccgcccggc   300 cccgccgggc cctgggagct cgctccgggg cggcgctggc aaagtttgct ttgaactcgc   360
tgcccacagt cgggtccgcg cgctgcgatt ggcttcccct accactctga cccggggccc   420
ggcttcccgg gacgcgagga ctgggcgcag gctgcaagct ggtggggttg gggaggaacg   480
agagcccggc agccgactgt gccgagggac ccggggacac ctccttcgcc cggccggcac   540
ccggtcagca cgtcccccct tccctcccgc agggagcgga c atg gac tac gac tcg   596
                                              Met Asp Tyr Asp Ser
                                                1               5
```

| | | | | |
|---|---|---|---|---|
| tac cag cac tat ttc tac gac tat gac tgc ggg gag gat ttc tac cgc | 644 |
| Tyr Gln His Tyr Phe Tyr Asp Tyr Asp Cys Gly Glu Asp Phe Tyr Arg | |
| 10                  15                  20 | |
| tcc acg gcg ccc agc gag gac atc tgg aag aaa ttc gag ctg gtg cca | 692 |
| Ser Thr Ala Pro Ser Glu Asp Ile Trp Lys Lys Phe Glu Leu Val Pro | |
| 25                  30                  35 | |
| tcg ccc ccc acg tcg ccg ccc tgg ggc ttg ggt ccc ggc gca ggg gac | 740 |
| Ser Pro Pro Thr Ser Pro Pro Trp Gly Leu Gly Pro Gly Ala Gly Asp | |
| 40                  45                  50 | |
| ccg gcc ccc ggg att ggt ccc ccg gag ccg tgg ccc gga ggg tgc acc | 788 |
| Pro Ala Pro Gly Ile Gly Pro Pro Glu Pro Trp Pro Gly Gly Cys Thr | |
| 55                  60                  65 | |
| gga gac gaa gcg gaa tcc cgg ggc cac tcg aaa ggc tgg ggc agg aac | 836 |
| Gly Asp Glu Ala Glu Ser Arg Gly His Ser Lys Gly Trp Gly Arg Asn | |
| 70                  75                  80                  85 | |
| tac gcc tcc atc ata cgc cgt gac tgc atg tgg agc ggc ttc tcg gcc | 884 |
| Tyr Ala Ser Ile Ile Arg Arg Asp Cys Met Trp Ser Gly Phe Ser Ala | |
| 90                  95                  100 | |
| cgg gaa cgg ctg gag aga gct gtg agc gac cgg ctc gct cct ggc gcg | 932 |
| Arg Glu Arg Leu Glu Arg Ala Val Ser Asp Arg Leu Ala Pro Gly Ala | |
| 105                 110                 115 | |
| ccc cgg ggg aac ccg ccc aag gcg tcc gcc gcc ccg gac tgc act ccc | 980 |
| Pro Arg Gly Asn Pro Pro Lys Ala Ser Ala Ala Pro Asp Cys Thr Pro | |
| 120                 125                 130 | |
| agc ctc gaa gcc ggc aac ccg gcg ccc gcc gcc ccc tgt ccg ctg ggc | 1028 |
| Ser Leu Glu Ala Gly Asn Pro Ala Pro Ala Ala Pro Cys Pro Leu Gly | |
| 135                 140                 145 | |
| gaa ccc aag acc cag gcc tgc tcc ggg tcc gag agc cca agc gac tcg | 1076 |
| Glu Pro Lys Thr Gln Ala Cys Ser Gly Ser Glu Ser Pro Ser Asp Ser | |
| 150                 155                 160                 165 | |
| gag aat gaa gaa att gat gtt gtg aca gta gag aag agg cag tct ctg | 1124 |
| Glu Asn Glu Glu Ile Asp Val Val Thr Val Glu Lys Arg Gln Ser Leu | |
| 170                 175                 180 | |

```
ggt att cgg aag ccg gtc acc atc acg gtg cga gca gac ccc ctg gat    1172
Gly Ile Arg Lys Pro Val Thr Ile Thr Val Arg Ala Asp Pro Leu Asp
            185                 190                 195 ccc tgc atg aag cat ttc cac atc tcc atc cat cag caa cag cac aac    1220
Pro Cys Met Lys His Phe His Ile Ser Ile His Gln Gln Gln His Asn
        200                 205                 210 tat gct gcc cgt ttt cct cca gaa agc tgc tcc caa gaa gag gct tca    1268
Tyr Ala Ala Arg Phe Pro Pro Glu Ser Cys Ser Gln Glu Glu Ala Ser
    215                 220                 225 gag agg ggt ccc caa gaa gag gtt ctg gag aga gat gct gca ggg gaa    1316
Glu Arg Gly Pro Gln Glu Glu Val Leu Glu Arg Asp Ala Ala Gly Glu
230                 235                 240                 245 aag gaa gat gag gag gat gaa gag att gtg agt ccc cca cct gta gaa    1364
Lys Glu Asp Glu Glu Asp Glu Glu Ile Val Ser Pro Pro Pro Val Glu
                250                 255                 260 agt gag gct gcc cag tcc tgc cac ccc aaa cct gtc agt tct gat act    1412
Ser Glu Ala Ala Gln Ser Cys His Pro Lys Pro Val Ser Ser Asp Thr
            265                 270                 275 gag gat gtg acc aag agg aag aat cac aac ttc ctg gag cgc aag agg    1460
Glu Asp Val Thr Lys Arg Lys Asn His Asn Phe Leu Glu Arg Lys Arg
        280                 285                 290 cgg aat gac ctg cgt tcg cga ttc ttg gcg ctg agg gac cag gtg ccc    1508
Arg Asn Asp Leu Arg Ser Arg Phe Leu Ala Leu Arg Asp Gln Val Pro
    295                 300                 305 acc ctg gcc agc tgc tcc aag gcc ccc aaa gta gtg atc cta agc aag    1556
Thr Leu Ala Ser Cys Ser Lys Ala Pro Lys Val Val Ile Leu Ser Lys
310                 315                 320                 325 gcc ttg gaa tac ttg caa gcc ctg gtg ggg gct gag aag agg atg gct    1604
Ala Leu Glu Tyr Leu Gln Ala Leu Val Gly Ala Glu Lys Arg Met Ala
                330                 335                 340 aca gag aaa aga cag ctc cga tgc cgg cag cag cag ttg cag aaa aga    1652
Thr Glu Lys Arg Gln Leu Arg Cys Arg Gln Gln Gln Leu Gln Lys Arg
            345                 350                 355 att gca tac ctc act ggc tac taactgacca aaaagcctga cagttctgtc       1703
Ile Ala Tyr Leu Thr Gly Tyr
            360 ttacgaagac acaagtttat tttttaacct ccctctcccc tttagtaatt tgcacatttt  1763 ggttatggtg ggacagtctg gacagtagat cccagaatgc attgcagccg gtgcacacac  1823 aataaaggct tgcattcttg gaaaccttga aacccagctc tccctcttcc ctgactcatg  1883 ggagtgctgt atgttctctg gcgccttggg cttcccagca ggcagctgac tgaggagcct  1943 tggggtctgc ctagctcact agctctgaag aaaaggctga cagatgctat gcaacaggtg  2003 gtggatgttg tcaggggctc cagcctgcat gaaatctcac actctgcatg agctttaggc  2063 taggaaagga tgctcccaac tggtgtctct ggggtgatgc aaggacagct gggcctggat  2123 gctctccctg aggctccttt ttccagaaga cacacgagct gtcttgggtg aagacaagct  2183 tgcagacttg atcaacattg accattacct cactgtcaga cactttacag tagccaagga  2243 gttggaaacc tttatatatt atgatgttag ctgaccccct tcctcccact cccaatgctg  2303 cgaccctggg aacacttaaa aagcttggcc tctagattct ttgtctcaga gccctctggg  2363 ctctctcctc tgagggaggg accttctctt cctcacaagg gactttttg ttccattatg   2423 ccttgttatg caatgggctc tacagcaccc tttcccacag gtcagaaata tttccccaag  2483 acacagggaa atcggtccta gcctggggcc tggggatagc ttggagtcct ggcccatgaa  2543 cttgatccct gcccaggtgt tttccgaggg gcacttgagg cccagtcttt tctcaaggca  2603 ggtgtaagac acctcagagg gagaactgta ctgctgcctc tttcccacct gcctcatctc  2663
```

-continued

```
aatccttgag cggcaagttt gaagttcttc tggaaccatg caaatctgtc ctcctcatgc    2723
aattccaagg agcttgctgg ctctgcagcc acccttgggc ccttccagc ctgccatgaa     2783 tcagatatct ttcccagaat ctgggcgttt ctgaagtttt ggggagagct gttgggactc    2843
atccagtgct ccagaaggtg gacttgcttc tggtgggttt taaaggagcc tccaggagat    2903
atgcttagcc aaccatgatg gattttaccc cagctggact cggcagctcc aagtggaatc    2963
cacgtgcagc ttctagtctg ggaaagtcac ccaacctagc agttgtcatg tgggtaacct    3023
caggcacctc taagcctgtc ctggaagaag gaccagcagc ccctccagaa ctctgcccag    3083
gacagcaggt gcctgctggc tctgggtttg aagttgggg tgggtagggg gtggtaagta     3143
ctatatatgg ctctggaaaa ccagctgcta cttccaaatc tattgtccat aatggtttct    3203
ttctgaggtt gcttcttggc ctcagaggac cccaggggat gtttggaaat agcctctcta    3263
cccttctgga gcatggttta caaaagccag ctgacttctg gaattgtcta tggaggacag    3323
tttgggtgta ggttactgat gtctcaactg aatagcttgt gttttataag ctgctgttgg    3383
ctattatgct gggggagtct tttttttta tattgtattt ttgtatgcct tttgcaaagt     3443
ggtgttaact gttttgtac aaggaaaaaa actcttgggg caatttcctg ttgcaagggt     3503
ctgatttatt ttgaaaggca agttcacctg aaattttgta tttagttgtg attactgatt    3563
gcctgatttt aaaatgttgc cttctgggac atcttctaat aaaagatttc tcaaacatgt    3623
c                                                                    3624
```

<210> SEQ ID NO 4
<211> LENGTH: 364
<212> TYPE: PRT
<213> ORGANISM: Homo sapiens
<400> SEQUENCE: 4

```
Met Asp Tyr Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Thr Ser Pro Pro Trp Gly Leu Gly
        35                  40                  45

Pro Gly Ala Gly Asp Pro Ala Pro Gly Ile Gly Pro Glu Pro Trp
    50                  55                  60

Pro Gly Gly Cys Thr Gly Asp Glu Ala Glu Ser Arg Gly His Ser Lys
65                  70                  75                  80

Gly Trp Gly Arg Asn Tyr Ala Ser Ile Ile Arg Arg Asp Cys Met Trp
                85                  90                  95

Ser Gly Phe Ser Ala Arg Glu Arg Leu Glu Arg Ala Val Ser Asp Arg
            100                 105                 110

Leu Ala Pro Gly Ala Pro Arg Gly Asn Pro Pro Lys Ala Ser Ala Ala
        115                 120                 125

Pro Asp Cys Thr Pro Ser Leu Glu Ala Gly Asn Pro Ala Pro Ala Ala
    130                 135                 140

Pro Cys Pro Leu Gly Glu Pro Lys Thr Gln Ala Cys Ser Gly Ser Glu
145                 150                 155                 160

Ser Pro Ser Asp Ser Glu Asn Glu Glu Ile Asp Val Val Thr Val Glu
                165                 170                 175

Lys Arg Gln Ser Leu Gly Ile Arg Lys Pro Val Thr Ile Thr Val Arg
            180                 185                 190
```

```
Ala Asp Pro Leu Asp Pro Cys Met Lys His Phe His Ile Ser Ile His
            195                 200                 205

Gln Gln Gln His Asn Tyr Ala Ala Arg Phe Pro Glu Ser Cys Ser
    210                 215                 220

Gln Glu Glu Ala Ser Glu Arg Gly Pro Gln Glu Val Leu Glu Arg
225                 230                 235                 240

Asp Ala Ala Gly Glu Lys Glu Asp Glu Glu Asp Glu Ile Val Ser
                245                 250                 255

Pro Pro Pro Val Glu Ser Glu Ala Ala Gln Ser Cys His Pro Lys Pro
                260                 265                 270

Val Ser Ser Asp Thr Glu Asp Val Thr Lys Arg Lys Asn His Asn Phe
    275                 280                 285

Leu Glu Arg Lys Arg Arg Asn Asp Leu Arg Ser Arg Phe Leu Ala Leu
    290                 295                 300

Arg Asp Gln Val Pro Thr Leu Ala Ser Cys Ser Lys Ala Pro Lys Val
305                 310                 315                 320

Val Ile Leu Ser Lys Ala Leu Glu Tyr Leu Gln Ala Leu Val Gly Ala
                325                 330                 335

Glu Lys Arg Met Ala Thr Glu Lys Arg Gln Leu Arg Cys Arg Gln Gln
                340                 345                 350

Gln Leu Gln Lys Arg Ile Ala Tyr Leu Thr Gly Tyr
            355                 360

<210> SEQ ID NO 5
<211> LENGTH: 3480
<212> TYPE: DNA
<213> ORGANISM: Mus musculus
<220> FEATURE:
<221> NAME/KEY: CDS
<222> LOCATION: (76)..(702)

<400> SEQUENCE: 5
cctttgcctc cggacttctc tggggccagc agccgcccga cctggggccc ggggccacgg      60
gctcagcaga cgacc atg ggc tcg gtg tcc aac cag cag ttt gca ggt ggc     111
                Met Gly Ser Val Ser Asn Gln Gln Phe Ala Gly Gly
                 1               5                  10 tgc gcc aag gca gcg gag aag gcg cca gag gag gcg ccg cct gac gcg     159
Cys Ala Lys Ala Ala Glu Lys Ala Pro Glu Glu Ala Pro Pro Asp Ala
        15                  20                  25 gcc cga gcg gca gac gag ccg cag ctg ctg cac ggg gcc ggc atc tgt     207
Ala Arg Ala Ala Asp Glu Pro Gln Leu Leu His Gly Ala Gly Ile Cys
    30                  35                  40 aag tgg ttc aac gtg cgc atg ggg ttc ggc ttc ctg tct atg acc gcc     255
Lys Trp Phe Asn Val Arg Met Gly Phe Gly Phe Leu Ser Met Thr Ala
45                  50                  55                  60 cgc gct ggg gtc gcg ctc gac ccc ccg gtg gac gtc ttt gtg cac cag     303
Arg Ala Gly Val Ala Leu Asp Pro Pro Val Asp Val Phe Val His Gln
                65                  70                  75 agc aag ctg cac atg gaa ggg ttc cga agc ctc aag gag ggt gag gcg     351
Ser Lys Leu His Met Glu Gly Phe Arg Ser Leu Lys Glu Gly Glu Ala
            80                  85                  90 gtg gag ttc acc ttt aag aag tct gcc aag ggt ctg gaa tcc atc cgt     399
Val Glu Phe Thr Phe Lys Lys Ser Ala Lys Gly Leu Glu Ser Ile Arg
        95                  100                 105 gtc act ggc cct ggt ggt gtg ttc tgt att ggg agt gag cgg cgg cca     447
Val Thr Gly Pro Gly Gly Val Phe Cys Ile Gly Ser Glu Arg Arg Pro
    110                 115                 120 aaa ggg aag aac atg cag aag cga aga tcc aaa gga gac agg tgc tac     495
```

|   |   |
|---|---|
| Lys Gly Lys Asn Met Gln Lys Arg Arg Ser Lys Gly Asp Arg Cys Tyr<br>125                                        130                        135                       140 |  |
| aac tgc ggt ggg cta gac cat cat gcc aag gaa tgc aag ctg cca ccc<br>Asn Cys Gly Gly Leu Asp His His Ala Lys Glu Cys Lys Leu Pro Pro<br>                          145                              150                            155 | 543 |
| cag ccc aag aag tgc cac ttt tgc caa agc atc aac cat atg gtg gcc<br>Gln Pro Lys Lys Cys His Phe Cys Gln Ser Ile Asn His Met Val Ala<br>                 160                            165                            170 | 591 |
| tcg tgt cca ctg aag gcc cag cag ggc ccc agt tct cag gga aag cct<br>Ser Cys Pro Leu Lys Ala Gln Gln Gly Pro Ser Ser Gln Gly Lys Pro<br>        175                            180                            185 | 639 |
| gcc tac ttc cgg gag gaa gag gaa gag atc cac agc cct gcc ctg ctc<br>Ala Tyr Phe Arg Glu Glu Glu Glu Glu Ile His Ser Pro Ala Leu Leu<br>      190                          195                            200 | 687 |
| cca gaa gcc cag aat tgaggcccag gagtcagggt tattctttgg ctaatgggga<br>Pro Glu Ala Gln Asn<br>205 | 742 |
| gtttaaggaa agaggcatca atctgcagag tggagaaagt gggggtaagg gtgggttgcg | 802 |
| tgggtagctt gcactgccgt gtctcaggcc ggggttccca gtgtcaccct gtctttcctt | 862 |
| ggagggaagg aaaggatgag acaaaggaac tcctaccaca ctctatctga aagcaagtga | 922 |
| aggcttttgt ggggaggaac caccctagaa cccgaggctt tgccaagtgg ctgggctagg | 982 |
| gaagttcttt tgtagaaggc tgtgtgatat ttcccttgcc agacgggaag cgaaacaagt | 1042 |
| gtcaaaccaa gattactgaa cctaccccctc cagctactat gttctgggga agggactccc | 1102 |
| aggagcaggg cgaggttatt ttcacaccgt gcttattcat aaccctgtcc tttggtgctg | 1162 |
| tgctgggaat ggtctctagc aacgggttgt gatgacaggc aaagagggtg gttggggaga | 1222 |
| caactgctga cctgctgccc acacctcact cccagccctt tctgggccaa tgggatttta | 1282 |
| atttatttgc tcccttaggt aactgcacct tgggtcccac tttctccagg atgccaactg | 1342 |
| cactatctac gtgcgaatga cgtatcttgt gcgttttttt tttttttaat ttttaaaatt | 1402 |
| tttttcatc ttcttaatat aaataatggg tttgtatttt tgtatatttt aatcttaagg | 1462 |
| ccctcattcc tgcactgtgt tctcaggtac atgagcaatc tcagggataa taagtccgta | 1522 |
| gcagctccag gtctgctcag caggaatact ttgttttgtt ttgttttgat caccatggag | 1582 |
| accaaccatt tggagtgcac agcctgttga actacctcat ttttgccgat tacagctggc | 1642 |
| ttttctgcca tagcgtcctt gaaaaatgtg tctcacgggt ttcgattgag ctgccccaag | 1702 |
| acttgatctg gatttggcaa aacataggac atcactctaa acaggaaagg gtggtacaga | 1762 |
| gacattaaaa ggctgggcca ggtgaaaggc acaagaggaa ctttccatac cagatccatc | 1822 |
| cttttgccag attagtggaa gcctgccatg cacagcaggg tgtgagagag agagtgtgta | 1882 |
| tgtatgtgtg tgtggatttt ttttaatgca aatttatgaa gacgaggtgg gttttgttta | 1942 |
| tttgattgct ttttgtgctg gggatggaat cttgggcttc atttgtgcta ggaagtacac | 2002 |
| tgccactgag ttatcccagt aagaatgcaa cttaagacca gtaccttat tcccacactg | 2062 |
| tgctgtccag gcatgggaac atgaggcagg gactcaactc cttagccttt cacaatcttg | 2122 |
| gctttctgag agactcatga gtatgggcct cagtggcaag tgtcctgccc tgctgtagcg | 2182 |
| tgatggttga tagctaaagg aaagaggggg tgggagttt cgtttacatg ctttgagatc | 2242 |
| gccacaaacc tacctcactg tgttgaaacg ggacaaatgc aatagaacac attgggtggt | 2302 |
| gtgtgtgtgt gtctgatctt ggtttcttgt ctccctctcc ccccaaatgc tgccctcacc | 2362 |
| cctagttaat tgtattcgtc tggccttttgt aggactttta ctgtctctga gttggtgatt | 2422 |

```
gctaggtggc ctagttgtgt aaatataaat gtgttggtct tcatgttctt ttggggtttt    2482
attgtttaca aaacttttgt tgtattgaga gaaaaatagc caaagcatct ttgacagaaa    2542
gctctgcacc agacaacacc atctgaaact taaatgtgcg gtcctcttct caaagtgaac    2602
ctctgggacc atggcttatc cttacctgtt cctcctgtgt ctcccattct ggaccacagt    2662
gaccttcaga cagcccctct tctccctcgt aagaaaactt aggctcattt acttctttga    2722
gcatctctgt aactcttgaa ggacccatgt gaaaattctg aagaagccag gaacctcatt    2782
ctttccttgt ccctaactca gtgaagagtt ttggttggtg gttttgagac agggcctcac    2842
tctgtagctg gagatagaga gcctcgggtt cctggctctc ctcctgcctt ctgcacagag    2902
tcccctgtgc agggattgca ggtgccgctt ctccctggca agaccattta tttcatggtg    2962
tgattcgcct ttggatggat caaaccaatg taatctgtca cccttaggtc gagagaagca    3022
attgtggggc cttccatgta gaaagttgga atctggacac cagaaaaggg actatgaatg    3082
tacagtgagt cactcaggaa cttaatgccg gtgcaagaaa cttatgtcaa agaggccaca    3142
agattgttac taggagacgg acgaatgtat ctccatgttt actgctagaa accaaagctt    3202
tgtgagaaat cttgaattta tggggagggt gggaaagggt gtacttgtct gtccttttcc    3262
catctctttc ctgaactgca ggagactaag gcccccacc ccccggggct tggatgaccc    3322 ccaccctgc ctgggtgtt ttatttccta gttgatttt actgtacccg ggcccttgta    3382
ttcctatcgt ataatcatcc tgtgacacat gctgactttt ccttcccttc tcttccctgg    3442
gaaaataaag acttattggt actccagagt tggtactg                           3480
```

<210> SEQ ID NO 6
<211> LENGTH: 209
<212> TYPE: PRT
<213> ORGANISM: Mus musculus

<400> SEQUENCE: 6

```
Met Gly Ser Val Ser Asn Gln Gln Phe Ala Gly Gly Cys Ala Lys Ala
1               5                   10                  15

Ala Glu Lys Ala Pro Glu Glu Ala Pro Pro Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Asn
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Asn His Met Val Ala Ser Cys Pro Leu
                165                 170                 175

Lys Ala Gln Gln Gly Pro Ser Ser Gln Gly Lys Pro Ala Tyr Phe Arg
            180                 185                 190
```

```
Glu Glu Glu Glu Glu Ile His Ser Pro Ala Leu Leu Pro Glu Ala Gln
            195                 200                 205
Asn

<210> SEQ ID NO 7
<211> LENGTH: 4014
<212> TYPE: DNA
<213> ORGANISM: Homo sapiens
<220> FEATURE:
<221> NAME/KEY: CDS
<222> LOCATION: (115)..(741)

<400> SEQUENCE: 7
gtgcggggga agatgtagca gcttcttctc cgaaccaacc ctttgccttc ggacttctcc      60
ggggccagca gccgcccgac caggggcccg gggccacggg ctcagccgac gacc atg     117
                                                              Met
                                                               1 ggc tcc gtg tcc aac cag cag ttt gca ggt ggc tgc gcc aag gcg gca     165
Gly Ser Val Ser Asn Gln Gln Phe Ala Gly Gly Cys Ala Lys Ala Ala
         5                  10                  15 gaa gag gcg ccc gag gag gcg ccg gag gac gcg gcc cgg gcg gcg gac     213
Glu Glu Ala Pro Glu Glu Ala Pro Glu Asp Ala Ala Arg Ala Ala Asp
     20                  25                  30 gag cct cag ctg ctg cac ggt gcg ggc atc tgt aag tgg ttc aac gtg     261
Glu Pro Gln Leu Leu His Gly Ala Gly Ile Cys Lys Trp Phe Asn Val
 35                  40                  45 cgc atg ggg ttc ggc ttc ctg tcc atg acc gcc cgc gcc ggg gtc gcg     309
Arg Met Gly Phe Gly Phe Leu Ser Met Thr Ala Arg Ala Gly Val Ala
 50                  55                  60                  65 ctc gac ccc cca gtg gat gtc ttt gtg cac cag agt aag ctg cac atg     357
Leu Asp Pro Pro Val Asp Val Phe Val His Gln Ser Lys Leu His Met
                 70                  75                  80 gaa ggg ttc cgg agc ttg aag gag ggt gag gca gtg gag ttc acc ttt     405
Glu Gly Phe Arg Ser Leu Lys Glu Gly Glu Ala Val Glu Phe Thr Phe
             85                  90                  95 aag aag tca gcc aag ggt ctg gaa tcc atc cgt gtc acc gga cct ggt     453
Lys Lys Ser Ala Lys Gly Leu Glu Ser Ile Arg Val Thr Gly Pro Gly
             100                 105                 110 gga gta ttc tgt att ggg agt gag agg cgg cca aaa gga aag agc atg     501
Gly Val Phe Cys Ile Gly Ser Glu Arg Arg Pro Lys Gly Lys Ser Met
    115                 120                 125 cag aag cgc aga tca aaa gga gac agg tgc tac aac tgt gga ggt cta     549
Gln Lys Arg Arg Ser Lys Gly Asp Arg Cys Tyr Asn Cys Gly Gly Leu
130                 135                 140                 145 gat cat cat gcc aag gaa tgc aag ctg cca ccc cag ccc aag aag tgc     597
Asp His His Ala Lys Glu Cys Lys Leu Pro Pro Gln Pro Lys Lys Cys
                150                 155                 160 cac ttc tgc cag agc atc agc cat atg gta gcc tca tgt ccg ctg aag     645
His Phe Cys Gln Ser Ile Ser His Met Val Ala Ser Cys Pro Leu Lys
            165                 170                 175 gcc cag cag ggc cct agt gca cag gga aag cca acc tac ttt cga gag     693
Ala Gln Gln Gly Pro Ser Ala Gln Gly Lys Pro Thr Tyr Phe Arg Glu
        180                 185                 190 gaa gaa gaa gaa atc cac agc cct acc ctg ctc ccg gag gca cag aat     741
Glu Glu Glu Glu Ile His Ser Pro Thr Leu Leu Pro Glu Ala Gln Asn
    195                 200                 205 tgagccacaa tgggtggggg ctattctttt gctatcagga agttttgagg agcaggcaga    801
gtggagaaag tgggaatagg gtgcattggg gctagttggc actgccatgt atctcaggct    861
```

```
tgggttcaca ccatcaccct ttcttccctc taggtggggg gaaagggtga gtcaaggaa    921
ctccaaccat gctctgtcca aatgcaagtg agggttctgg gggcaaccag gagggggaa    981
tcaccctaca acctgcatac tttgagtctc catccccaga atttccagct tttgaaagtg   1041
gcctggatag ggaagttgtt ttcctttaa agaaggatat ataataattc ccatgccaga    1101
gtgaaatgat taagtataag accagattca tggagccaag ccactacatt ctgtggaagg   1161
agatctctca ggagtaagca ttgtttttt ttcacatctt gtatcctcat acccactttt    1221
gggatagggt gctggcagct gtcccaagca atgggtaatg atgatggcaa aaagggtgtt   1281
tgggggaaca gctgcagacc tgctgctcta tgctcacccc cgccccattc tgggccaatg   1341
tgattttatt tatttgctcc cttggatact gcaccttggg tcccactttc tccaggatgc   1401
caactgcact agctgtgtgc gaatgacgta tcttgtgcat tttaactttt tttccttaat   1461
ataaatattc tggttttgta tttttgtata ttttaatcta aggccctcat ttcctgcact   1521
gtgttctcag gtacatgagc aatctcaggg atagccagca gcagctccag gtctgcgcag   1581
caggaattac tttttgttgt ttttgccacc gtggagagca actatttgga gtgcacagcc   1641
tattgaacta cctcattttt gccaataaga gctggctttt ctgccatagt gtcctcttga   1701
aaccccctct gccttgaaaa tgttttatgg gagactaggt tttaactggg tggccccatg   1761
acttgattgc cttctactgg aagattggga attagtctaa acaggaaatg gtggtacaca   1821
gaggctagga gaggctgggc ccggtgaaaa ggccagagag caagccaaga ttaggtgagg   1881
gttgtctaat cctatggcac aggacgtgct ttacatctcc agatctgttc ttcaccagat   1941
taggttaggc ctaccatgtg ccacagggtg tgtgtgtgtt tgtaaaacta gagttgctaa   2001
ggataagttt aaagaccaat acccctgtac ttaatcctgt gctgtcgagg gatggatata   2061
tgaagtaagg tgagatcctt aacctttcaa aattttcggg ttccagggag acacacaagc   2121
gagggttttg tggtgcctgg agcctgtgtc ctgccctgct acagtagtga ttaatagtgt   2181
catggtagct aaaggagaaa aaggggggttt cgtttacacg ctgtgagatc accgcaaacc   2241
taccttactg tgttgaaacg ggacaaatgc aatagaacgc attgggtggt gtgtgtctga   2301
tcctgggttc ttgtctcccc taaatgctgc cccccaagtt actgtatttg tctgggcttt   2361
gtaggacttc actacgttga ttgctaggtg gcctagtttg tgtaaatata atgtattggt   2421
ctttctccgt gttctttggg ggttttgttt acaaacttct ttttgtattg agagaaaaat   2481
agccaaagca tctttgacag aaggttctgc accaggcaaa aagatctgaa acattagttt   2541
gggggggcccc cttcttaaag tggggatctt gaaccatcct ttcttttgta ttccccttcc   2601
cctattacct attagaccag atcttctgtc ctaaaaactt gtcttctacc ctgccctctt   2661
ttctgttcac ccccaaaaga aaacttacac acccacacac atacacattt catgcttgga   2721
gtgtctccac aactcttaaa tgatgtatgc aaaaatactg aagctaggaa aaccctccat   2781
cccttgttcc caacctccta agtcaagacc attaccattt cttctttct ttttttttt    2841
tttttaaaat ggagtctcac tgtgtcaccc aggctggagt gcagtggcat gatcggctca   2901
ctgcagcctc tgcctcttgg gttcaagtga ttctcctgcc tcagcctcct gagtagctgg   2961
gatttcaggc acccgccaca ctcagctaat ttttgtattt ttagtagaga cggggtttca   3021
ccatgttgtc caggctggtc tggaactcct gacctcaggt gatctgccca ccttggcttc   3081
ccaaagtgct gggattacag gcatgagcca ccatgctggg ccaaccattt cttggtgtat   3141
tcatgccaaa cacttaagac actgctgtag cccaggcgcg gtggctcaca cctgtaatcc   3201
cagcactttg gaaggctgag gcgggcggat cacaaggtca cgagttcaaa actatcctgg   3261
```

```
ccaacacagt gaaaccccgt ctctactaaa atacaaaaaa attagccggg tgtggtggtg    3321
catgccttta gtcctagcta ttcaggaggc tgaggcaggg gaatcgcttg aacccgagag    3381
gcagaggttg cagtgagctg agatcgcacc actgcactcc agcctggtta cagagcaaga    3441
ctctgtctca aacaaaacaa aacaaaacaa aaacacacta ctgtattttg gatggatcaa    3501
acctccttaa ttttaatttc taatcctaaa gtaaagagat gcaattgggg gccttccatg    3561
tagaaagtgg ggtcaggagg ccaagaaagg gaatatgaat gtatatccaa gtcactcagg    3621 aactttatg caggtgctag aaactttatg tcaaagtggc cacaagattg tttaatagga    3681
gacgaacgaa tgtaactcca tgtttactgc taaaaaccaa agctttgtgt aaaatcttga    3741
atttatgggg cgggagggta ggaaagcctg tacctgtctg ttttttttcct gatccttttc    3801 cctcattcct gaactgcagg agactgagcc cctttgggct ttggtgaccc catcactggg    3861
gtgtgtttat ttgatggttg attttgctgt actgggtact tccttttccca ttttctaatc    3921 attttttaac acaagctgac tcttcccttc ccttctcctt tccctgggaa aatacaatga    3981
ataaataaag acttattggt acgcaaactg tca                                  4014
```

<210> SEQ ID NO 8
<211> LENGTH: 209
<212> TYPE: PRT
<213> ORGANISM: Homo sapiens

<400> SEQUENCE: 8

```
Met Gly Ser Val Ser Asn Gln Gln Phe Ala Gly Gly Cys Ala Lys Ala
1               5                   10                  15

Ala Glu Glu Ala Pro Glu Ala Pro Glu Asp Ala Ala Arg Ala Ala
            20                  25                  30

Asp Glu Pro Gln Leu Leu His Gly Ala Gly Ile Cys Lys Trp Phe Asn
    35                  40                  45

Val Arg Met Gly Phe Gly Phe Leu Ser Met Thr Ala Arg Ala Gly Val
50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn
```

<210> SEQ ID NO 9
<211> LENGTH: 5420

<212> TYPE: DNA
<213> ORGANISM: Mus musculus
<220> FEATURE:
<221> NAME/KEY: CDS
<222> LOCATION: (142)..(954)

<400> SEQUENCE: 9

```
aagaaggaaa gcacattaga ccatgcgaac taaatttgtg atcgcacaaa atcaagatgt      60
tagactgatg ctgaagatca ctccggtcca aagggaaagt tttcatctct ggagtttgaa     120
gctgagggcc ggtggggcaa c atg gcc gaa ggc ggg gca agc aaa ggt gaa       171
                        Met Ala Glu Gly Gly Ala Ser Lys Gly Glu
                         1               5                  10 gag cca gaa aaa ctg ccc ggg ctg gca gag gac gaa ccc cag gtt ctg       219
Glu Pro Glu Lys Leu Pro Gly Leu Ala Glu Asp Glu Pro Gln Val Leu
             15                  20                  25 cat ggc act ggc cac tgt aaa tgg ttc aac gtg cgc atg gga ttc gga       267
His Gly Thr Gly His Cys Lys Trp Phe Asn Val Arg Met Gly Phe Gly
         30                  35                  40 ttc atc tcc atg ata agt cga gag gga aat ccc ttg gat att cca gtg       315
Phe Ile Ser Met Ile Ser Arg Glu Gly Asn Pro Leu Asp Ile Pro Val
     45                  50                  55 gat gta ttt gta cac caa agc aaa cta ttc atg gaa gga ttt aga agc       363
Asp Val Phe Val His Gln Ser Lys Leu Phe Met Glu Gly Phe Arg Ser
 60                  65                  70 ttg aaa gaa gga gag cca gtg gaa ttt aca ttt aaa aaa tcc ccc aaa       411
Leu Lys Glu Gly Glu Pro Val Glu Phe Thr Phe Lys Lys Ser Pro Lys
 75                  80                  85                  90 ggc ctt gag tca ata cgg gta aca ggc cca ggt ggg agc ccc tgc tta       459
Gly Leu Glu Ser Ile Arg Val Thr Gly Pro Gly Gly Ser Pro Cys Leu
                 95                 100                 105 gga agt gaa aga aga cct aaa ggg aag acc ctg caa aag aga aag cca       507
Gly Ser Glu Arg Arg Pro Lys Gly Lys Thr Leu Gln Lys Arg Lys Pro
             110                 115                 120 aag gga gat agg tgg aga cgg cag gat tta ctg atg gat cag atg tgg       555
Lys Gly Asp Arg Trp Arg Arg Gln Asp Leu Leu Met Asp Gln Met Trp
         125                 130                 135 act gtg cga gaa gaa gag tcc agg atg att cca aga tgc tac aac tgt       603
Thr Val Arg Glu Glu Glu Ser Arg Met Ile Pro Arg Cys Tyr Asn Cys
     140                 145                 150 ggt ggt ctc gac cat cat gct aaa gaa tgc agt cta cct cct cag cca       651
Gly Gly Leu Asp His His Ala Lys Glu Cys Ser Leu Pro Pro Gln Pro
155                 160                 165                 170 aag aag tgc cat tac tgt cag agc atc atg cac atg gtg gcc aac tgc       699
Lys Lys Cys His Tyr Cys Gln Ser Ile Met His Met Val Ala Asn Cys
                 175                 180                 185 cca cac aag ctt gcc gct cag ctg ccc gcc agt tct cag gga aga cag       747
Pro His Lys Leu Ala Ala Gln Leu Pro Ala Ser Ser Gln Gly Arg Gln
             190                 195                 200 gag gca gaa tcc cag cca tgc agc tct gcg gca cca aga gaa gtg gga       795
Glu Ala Glu Ser Gln Pro Cys Ser Ser Ala Ala Pro Arg Glu Val Gly
         205                 210                 215 ggg ggg cat ggc tgc aca gta ctg ttt cct cag gag gtg aag tca gaa       843
Gly Gly His Gly Cys Thr Val Leu Phe Pro Gln Glu Val Lys Ser Glu
     220                 225                 230 atg gca gag cac tca gac agg tca ccc caa gaa gtt tct tcc acg aaa       891
Met Ala Glu His Ser Asp Arg Ser Pro Gln Glu Val Ser Ser Thr Lys
235                 240                 245                 250 gcg ttt gca gca ata gga gag caa aac aaa aag ggg cct ttg att cag       939
Ala Phe Ala Ala Ile Gly Glu Gln Asn Lys Lys Gly Pro Leu Ile Gln
                 255                 260                 265
```

```
aaa cgg aaa aag act tagtacttgt cagtgttccc ttcacccggg cgggaagtct       994
Lys Arg Lys Lys Thr
            270 acctcatgca agcacagggg aatagtggtc cacagagagc agccggccgg gatgttaact    1054 actgctgagg aactgggaag ttcttaatta gacaaatcac tcttaagcaa actacattta    1114 agcagggtgt catgttttat agaattgaga tactacatat agtatgtgca taagtgagag    1174 gggagacttg aatctgtatg tatgtgtgag gatttcacat aagagtacag gcacacacac    1234 acatatatat atacactttt atatatctgt ggttgtcttt gtgtgtgtgt gtgtgtgtat    1294 gtgtgtgtgt gtgtgtgtgt atgtagataa aagcacatac tcttcctcag ataattgggc    1354 atctctaagc attgaaaatc catgtgaagc atttgagatg gtttcatagt taacccttgg    1414 aatttttctt aaatactact tcttttatat tatgtaaaaa atgaccacgt gactgttacc    1474 tttcatgtga accaaagcat acttcagatc tcagagctgc cagtcaaatg gtactaaagg    1534 cttttgggat acttggtgcc tcccaagtct gtattcataa ctctatcttg atgctgatag    1594 agtgttttgc tgttgctgtt atctgtcttc tcctgtttga aggtagtaac ttaactctag    1654 atgcctccga ctgccataag cttttaatcc ttggatacgt agctccagaa aagacaatga    1714 atgtgaactt cctgtgctga tatttcagtg tcttttattc tgtttgattg taaattacat    1774 ggctattaag aaaaatgaag gggagggtaa tgtatatagt aacatggtcc ttttcagtgg    1834 tattttgatg ctaggtcttt tacaagggtt ctgaggtttt taagggatgg tggcaacaga    1894 agcctccttt gactaagtag cttttgaacc atcacttaga tcaggaaggt ctcttactta    1954 ctactgaagc cttagagaaa attttaatta tttgggtata ttttttggtag ctgtttttat    2014 ttccctgga gagtcctcag acctgtttat aaaacaaaca aaagcagcat agaaataaaa    2074 tagtggggct tagaatgaaa attaagttgc ccaatagata cagcccatga ttgatactaa    2134 aaagaatagt gtttgatggc cagcagagtg aatgagtgga gcagagttac caaagtgccc    2194 actgttctgt ggctagaaat actttatatg ataatattga tgccatggca ggttccttga    2254 gtatagaagc ggaagtatgg tgtgtgatag attcaggatg agcactcaga tcaagttata    2314 ggatcttctc agatggattc tcagtttgct aagattggct aggaactgat tgtagtattg    2374 ggctgttttc catcatgttt tgttttcttt tgttttttga atggagttag cctggttcta    2434 aatgtcatga gcaaactttt gaaacatctt caagaaggta ccaagggatt gcagtgcata    2494 attttggctg taactatatg ggcctgttgg tataagctca gataatcaaa caagaaagca    2554 tcgtgactca tgagacacat tctacggagg agtcgcttcc tcctgtgtgt cttgtcatgg    2614 gagttgggtg gtgctaaggt ttcatcaagc cactagaaga agaaagtgtc tccgactagc    2674 ttaccagtct tttccagagt agcttgaatt gcttgacagt atttatgaga gttcctatag    2734 tgttttaccg aagtgtcagt gtgctgtaat acagagctta cctttgacga tattgaatgt    2794 gatgtagcca tagagaagtg ctgccttgcc ttacgtgagg atttcaagct tatttaaatt    2854 atgtagacaa atcaaaggtc atccaagtat aatgagcaag gtaacagttg tacaagcaaa    2914 atatgatagg tcactctgaa cgctcaaacc aaagttcctt gactatcaaa ataggaaata    2974 atggacttga aaactggaca ttctgtttac atttaaaatt taagagctga ggtcatttta    3034 acaaatgaaa gtagaaaatt cagaaacact tgaatataga ccttatgggt gcagtcaact    3094 tcttttcagc atctaaccag accgacttac taaaagcaca taccaaacct atcttatggt    3154 taaaagttta ttttttatat gaaaatagtg tcactattac atgctcagga caagaacttt    3214
```

```
tgctcaggga acataccata taatgttttt attgttttt tttgttttgt tttgttttgt      3274
tttgttttt tacagactaa tgtataatcc tgctttctca gagcaagcca aataaattaa      3334
gtctttatgt acgtacatat acttgttagt aactacctct gagtttgaca ttgatcataa      3394
ttctgaatat cagatattgg tcctcccttt taaatttca tgtcaaagtc ttgtaaagcg      3454
gaattccact acctgcagat gtgaactcac tgatatgagc acttgctcat tcacacaagt      3514
gaaaattctg tttacagcac atggctacct cccagctacc acagagcaca ccttgatgct      3574
gctgcagcct gcaggttgct gataattctc tggtacagac gcttttaatc tgtagcacag      3634
ataggcattt gcaactgcat gtttctgaaa acgcctgtt tttctcatag atttctcatg       3694
ttaagtagca aaatctccaa gcatttcctt agagttatca tgtattaaat gtaaggaagt      3754
atggacactc taatttatcc taggccaaac agaacacaga acaatcttg aaaatagctc       3814
tgttacctag aggtgagggg cagcagagat aacaaaagga aacttggtgt ttgtatttg      3874
ctgacaagtg ttataaaaga ttcctaccgc ttcacttgta tctctacagt actgaaggca      3934
aagcatactg cagcattcca agcctcaggc acacaactaa ctagcaccag cttgccatgg      3994
gggaacttaa agtgcagtgt tgccttgagc cagaggggaa cggggtctgt ggagcaccac      4054
tttgcagggg ttcctcatag tgcggtgtgg tttgagccat cttttgacct cccccttaca      4114
gcaacacaaa tgtaactcct aaaaaacgat tcactaccag cctttagcct gcgaactatt      4174
cgttctctac acagcaggac acagtggaca cattttata cttgcatttc taatctttgg       4234
atgtatttt acaaatgaaa gacttaggaa gatttttatc tgcttatcac ctggaaattt       4294
tagtgtgcaa tctaaagaaa aagataaaga catcacatta ttagcatcag tccacctccc      4354
aaatatagga tgttttattg ccaattattt ttgtattctg gctgagcttt attttgcacc      4414
agggcaggcc taacttgccg ctggttgtat gtagtttgtg aatagaagcc cataagtgtt      4474
aatagacctt gtaacattcg ctgtaagatg aattatacag gatgtgggga atctcagtaa      4534
gtcttaaagt taatttaaag taattttatct gttttctcta agaaatgttt atcataaaat      4594
atatatgtaa cttcccatt tggtataaaa tctagggaag tgtgtgcaag tggagttgtg       4654
ctgactttga atttctagat gtcttaatga gatttatttg ttttagaaaa agaacaactt      4714
gttgaaagca cccagttctg tcttacatac tgtcaacagc ctcttcaagt tgtgcctgtg      4774
tgatctgtga cctcctgttc ctttaaagtg agacagtgac ctatgactca ttgttgacct      4834
tatacttgga acagaactac ggcatttacg gtggagtcct gtacgacgag aaagtgtcag      4894
gatatgcaac gcacctgtgg cttacccctt gacggcccag cttggaaatg atggcaccga      4954
ctacctcttc aatcacttgt ggctatcaac cacaggcact tagcaccagg ctggctttaa      5014
ttagtgtgtg ttgttttgt ggtggtaaca actctatcca tatgaagacc aaagtgaacc       5074
ctggtttcta tatgtcttta atgcagtgtt gtatctagta tttggaaatt atctcattca      5134
gtgtttagat tacctcactc cattttgatt catgttgttt acaagtgaac atttttttaa      5194
agatacactt gaaattgcgt tagaaagaac aaaggaggag ttgctattag actggcacag      5254
tgcattccac agacttggtg gactgctctc tgcagacatg ggcctaggac tgtctttgta      5314
ccgaatgtct tactctgttg gctattgatg tttaaaattt catgatagaa aataaaagac      5374
acaatgttgg tgtttaagat gggtttggaa aaaaaaaaaa aaaaaa                    5420
```

<210> SEQ ID NO 10
<211> LENGTH: 271
<212> TYPE: PRT
<213> ORGANISM: Mus musculus -continued

<400> SEQUENCE: 10

Met Ala Glu Gly Gly Ala Ser Lys Gly Glu Glu Pro Glu Lys Leu Pro
1               5                   10                  15

Gly Leu Ala Glu Asp Glu Pro Gln Val Leu His Gly Thr Gly His Cys
            20                  25                  30

Lys Trp Phe Asn Val Arg Met Gly Phe Gly Phe Ile Ser Met Ile Ser
        35                  40                  45

Arg Glu Gly Asn Pro Leu Asp Ile Pro Val Asp Val Phe Val His Gln
    50                  55                  60

Ser Lys Leu Phe Met Glu Gly Phe Arg Ser Leu Lys Glu Gly Glu Pro
65                  70                  75                  80

Val Glu Phe Thr Phe Lys Lys Ser Pro Lys Gly Leu Glu Ser Ile Arg
                85                  90                  95

Val Thr Gly Pro Gly Gly Ser Pro Cys Leu Gly Ser Glu Arg Arg Pro
            100                 105                 110

Lys Gly Lys Thr Leu Gln Lys Arg Lys Pro Lys Gly Asp Arg Trp Arg
        115                 120                 125

Arg Gln Asp Leu Leu Met Asp Gln Met Trp Thr Val Arg Glu Glu Glu
    130                 135                 140

Ser Arg Met Ile Pro Arg Cys Tyr Asn Cys Gly Gly Leu Asp His His
145                 150                 155                 160

Ala Lys Glu Cys Ser Leu Pro Pro Gln Pro Lys Lys Cys His Tyr Cys
                165                 170                 175

Gln Ser Ile Met His Met Val Ala Asn Cys Pro His Lys Leu Ala Ala
            180                 185                 190

Gln Leu Pro Ala Ser Ser Gln Gly Arg Gln Glu Ala Glu Ser Gln Pro
        195                 200                 205

Cys Ser Ser Ala Ala Pro Arg Glu Val Gly Gly His Gly Cys Thr
    210                 215                 220

Val Leu Phe Pro Gln Glu Val Lys Ser Glu Met Ala Glu His Ser Asp
225                 230                 235                 240

Arg Ser Pro Gln Glu Val Ser Ser Thr Lys Ala Phe Ala Ala Ile Gly
                245                 250                 255

Glu Gln Asn Lys Lys Gly Pro Leu Ile Gln Lys Arg Lys Lys Thr
            260                 265                 270

<210> SEQ ID NO 11
<211> LENGTH: 5517
<212> TYPE: DNA
<213> ORGANISM: Homo sapiens
<220> FEATURE:
<221> NAME/KEY: CDS
<222> LOCATION: (204)..(953)

<400> SEQUENCE: 11
aattgacaaa gtcacgtgtg ctcagggggc cagaaactgg agagaggaga gaaaaaaatc      60
aaaagaagga aagcacatta gaccatgcga gctaaatttg tgatcgcaca aaatcaagat     120
gttagattga tgcagaagat cactccgttc caaagggaaa gttttcatct cacgagtttg     180
gagctgaggg cccgtggggc aac atg gcc gaa ggc ggg gct agc aaa ggt ggt     233
                          Met Ala Glu Gly Gly Ala Ser Lys Gly Gly
                          1               5                    10 gga gaa gag ccc ggg aag ctg ccg gag ccg gca gag gag gaa tcc cag        281
Gly Glu Glu Pro Gly Lys Leu Pro Glu Pro Ala Glu Glu Glu Ser Gln
                15                  20                  25

| | | |
|---|---|---|
| gtt ttg cgc gga act ggc cac tgt aag tgg ttc aat gtg cgc atg gga<br>Val Leu Arg Gly Thr Gly His Cys Lys Trp Phe Asn Val Arg Met Gly<br>30                         35                  40 | | 329 |
| ttt gga ttc atc tcc atg ata aac cga gag gga agc ccc ttg gat att<br>Phe Gly Phe Ile Ser Met Ile Asn Arg Glu Gly Ser Pro Leu Asp Ile<br>          45                      50                      55 | | 377 |
| cca gtc gat gta ttt gta cac caa agc aaa cta ttc atg gaa gga ttt<br>Pro Val Asp Val Phe Val His Gln Ser Lys Leu Phe Met Glu Gly Phe<br>60                         65                     70 | | 425 |
| aga agc cta aaa gaa gga gaa cca gtg gaa ttc aca ttt aaa aaa tct<br>Arg Ser Leu Lys Glu Gly Glu Pro Val Glu Phe Thr Phe Lys Lys Ser<br>75                         80                     85                  90 | | 473 |
| tcc aaa ggc ctt gag tca ata cgg gta aca gga cct ggt ggg agc ccc<br>Ser Lys Gly Leu Glu Ser Ile Arg Val Thr Gly Pro Gly Gly Ser Pro<br>                 95                     100                     105 | | 521 |
| tgt tta gga agt gaa aga aga ccc aaa ggg aag aca cta cag aaa aga<br>Cys Leu Gly Ser Glu Arg Arg Pro Lys Gly Lys Thr Leu Gln Lys Arg<br>110                        115                    120 | | 569 |
| aaa cca aag gga gat aga tgc tac aac tgt ggt ggc ctt gat cat cat<br>Lys Pro Lys Gly Asp Arg Cys Tyr Asn Cys Gly Gly Leu Asp His His<br>             125                    130                     135 | | 617 |
| gct aag gaa tgt agt cta cct cct cag cca aag aag tgc cat tac tgt<br>Ala Lys Glu Cys Ser Leu Pro Pro Gln Pro Lys Lys Cys His Tyr Cys<br>140                        145                    150 | | 665 |
| cag agc atc atg cac atg gtg gca aac tgc cca cat aaa aat gtt gca<br>Gln Ser Ile Met His Met Val Ala Asn Cys Pro His Lys Asn Val Ala<br>155                        160                    165                    170 | | 713 |
| cag cca ccc gcg agt tct cag gga aga cag gaa gca gaa tcc cag cca<br>Gln Pro Pro Ala Ser Ser Gln Gly Arg Gln Glu Ala Glu Ser Gln Pro<br>                     175                    180                    185 | | 761 |
| tgc act tca act ctc cct cga gaa gtg gga ggc ggg cat ggc tgt aca<br>Cys Thr Ser Thr Leu Pro Arg Glu Val Gly Gly Gly His Gly Cys Thr<br>190                        195                    200 | | 809 |
| tca cca ccg ttt cct cag gag gct agg gca gag atc tca gaa cgg tca<br>Ser Pro Pro Phe Pro Gln Glu Ala Arg Ala Glu Ile Ser Glu Arg Ser<br>            205                    210                    215 | | 857 |
| ggc agg tca cct caa gaa gct tcc tcc acg aag tca tct ata gca cca<br>Gly Arg Ser Pro Gln Glu Ala Ser Ser Thr Lys Ser Ser Ile Ala Pro<br>220                        225                    230 | | 905 |
| gaa gag caa agc aaa aag ggg cct tca gtt caa aaa agg aaa aag aca<br>Glu Glu Gln Ser Lys Lys Gly Pro Ser Val Gln Lys Arg Lys Lys Thr<br>235                        240                    245                    250 | | 953 |
| taacaggtct tcttcatatg ttctttcctt tacccggttg caaagtctac ctcatgcaag | | 1013 |
| tatagggaa cagtatttca caagcagtag ctgacctggg attttaacta ctattgggga | | 1073 |
| actgtgaatt ttttaaacag acaaatcact ctaagcaaat tacatttgag cagggtgtca | | 1133 |
| tgttttatgt taattcagag aataagatac tatgtctgtc aatatgtgca tgtgtgagag | | 1193 |
| ggagagagcc tgagtctgtg tgtgtacatg aggattttta tataggaatg tagcacacata | | 1253 |
| tataaagagg ctttgtcttt atatatttgt gtatagatca aagcacacac cctctctcat | | 1313 |
| ataattggat atttccaaga attgaaaacc catgtgaagc attatagata gtttttaaatt | | 1373 |
| taacccactg gagttttctt gaataccac ttctttttata ttatataaaa ctaaaaacac | | 1433 |
| gactgttacc ttttgtgtga accaaaggat acttcagatc tcagagctgc caattatggg | | 1493 |
| gtactaaagg ttttttaagac atccagttct cccgaatttg ggattgcctc tttttcttga | | 1553 |
| aatctctgga gtagtaattt ttttccccct ttttgaaagg cagtacctta acttcatatg | | 1613 |
| cctctgactg ccataagctt ttttgattct gggataacat aactccagaa aagacaatga | | 1673 |

```
atgtgtaatt tgggccgata tttcactgtt ttaaattctg tgtttaattg taaaattaga    1733
tgcctattaa gagaaatgaa ggggaggatc atcttagtgg cttgttttca gtagtatttt    1793
aatatcagct tcttgtaacc ttttccatgt tgtgagggtt gtaagggatt gtgtggcaac    1853
agcagcttcc cttggctaac tcaatcttct acccattgct tagagcaggg agccctcctt    1913
atttactact gaagacctta gagaactcca attgtttggc atatatttt ggtggtggtt    1973
tttattcctc ctggagagtt atctaatttg tttctaaaac aaacaagcag caagaaatg    2033
aattaaatac tggggttgag aattaaaatt aagtggatgt tcacagttgc ccaatatata    2093
tgacctgcaa atgatacgaa aaagtgcagc atttagtggc agttaacaag agtgacaagc    2153
ctggggcaga ggtaccaaac ctctcccacc agagagctag aagtatttta tacagtaact    2213
ttgatcttat ggaagtgacc ttcaatgctt attctgaagt aacctatatg gtggatacag    2273
gatgaacatt cagtgccagg gagaatcttc tcaggttggt tctcgttaga gtgataaact    2333
ggctaggggc catagtattg gtcctgttag gtttcggtca tggaaaaaaa aattattttg    2393
gggtcatcct ggctctagat gttatgggca aatttctgaa acatctgcaa gaaggtacca    2453
gttaattata gtgcttaata ttgggaataa gattaagcat tataattata atgtatgggc    2513
ctgttggtgt aagctcagat aattaaataa aaatagcatg actcaaatga gacatattct    2573
gctgaacagt ttctacttcc tctcccgcct gtcctgtcat gggagacgtg tatagttgct    2633
gctgtttcag caaaccacca taagacgaaa atgcctcagg ttgggttgcc agtcctttac    2693
aactcagctt gaatttcaca acagtgattg tgagaatctg cgtggtatac actgaaatat    2753
cggtgtgctg tgatgcaaag cttacctttg acgatattga atgtgatata gctgtagaga    2813
agtacttcct tgccttatgt gaggatttca aacttattta aattatgtag acaaatcaaa    2873
gtggcattgc ttaattttta gcaggcataa taagcaagtt aacagtaaaa tgcaaaacat    2933
gataagcgtt gctcaatttt tagcaggtat aataagcagg ttaacagtaa aaatgcaaaa    2993
catgatagat aagtcacttt gaaaattcaa accaaagttc cttcaccttn tggaaatagg    3053
aaattatgga cttcaaaatt ggacacttcc tgtttacaaa aagaaattca gagctaaaat    3113
catggtaaaa aaaatagaa acacttgaga actatggtct ttatgggtgc aatttgaaat    3173
cctttcatc atcttaccag actaaactaa gagcacatac caaacctatc ttatggttga    3233
aagttggggt ttatttttta tatgagaata ttatcactat tacataacat actcaggaca    3293
aagaactttg ctcagggaac ataccatgta atatttttgt tgtttcttta cagactagtc    3353
tacagtcctg cttactcaaa acaaaccaaa taacttatac ctttatataa gtattatgta    3413
ctgatgatag taactaccte tgagtttgac acagatcaaa attttgaat atcagatatc    3473
agttatccta tttttatttc atgtgaaaac tcctctaaag cagattccct caactctgtg    3533
catatgtgaa tatcactgat gtgaacacat tgttcattta cataggtaaa atattactct    3593
gtttacagca aaaggctacc tcatagttga tacatagcac acctgtatgt atgctgttcc    3653
agccttacag gtggctgata attctctggt acagaacctt tttatctgta ttataaatag    3713
caattcacaa ctgcatgttt ctgacaaaca cttgtgaata atgaagcatc tcgtttagt    3773
tagcaaagtc tccaaacatt tccttaaaat aatcatgtat ttagtttaaa gaattatggg    3833
cactgttcaa cttaagcaaa acagaacacg gaagcagtct tagaagcacc actttgccca    3893
gaggtggagg ttggaagggg tagcagggag aggggttggt gtatgcaggt attcatgcta    3953
ggcaaagagt ttaaaagacg ccaatgtcct tcatttactg tctgtgctgc cctgaagcca    4013
```

| | |
|---|---|
| agcgtattgc agcattatag ccccaggcac ataactaact agcactggct tgccaaggaa | 4073 |
| tgaacatgca atgccattac tagctattga gggaaaaggg tctgtgtgaa gcatcacttt | 4133 |
| gcagggatta ctaatggtgg ggcagcaggt ctgtgaatta agttatctct tgacctcacc | 4193 |
| ctcatgtcaa cacaaatgta attcctaaac aagatgcatt gccagtctct tagccctgta | 4253 |
| agctgatctt ttgctacatg gcagactata atgaaaacat ttttatactt gggtttctag | 4313 |
| tcttcactag aaggccttgg atgtattttt gcagttgaaa gatttagaaa gattttttacc | 4373 |
| tgcttataac ttggaagttt agagtgcaat gtaagaaaaa agatcaagaa atgtcatgtt | 4433 |
| attagcatca gtccacctcc aatattgccg atactttttt tattctggct cagttttatt | 4493 |
| ttgcaccagt gcggccccaa gttactgctg gttgtattta gtttgtgaat aggagcccat | 4553 |
| aagtgttaat agactttgta acattcacta taagatgaat tatacaggac atgggaaatc | 4613 |
| tcattaagtc ttaaagttaa tttaaattaa tttatctgtt ttctctaaga aatgtttatc | 4673 |
| ataaatata tatgtgtatt tcccctttgg ttataaaatt tgggaaagta tgtacaagtg | 4733 |
| cagctgcact gactttaatt ttctagatgt cttaatgaga tttatttgtt ttagagaaga | 4793 |
| acatcttgtt aaaagcatca aactctgtct tacatagctg tcaacagcct ctttaagatg | 4853 |
| tggtggttgt atgatctgtg tcttaattgt tcagttagag tgagaagttg acctatgatt | 4913 |
| cattttaaa ttttatattt ggaacaaagc tgcaagttat ggtaaagtac tgtactgtga | 4973 |
| gaagtattat gatatttaat gcatctgtgg cttaacactt gtgagagtta ccagcttgaa | 5033 |
| aatgatggtg ttgactacct cttgaatcac atctatcaac cactggcacc taccaccaag | 5093 |
| ctggcttcaa ttagtatgtg ttgcttttttg gtattaacaa ctaaccgtac tagagaccaa | 5153 |
| agtgaaccct gattttttata tgtctttaat aatggtgttt tatctagtgt ttttaaatta | 5213 |
| tcctgtgtag tatttagatt acctcattgt ccattttgac tcatgttgtt tacaagtgaa | 5273 |
| aataaaaaca cttgaactgt atgtttttaa aagacaaaaa aggggtagat gtttggaatg | 5333 |
| cgtttcactc gcatgcagtc atctggaggg actgaagcac tgtttgcctt tctgtacact | 5393 |
| ctgggtttta tattctcatt tcatgcctaa tgtcttattc tgtcaattat ggatatgttg | 5453 |
| aggtttaaaa aaattacttg attaaaaata aaacatataa cgttggcatt taaaaaaaaa | 5513 |
| aaaa | 5517 |

<210> SEQ ID NO 12
<211> LENGTH: 250
<212> TYPE: PRT
<213> ORGANISM: Homo sapiens

<400> SEQUENCE: 12

Met Ala Glu Gly Gly Ala Ser Lys Gly Gly Glu Glu Pro Gly Lys
1               5                   10                  15

Leu Pro Glu Pro Ala Glu Glu Ser Gln Val Leu Arg Gly Thr Gly
            20                  25                  30

His Cys Lys Trp Phe Asn Val Arg Met Gly Phe Gly Phe Ile Ser Met
            35                  40                      45

Ile Asn Arg Glu Gly Ser Pro Leu Asp Ile Pro Val Asp Val Phe Val
        50                  55                      60

His Gln Ser Lys Leu Phe Met Glu Gly Phe Arg Ser Leu Lys Glu Gly
65                  70                      75                  80

Glu Pro Val Glu Phe Thr Phe Lys Lys Ser Lys Gly Leu Glu Ser
                85                  90                  95

Ile Arg Val Thr Gly Pro Gly Gly Ser Pro Cys Leu Gly Ser Glu Arg

-continued

```
            100                 105                 110
Arg Pro Lys Gly Lys Thr Leu Gln Lys Arg Lys Pro Lys Gly Asp Arg
        115                 120                 125

Cys Tyr Asn Cys Gly Gly Leu Asp His His Ala Lys Glu Cys Ser Leu
130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Pro Ala Ser Ser
                165                 170                 175

Gln Gly Arg Gln Glu Ala Glu Ser Gln Pro Cys Thr Ser Thr Leu Pro
            180                 185                 190

Arg Glu Val Gly Gly His Gly Cys Thr Ser Pro Pro Phe Pro Gln
        195                 200                 205

Glu Ala Arg Ala Glu Ile Ser Glu Arg Ser Gly Arg Ser Pro Gln Glu
    210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250

<210> SEQ ID NO 13
<211> LENGTH: 4208
<212> TYPE: DNA
<213> ORGANISM: Mus musculus
<220> FEATURE:
<221> NAME/KEY: CDS
<222> LOCATION: (272)..(1633)

<400> SEQUENCE: 13
agtgggctcc aagtgtcggg cgccccagcc tcctccacgg cttggcgtcc cctctgcccg      60
ttcgctgagc gcgcggatga gtgggagcgc ggagctgcgc gcggctctct gcctccggct     120
cccccgccgc ggccgcgtcc tcccactccg ccttctcgcg ctcaccgtgc cgcggccg       180 ggactcgcac ctcgcctgtg cccttcactc gtcttccgcg tgatttgccc gccgcctttc    240
tcctccaact gggaatgcta aacgggact g atg gac gtg tcc gaa ctc tgc        292
                                 Met Asp Val Ser Glu Leu Cys
                                  1               5 atc ccg gac ccc ctt ggc tac cac aac cag ctg ctg aac cga atg tcg      340
Ile Pro Asp Pro Leu Gly Tyr His Asn Gln Leu Leu Asn Arg Met Ser
         10                  15                  20 tcc gaa gac agg cac ctg ggc tct agt tgc ggc tcc ttc atc aag acg      388
Ser Glu Asp Arg His Leu Gly Ser Ser Cys Gly Ser Phe Ile Lys Thr
 25                  30                  35 gag cca tcc agc ccg tcc tcg ggc att gat gcc ctc agc cac cac agc      436
Glu Pro Ser Ser Pro Ser Ser Gly Ile Asp Ala Leu Ser His His Ser
40                  45                  50                  55 ccc agc ggc tcg tcg gac gcc agt ggt ggc ttt ggc att gcc ctg agc      484
Pro Ser Gly Ser Ser Asp Ala Ser Gly Gly Phe Gly Ile Ala Leu Ser
                 60                  65                  70 acc cac gcc aac ggt ctg gac tcg ccg cct atg ttc gca ggt gcg ggg      532
Thr His Ala Asn Gly Leu Asp Ser Pro Pro Met Phe Ala Gly Ala Gly
         75                  80                  85 ctg gga ggc aac ccg tgc cgc aag agc tac gag gac tgt act agt ggt      580
Leu Gly Gly Asn Pro Cys Arg Lys Ser Tyr Glu Asp Cys Thr Ser Gly
     90                  95                 100 atc atg gag gac tcc gcc atc aaa tgc gag tac atg ctt aac gcc atc      628
Ile Met Glu Asp Ser Ala Ile Lys Cys Glu Tyr Met Leu Asn Ala Ile
105                 110                 115
```

-continued

| | | |
|---|---|---|
| ccc aag cgc ctg tgc ctc gtg tgc ggg gac att gcc tct ggc tac cac<br>Pro Lys Arg Leu Cys Leu Val Cys Gly Asp Ile Ala Ser Gly Tyr His<br>120                            125                       130                      135 | 676 |
| tac gga gtg gcc tcc tgc gag gct tgc aag gcg ttc ttc aag aga acc<br>Tyr Gly Val Ala Ser Cys Glu Ala Cys Lys Ala Phe Phe Lys Arg Thr<br>140                         145                      150 | 724 |
| att caa ggc aac atc gag tac aac tgc ccg gcc acc aat gaa tgt gag<br>Ile Gln Gly Asn Ile Glu Tyr Asn Cys Pro Ala Thr Asn Glu Cys Glu<br>155                         160                      165 | 772 |
| atc acc aaa cgg agg cgc aag tcc tgt cag gcc tgc cga ttc atg aaa<br>Ile Thr Lys Arg Arg Arg Lys Ser Cys Gln Ala Cys Arg Phe Met Lys<br>        170                       175                      180 | 820 |
| tgc ctc aaa gtg ggg atg ctg aag gaa ggt gtg cgc ctt gac cga gtt<br>Cys Leu Lys Val Gly Met Leu Lys Glu Gly Val Arg Leu Asp Arg Val<br>185                         190                      195 | 868 |
| cga gga ggc cgc cag aag tac aag cga cgg ctg gat tcg gag aac agc<br>Arg Gly Gly Arg Gln Lys Tyr Lys Arg Arg Leu Asp Ser Glu Asn Ser<br>200                         205                      210                      215 | 916 |
| ccc tac ctg aac ctg ccg att tcc cca cct gct aaa aag cca ttg act<br>Pro Tyr Leu Asn Leu Pro Ile Ser Pro Pro Ala Lys Lys Pro Leu Thr<br>                     220                       225                      230 | 964 |
| aag atc gtc tcg aat cta cta ggg gtt gag cag gac aag ctg tat gct<br>Lys Ile Val Ser Asn Leu Leu Gly Val Glu Gln Asp Lys Leu Tyr Ala<br>235                         240                      245 | 1012 |
| atg cct ccc aac gat atc ccc gag gga gat atc aag gcc ctg acc act<br>Met Pro Pro Asn Asp Ile Pro Glu Gly Asp Ile Lys Ala Leu Thr Thr<br>                     250                       255                      260 | 1060 |
| ctc tgt gaa ttg gca gat cgg gag ctt gtg ttc ctc atc aac tgg gcc<br>Leu Cys Glu Leu Ala Asp Arg Glu Leu Val Phe Leu Ile Asn Trp Ala<br>265                         270                      275 | 1108 |
| aag cac atc cca ggc ttc ccc agt ctg aca ctt ggg gac cag atg agc<br>Lys His Ile Pro Gly Phe Pro Ser Leu Thr Leu Gly Asp Gln Met Ser<br>280                         285                      290                      295 | 1156 |
| ctg ctg cag agt gcc tgg atg gag att ctc atc ttg ggc atc gtg tac<br>Leu Leu Gln Ser Ala Trp Met Glu Ile Leu Ile Leu Gly Ile Val Tyr<br>                     300                       305                      310 | 1204 |
| cgc tcg ctc cca tac gat gac aag ctg gca tac gcc gag gac tat atc<br>Arg Ser Leu Pro Tyr Asp Asp Lys Leu Ala Tyr Ala Glu Asp Tyr Ile<br>315                         320                      325 | 1252 |
| atg gat gag gaa cac tct cgc ctg gta ggg ctg ctg gac ctt tac cga<br>Met Asp Glu Glu His Ser Arg Leu Val Gly Leu Leu Asp Leu Tyr Arg<br>                     330                       335                      340 | 1300 |
| gcc atc ctg cag ctg gtg cgc agg tac aag aaa ctc aag gta gag aag<br>Ala Ile Leu Gln Leu Val Arg Arg Tyr Lys Lys Leu Lys Val Glu Lys<br>345                         350                      355 | 1348 |
| gaa gag ttt atg atc ctc aag gcc ctg gcc ctc gcc aac tca gat tcg<br>Glu Glu Phe Met Ile Leu Lys Ala Leu Ala Leu Ala Asn Ser Asp Ser<br>360                         365                      370                      375 | 1396 |
| atg tac att gag aac ctg gag gcg gtg cag aag ctc cag gac ctg ctg<br>Met Tyr Ile Glu Asn Leu Glu Ala Val Gln Lys Leu Gln Asp Leu Leu<br>                     380                       385                      390 | 1444 |
| cac gag gcg ctg cag gac tat gag ctg agt cag cgc cac gag gag ccg<br>His Glu Ala Leu Gln Asp Tyr Glu Leu Ser Gln Arg His Glu Glu Pro<br>395                         400                      405 | 1492 |
| cgg agg gcc ggc aag ctg ctg ctg acg ctg ccc ctg ctg agg cag aca<br>Arg Arg Ala Gly Lys Leu Leu Leu Thr Leu Pro Leu Leu Arg Gln Thr<br>                     410                       415                      420 | 1540 |
| gcc gcc aaa gcc gtg caa cac ttc tac agt gtg aaa ctg cag ggc aag<br>Ala Ala Lys Ala Val Gln His Phe Tyr Ser Val Lys Leu Gln Gly Lys | 1588 |

```
              425                 430                 435
gtg ccc atg cac aaa ctc ttc ctg gag atg ctg gag gcc aag gtg           1633
Val Pro Met His Lys Leu Phe Leu Glu Met Leu Glu Ala Lys Val
440                 445                 450 tgatggccca gcacatggac ggacggacac gatccaagtg agacctcca cagccaccag     1693
cctcgacttt tttcacaccc gcatcgggc tctgagctgt cccagaagaa ggggtcttct      1753
tgcttcctgg ccatgtgcag actcctgggg acagcagatg ggaggtggg gatggggagg     1813
gtaggggcgg ggggctcatc tgtcacccgc attttctttg gaatttttttt tttccttctc    1873
catgggcagt gctaaggctt gggccaggga cgacttccct tagagctgga gaccaccaga    1933
ggaagcagcc ttcctgcaag ggatccattt ctggacctct ccctatttag gacctggagg    1993
tatctggatg ggcagtgctt agtgcccggg acccaagaga catagattgg gggctcctga    2053
aggtgttggt gtcacggtgg gcagtccctt ggggcagaac gtctctgtgg cctatcccga    2113
ggctctgttc ctcctccatc tagctggctc cctccacttt cccctttctt attgtcccag    2173
tacacccagt tctcagtgga tgctcctgct agagtagcca catccccacc ccgaagaacc    2233
cctcccctgc ttcctgcccc tacctcagcc agccggaact cactggctca gaaaagagtt    2293
gggttctgta cccactgctc tttttgcctg ctgtttctcc ttctcctctt gggcatggcc    2353
agtctagaaa cctatggaga attcaggacc tggccccacc agaggtcact tgagggactc    2413
tcaaggtcag tagcttaggt tggggtgtag gatagcagag agaccagcg gtagagggaa     2473
agtctcattg cacctcggaa aggaaggagc tctaaaggtc cccttggcc cctcccttac      2533
ctcataaaaa ggcaaggctt ggctttgtgc cataggaggg cagcctcctg gcatttgcac    2593
cagggatgtt tgatgcagcc ctcctgggtc aattcccggc aagaccctgc agtctggttg    2653
tcgtataggg tgctccacca acccaccgca gtcctaaaac ccctcagccc taggcacatg    2713
aatgcacctt tcacccaccc aaaaggcagt cccaggctca tgctgtgtgt gtccttgggt    2773
ttgggttgac aggatgtcct aaagatgaag cggttcattc tggaaaatgg acacgccact    2833
ttcatgacaa gtcctccggc tttacctgct ctgatcccct cctggagtgc aagggtcccc    2893
tctttcaggc gttctggcac ctgccactac tgctggctct gctcccggg tgacacctct     2953
aggagactgg tcacttcaca gacttaatgc taaacttccc cagagagcct ttccctgccc    3013
ttttgcccac aaaggggttc atgcctctgc atgggctctc cttgcccatg atccaaggta    3073
gataccactt ttgtgttaaa ctgggttaac tcttaggggc tgggtttagc tatcctggct    3133
tctgaaaact ccccccagcc acactgtgga gagggggtgt cacctaaaat tccacctagt    3193
tctcagaatg tcttctgggc ctatgaacac accagcaagg gttggacaaa cacccacagc    3253
tgcctgagcg gacacactgc tttgaagcag cagcagcagc agttaaatgg cacctcggc     3313
tcggctcctt gatctagtga tgcaagcacc ccatacggct gcttacctgc cgaagagaat    3373
ggaccagtga cagttgggtg ccctgtaggg aagctgggtg ccctgggcac ctggagtcag    3433
agggtagagc ccacttgttc aaagactagc cagatgagag acatctgtga tgccagggtg    3493
ctcaaaacag gaaaaagcaa gagagaccct ctcctattcc cacctccccc cagtcagagc    3553
aaaaacccag gctaccttcc atatccattt ctggaaccca tggagaggag gcctctctct    3613
gctagtgtgt attcagataa agattatttc aacccagaaa tataaacata gctaaccttg    3673
taccttgtag aaggaggtgc tggctggat ctctttctct cgttccctaa cctttctgaa     3733
gattctggat ggttctggcg tgcctcccag gttttgcatc cgtgaacaga tgacttccca    3793
tggacagagc ttgagaaata cgaggctctc atttgggcct agcagggtca gagcctttac    3853
```

```
tatctgtgcc tggtccttcc ctccagactt gactactcat gagaaacagg tggcaggcaa    3913
ggatgacaga cgtgtgacaa ggagacagga gggcccagag tccaagccca tggaacagca    3973
ccaaagagaa gcactatgtg gagagattgc tttattttct gataatgacg ttgtggctgg    4033
aatgacttaa gatgtatata ttttttaacc ggcagtcctt cgtgctgtct caccccctg     4093 tatggacatg tcctcccacg gccctcatgt aaactacatg ccctgggatt atctcccatc    4153
cagtcccatg tatctgaaat ctaataaata aggaaaggtc tgctgaaaaa aaaaa          4208
```

<210> SEQ ID NO 14
<211> LENGTH: 454
<212> TYPE: PRT
<213> ORGANISM: Mus musculus

<400> SEQUENCE: 14

```
Met Asp Val Ser Glu Leu Cys Ile Pro Asp Pro Leu Gly Tyr His Asn
1               5                   10                  15

Gln Leu Leu Asn Arg Met Ser Ser Glu Asp Arg His Leu Gly Ser Ser
            20                  25                  30

Cys Gly Ser Phe Ile Lys Thr Glu Pro Ser Ser Pro Ser Ser Gly Ile
        35                  40                  45

Asp Ala Leu Ser His His Ser Pro Ser Gly Ser Ser Asp Ala Ser Gly
    50                  55                  60

Gly Phe Gly Ile Ala Leu Ser Thr His Ala Asn Gly Leu Asp Ser Pro
65                  70                  75                  80

Pro Met Phe Ala Gly Ala Gly Leu Gly Gly Asn Pro Cys Arg Lys Ser
                85                  90                  95

Tyr Glu Asp Cys Thr Ser Gly Ile Met Glu Asp Ser Ala Ile Lys Cys
            100                 105                 110

Glu Tyr Met Leu Asn Ala Ile Pro Lys Arg Leu Cys Leu Val Cys Gly
        115                 120                 125

Asp Ile Ala Ser Gly Tyr His Tyr Gly Val Ala Ser Cys Glu Ala Cys
    130                 135                 140

Lys Ala Phe Phe Lys Arg Thr Ile Gln Gly Asn Ile Glu Tyr Asn Cys
145                 150                 155                 160

Pro Ala Thr Asn Glu Cys Glu Ile Thr Lys Arg Arg Arg Lys Ser Cys
                165                 170                 175

Gln Ala Cys Arg Phe Met Lys Cys Leu Lys Val Gly Met Leu Lys Glu
            180                 185                 190

Gly Val Arg Leu Asp Arg Val Arg Gly Gly Arg Gln Lys Tyr Lys Arg
        195                 200                 205

Arg Leu Asp Ser Glu Asn Ser Pro Tyr Leu Asn Leu Pro Ile Ser Pro
    210                 215                 220

Pro Ala Lys Lys Pro Leu Thr Lys Ile Val Ser Asn Leu Leu Gly Val
225                 230                 235                 240

Glu Gln Asp Lys Leu Tyr Ala Met Pro Pro Asn Asp Ile Pro Glu Gly
                245                 250                 255

Asp Ile Lys Ala Leu Thr Thr Leu Cys Glu Leu Ala Asp Arg Glu Leu
            260                 265                 270

Val Phe Leu Ile Asn Trp Ala Lys His Ile Pro Gly Phe Pro Ser Leu
        275                 280                 285

Thr Leu Gly Asp Gln Met Ser Leu Leu Gln Ser Ala Trp Met Glu Ile
    290                 295                 300

Leu Ile Leu Gly Ile Val Tyr Arg Ser Leu Pro Tyr Asp Asp Lys Leu
```

```
                305                 310                 315                 320
Ala Tyr Ala Glu Asp Tyr Ile Met Asp Glu Glu His Ser Arg Leu Val
                    325                 330                 335

Gly Leu Leu Asp Leu Tyr Arg Ala Ile Leu Gln Leu Val Arg Arg Tyr
                340                 345                 350

Lys Lys Leu Lys Val Glu Lys Glu Phe Met Ile Leu Lys Ala Leu
            355                 360                 365

Ala Leu Ala Asn Ser Asp Ser Met Tyr Ile Glu Asn Leu Glu Ala Val
            370                 375                 380

Gln Lys Leu Gln Asp Leu Leu His Glu Ala Leu Gln Asp Tyr Glu Leu
385                 390                 395                 400

Ser Gln Arg His Glu Glu Pro Arg Arg Ala Gly Lys Leu Leu Leu Thr
                405                 410                 415

Leu Pro Leu Leu Arg Gln Thr Ala Ala Lys Ala Val Gln His Phe Tyr
                420                 425                 430

Ser Val Lys Leu Gln Gly Lys Val Pro Met His Lys Leu Phe Leu Glu
            435                 440                 445

Met Leu Glu Ala Lys Val
    450

<210> SEQ ID NO 15
<211> LENGTH: 3029
<212> TYPE: DNA
<213> ORGANISM: Homo sapiens
<220> FEATURE:
<221> NAME/KEY: CDS
<222> LOCATION: (372)..(1895)

<400> SEQUENCE: 15
ccgcagagag gtgtggtcag ggacatttcc cctggccggg agcccatgga gcactgtcct      60
cagagatgcg caggttaggc tcactgtcta ggccaggccc accttagtca ctgtggactg     120
gcaatggaag ctcttcctgg acacacctgc cctagccctc accctggggt ggaagagaaa     180
tgagcttggc ttgcaactca gaccattcca cggaggcatc ctccccttcc tgggctggtg     240
aataaaagtt tcctgaggtc aaggacttcc ttttccctgc caaaatggtg tccagaactt     300
tgaggccaga ggtgatccag tgatttggga gctgcaggtc acacaggctg ctcagagggc     360
tgctgaacag g atg tcc tcg gac gac agg cac ctg ggc tcc agc tgc ggc       410
             Met Ser Ser Asp Asp Arg His Leu Gly Ser Ser Cys Gly
               1               5                  10 tcc ttc atc aag act gag ccg tcc agc ccg tcc tcg ggc atc gat gcc       458
Ser Phe Ile Lys Thr Glu Pro Ser Ser Pro Ser Ser Gly Ile Asp Ala
 15                  20                  25 ctc agc cac cac agc ccc agt ggc tcg tcc gac gcc agc ggc ggc ttt       506
Leu Ser His His Ser Pro Ser Gly Ser Ser Asp Ala Ser Gly Gly Phe
 30                  35                  40                  45 ggc ctg gcc ctg ggc acc cac gcc aac ggt ctg gac tcg cca ccc atg       554
Gly Leu Ala Leu Gly Thr His Ala Asn Gly Leu Asp Ser Pro Pro Met
                 50                  55                  60 ttt gca ggc gcc ggg ctg gga ggc acc cca tgc cgc aag agc tac gag       602
Phe Ala Gly Ala Gly Leu Gly Gly Thr Pro Cys Arg Lys Ser Tyr Glu
             65                  70                  75 gac tgt gcc agc ggc atc atg gag gac tcg gcc atc aag tgc gag tac       650
Asp Cys Ala Ser Gly Ile Met Glu Asp Ser Ala Ile Lys Cys Glu Tyr
         80                  85                  90 atg ctc aac gcc atc ccc aag cgc ctg tgc ctc gtg tgc ggg gac att       698
Met Leu Asn Ala Ile Pro Lys Arg Leu Cys Leu Val Cys Gly Asp Ile
     95                 100                 105
```

-continued

| | | |
|---|---|---|
| gcc tct ggc tac cac tac ggc gtg gcc tcc tgc gag gct tgc aag gcc<br>Ala Ser Gly Tyr His Tyr Gly Val Ala Ser Cys Glu Ala Cys Lys Ala<br>110                               115                      120                       125 | 746 | |
| ttc ttc aag agg act atc caa ggg aac att gag tac agc tgc ccg gcc<br>Phe Phe Lys Arg Thr Ile Gln Gly Asn Ile Glu Tyr Ser Cys Pro Ala<br>130                      135                    140 | 794 | |
| acc aac gag tgc gag atc acc aaa cgg agg cgc aag tcc tgc cag gcc<br>Thr Asn Glu Cys Glu Ile Thr Lys Arg Arg Arg Lys Ser Cys Gln Ala<br>145                      150                    155 | 842 | |
| tgc cgc ttc atg aaa tgc ctc aaa gtg ggg atg ctg aag gaa ggt gtg<br>Cys Arg Phe Met Lys Cys Leu Lys Val Gly Met Leu Lys Glu Gly Val<br>160                      165                    170 | 890 | |
| cgc ctt gat cga gtg cgt gga ggc cgt cag aaa tac aag cga cgg ctg<br>Arg Leu Asp Arg Val Arg Gly Gly Arg Gln Lys Tyr Lys Arg Arg Leu<br>175                      180                    185 | 938 | |
| gac tca gag agc agc cca tac ctg agc tta caa att tct cca cct gct<br>Asp Ser Glu Ser Ser Pro Tyr Leu Ser Leu Gln Ile Ser Pro Pro Ala<br>190                      195                    200                    205 | 986 | |
| aaa aag cca ttg acc aag att gtc tca tac cta ctg gtg gct gag ccg<br>Lys Lys Pro Leu Thr Lys Ile Val Ser Tyr Leu Leu Val Ala Glu Pro<br>210                      215                    220 | 1034 | |
| gac aag ctc tat gcc atg cct ccc cct ggt atg cct gag ggg gac atc<br>Asp Lys Leu Tyr Ala Met Pro Pro Pro Gly Met Pro Glu Gly Asp Ile<br>225                      230                    235 | 1082 | |
| aag gcc ctg acc act ctc tgt gac ctg gca gac cga gag ctt gtg gtc<br>Lys Ala Leu Thr Thr Leu Cys Asp Leu Ala Asp Arg Glu Leu Val Val<br>240                      245                    250 | 1130 | |
| atc att ggc tgg gcc aag cac atc cca ggc ttc tca agc ctc tcc ctg<br>Ile Ile Gly Trp Ala Lys His Ile Pro Gly Phe Ser Ser Leu Ser Leu<br>255                      260                    265 | 1178 | |
| ggg gac cag atg agc ctg ctg cag agt gcc tgg atg gaa atc ctc atc<br>Gly Asp Gln Met Ser Leu Leu Gln Ser Ala Trp Met Glu Ile Leu Ile<br>270                      275                    280                    285 | 1226 | |
| ctg ggc atc gtg tac cgc tcg ctg ccc tat gac gac aag ctg gtg tac<br>Leu Gly Ile Val Tyr Arg Ser Leu Pro Tyr Asp Asp Lys Leu Val Tyr<br>290                      295                    300 | 1274 | |
| gct gag gac tac atc atg gat gag gag cac tcc cgc ctc gcg ggg ctg<br>Ala Glu Asp Tyr Ile Met Asp Glu Glu His Ser Arg Leu Ala Gly Leu<br>305                      310                    315 | 1322 | |
| ctg gag ctc tac cgg gcc atc ctg cag ctg gta cgc agg tac aag aag<br>Leu Glu Leu Tyr Arg Ala Ile Leu Gln Leu Val Arg Arg Tyr Lys Lys<br>320                      325                    330 | 1370 | |
| ctc aag gtg gag aag gag gag ttt gtg acg ctc aag gcc ctg gcc ctc<br>Leu Lys Val Glu Lys Glu Glu Phe Val Thr Leu Lys Ala Leu Ala Leu<br>335                      340                    345 | 1418 | |
| gcc aac tcc gat tcc atg tac atc gag gat cta gag gct gtc cag aag<br>Ala Asn Ser Asp Ser Met Tyr Ile Glu Asp Leu Glu Ala Val Gln Lys<br>350                      355                    360                    365 | 1466 | |
| ctg cag gac ctg ctg cac gag gca ctg cag gac tac gag ctg agc cag<br>Leu Gln Asp Leu Leu His Glu Ala Leu Gln Asp Tyr Glu Leu Ser Gln<br>370                      375                    380 | 1514 | |
| cgc cat gag gag ccc tgg agg acg ggc aag ctg ctg ctg aca ctg ccg<br>Arg His Glu Glu Pro Trp Arg Thr Gly Lys Leu Leu Leu Thr Leu Pro<br>385                      390                    395 | 1562 | |
| ctg ctg cgg cag acg gcc gcc aag gcc gtg cag cac ttc tat agc gtc<br>Leu Leu Arg Gln Thr Ala Ala Lys Ala Val Gln His Phe Tyr Ser Val<br>400                      405                    410 | 1610 | |
| aaa ctg cag ggc aaa gtg ccc atg cac aaa ctc ttc ctg gag atg ctg<br>Lys Leu Gln Gly Lys Val Pro Met His Lys Leu Phe Leu Glu Met Leu | 1658 | |

```
                415                 420                 425
gag gcc aag gtt ggc caa gag cag ctt aga gga tct ccc aag gat gaa    1706
Glu Ala Lys Val Gly Gln Glu Gln Leu Arg Gly Ser Pro Lys Asp Glu
430                 435                 440                 445 aga atg tca agc cat gat gga aaa tgc ccc ttc caa tca gct gcc ttc    1754
Arg Met Ser Ser His Asp Gly Lys Cys Pro Phe Gln Ser Ala Ala Phe
                450                 455                 460 aca agc agg gat cag agc aac tcc ccg ggg atc ccc aat cca cgc cct    1802
Thr Ser Arg Asp Gln Ser Asn Ser Pro Gly Ile Pro Asn Pro Arg Pro
            465                 470                 475 tct agt cca acc ccc ctc aat gag aga ggc agg cag atc tca ccc agc    1850
Ser Ser Pro Thr Pro Leu Asn Glu Arg Gly Arg Gln Ile Ser Pro Ser
        480                 485                 490 act agg aca cca gga ggc cag gga aag cat ctc tgg ctc acc atg        1895
Thr Arg Thr Pro Gly Gly Gln Gly Lys His Leu Trp Leu Thr Met
    495                 500                 505 taacatctgg cttggagcaa gtgggtgttc tgcacaccag gcagctgcac ctcactggat    1955
ctagtgttgc tgcgagtgac ctcacttcag agccctcta gcagagtggg gcggaagtcc    2015
tgatggttgg tgtccatgag gtggaagctg cttttatact taaaactcag atcacaacag    2075
gaaatgtgtc agtaacaatg gaactccatc caatgggaaa gttcctggta ctgaaggggt    2135
ccattggaca ctcagaaaag aagttcaggg gccaacttct tagctggaat cctggccaga    2195
tgaggaccct ctccgggaaa gggagaggac tgacttagtg gaaggtggtg aagtgaggag    2255
agtttagggg aaccttcccc cagtggaaca gatctcaagt ttaccctaaa cctgccattt    2315
ctggaaaatc tgtaaagagg aaacagcctg tctcagctgt actctcatga tacaggtcat    2375
ttgaaatgaa ccaagaaata aaacatgaaa atccaaccat ggagaaggtg gtatggctgg    2435
gttttgtttg gtccccttgt ccttatacgt tctaaagttt ccagactggc tttgtcactt    2495
tgtgaactcg tcatgtgtga aaaccaatct ttgcatatag ggaacttcct cgggccacac    2555
tttaagaacc aagtaagagg ctctcaagac tccagcagag tcgggaggcc atggcagcgc    2615
cttagaggag ctggaacctg cacccacctg tgtcggtggg gggggcctcc tttccccata    2675
gactctgccc tccctctgtg cagatggaag tggcagggga gggtgaccag cttgtgacaa    2735
gaagactgaa gggtccagag tccatgctca cggaacagca ccaaagaaaa gcactatgtg    2795
gaaagattgt tttattttct aataatgata atatggctgg aatggcttct taagatgtat    2855
atatttttta aaatggcagt tccccattgc agcatcacct acttgtatgt ctttctgcct    2915
ctgtatatgt tctcccagaa acccccatgt aaatcaaatg ccctaggatg cttccatcct    2975
ggtcccatgt atctggaatc taataaataa ggaaaggaaa aaaaaaaaa aaaa           3029

<210> SEQ ID NO 16
<211> LENGTH: 508
<212> TYPE: PRT
<213> ORGANISM: Homo sapiens

<400> SEQUENCE: 16

Met Ser Ser Asp Asp Arg His Leu Gly Ser Ser Cys Gly Ser Phe Ile
1               5                   10                  15

Lys Thr Glu Pro Ser Ser Pro Ser Gly Ile Asp Ala Leu Ser His
            20                  25                  30

His Ser Pro Ser Gly Ser Ser Asp Ala Ser Gly Gly Phe Gly Leu Ala
        35                  40                  45

Leu Gly Thr His Ala Asn Gly Leu Asp Ser Pro Pro Met Phe Ala Gly
    50                  55                  60
```

```
Ala Gly Leu Gly Gly Thr Pro Cys Arg Lys Ser Tyr Glu Asp Cys Ala
 65                  70                  75                  80

Ser Gly Ile Met Glu Asp Ser Ala Ile Lys Cys Glu Tyr Met Leu Asn
                 85                  90                  95

Ala Ile Pro Lys Arg Leu Cys Leu Val Cys Gly Asp Ile Ala Ser Gly
            100                 105                 110

Tyr His Tyr Gly Val Ala Ser Cys Glu Ala Cys Lys Ala Phe Phe Lys
        115                 120                 125

Arg Thr Ile Gln Gly Asn Ile Glu Tyr Ser Cys Pro Ala Thr Asn Glu
    130                 135                 140

Cys Glu Ile Thr Lys Arg Arg Lys Ser Cys Gln Ala Cys Arg Phe
145                 150                 155                 160

Met Lys Cys Leu Lys Val Gly Met Leu Lys Glu Gly Val Arg Leu Asp
                165                 170                 175

Arg Val Arg Gly Gly Arg Gln Lys Tyr Lys Arg Arg Leu Asp Ser Glu
            180                 185                 190

Ser Ser Pro Tyr Leu Ser Leu Gln Ile Ser Pro Pro Ala Lys Lys Pro
        195                 200                 205

Leu Thr Lys Ile Val Ser Tyr Leu Leu Val Ala Glu Pro Asp Lys Leu
    210                 215                 220

Tyr Ala Met Pro Pro Gly Met Pro Glu Gly Asp Ile Lys Ala Leu
225                 230                 235                 240

Thr Thr Leu Cys Asp Leu Ala Asp Arg Glu Leu Val Val Ile Ile Gly
                245                 250                 255

Trp Ala Lys His Ile Pro Gly Phe Ser Leu Ser Leu Gly Asp Gln
            260                 265                 270

Met Ser Leu Leu Gln Ser Ala Trp Met Glu Ile Leu Ile Leu Gly Ile
        275                 280                 285

Val Tyr Arg Ser Leu Pro Tyr Asp Asp Lys Leu Val Tyr Ala Glu Asp
    290                 295                 300

Tyr Ile Met Asp Glu Glu His Ser Arg Leu Ala Gly Leu Leu Glu Leu
305                 310                 315                 320

Tyr Arg Ala Ile Leu Gln Leu Val Arg Arg Tyr Lys Lys Leu Lys Val
                325                 330                 335

Glu Lys Glu Glu Phe Val Thr Leu Lys Ala Leu Ala Leu Ala Asn Ser
            340                 345                 350

Asp Ser Met Tyr Ile Glu Asp Leu Glu Ala Val Gln Lys Leu Gln Asp
        355                 360                 365

Leu Leu His Glu Ala Leu Gln Asp Tyr Glu Leu Ser Gln Arg His Glu
    370                 375                 380

Glu Pro Trp Arg Thr Gly Lys Leu Leu Leu Thr Leu Pro Leu Leu Arg
385                 390                 395                 400

Gln Thr Ala Ala Lys Ala Val Gln His Phe Tyr Ser Val Lys Leu Gln
                405                 410                 415

Gly Lys Val Pro Met His Lys Leu Phe Leu Glu Met Leu Glu Ala Lys
            420                 425                 430

Val Gly Gln Glu Gln Leu Arg Gly Ser Pro Lys Asp Glu Arg Met Ser
        435                 440                 445

Ser His Asp Gly Lys Cys Pro Phe Gln Ser Ala Ala Phe Thr Ser Arg
    450                 455                 460

Asp Gln Ser Asn Ser Pro Gly Ile Pro Asn Pro Arg Pro Ser Ser Pro
465                 470                 475                 480
```

Thr Pro Leu Asn Glu Arg Gly Arg Gln Ile Ser Pro Ser Thr Arg Thr
                485                 490                 495

Pro Gly Gly Gln Gly Lys His Leu Trp Leu Thr Met
    500                 505

<210> SEQ ID NO 17
<211> LENGTH: 5312
<212> TYPE: DNA
<213> ORGANISM: Mus musculus
<220> FEATURE:
<221> NAME/KEY: CDS
<222> LOCATION: (171)..(1544)

<400> SEQUENCE: 17
ccaatcgggg ctttaagtcc ttgattagga gagagtgtgc gagcctcggt cccaactggc      60
cgtgcctatg ggcctgtcac caggagaacg cgtgtgttaa ttgcaccggg ctctgtcaag     120
gaaactttga tttataggtg gggtgcacaa ataatggttg tcgggcgcac atg gat       176
                                                       Met Asp
                                                         1 tcg gta gaa ctt tgc ctg cct gaa tct ttt tcc ctg cac tac gaa gaa      224
Ser Val Glu Leu Cys Leu Pro Glu Ser Phe Ser Leu His Tyr Glu Glu
      5                  10                  15 gag ctt ctc tgc aga atg tca aac aaa gat cga cac att gat tcc agc      272
Glu Leu Leu Cys Arg Met Ser Asn Lys Asp Arg His Ile Asp Ser Ser
 20                  25                  30 tgt tcg tcc ttc atc aag acg gaa ccc tcc agc cca gcc tcc ctg acg      320
Cys Ser Ser Phe Ile Lys Thr Glu Pro Ser Ser Pro Ala Ser Leu Thr
 35                  40                  45                  50 gac agc gtc aac cac cac agc cct ggt ggg tct tcc gac gcc agt ggg      368
Asp Ser Val Asn His His Ser Pro Gly Gly Ser Ser Asp Ala Ser Gly
                 55                  60                  65 agt tac agt tca acc atg aat ggc cat cag aac gga ctg gac tcg cca      416
Ser Tyr Ser Ser Thr Met Asn Gly His Gln Asn Gly Leu Asp Ser Pro
         70                  75                  80 cct ctc tac ccc tct gct ccg atc ctg gga ggc agc ggg cct gtc cgg      464
Pro Leu Tyr Pro Ser Ala Pro Ile Leu Gly Gly Ser Gly Pro Val Arg
     85                  90                  95 aaa ctg tat gat gac tgc tcc agc acc atc gta gag gat ccc cag acc      512
Lys Leu Tyr Asp Asp Cys Ser Ser Thr Ile Val Glu Asp Pro Gln Thr
100                 105                 110 aag tgt gaa tat atg ctc aac tcc atg ccc aag aga ctg tgc tta gtg      560
Lys Cys Glu Tyr Met Leu Asn Ser Met Pro Lys Arg Leu Cys Leu Val
115                 120                 125                 130 tgt ggc gac atc gcc tct ggg tac cac tat ggg gtt gca tca tgt gaa      608
Cys Gly Asp Ile Ala Ser Gly Tyr His Tyr Gly Val Ala Ser Cys Glu
                135                 140                 145 gcc tgc aag gca ttc ttc aag agg acg att caa ggt aac ata gag tac      656
Ala Cys Lys Ala Phe Phe Lys Arg Thr Ile Gln Gly Asn Ile Glu Tyr
            150                 155                 160 agc tgc cca gcc acg aat gaa tgt gag atc aca aag cgc aga cgc aaa      704
Ser Cys Pro Ala Thr Asn Glu Cys Glu Ile Thr Lys Arg Arg Arg Lys
        165                 170                 175 tcc tgc cag gcc tgc cgc ttc atg aag tgt ctc aaa gtg ggc atg ctg      752
Ser Cys Gln Ala Cys Arg Phe Met Lys Cys Leu Lys Val Gly Met Leu
    180                 185                 190 aaa gaa ggg gtc cgt ctt gac aga gtg cgt gga ggt cgg cag aag tac      800
Lys Glu Gly Val Arg Leu Asp Arg Val Arg Gly Gly Arg Gln Lys Tyr
195                 200                 205                 210 aag cgc aga ata gat gct gag aac agc cca tac ctg aac cct cag ctg      848
Lys Arg Arg Ile Asp Ala Glu Asn Ser Pro Tyr Leu Asn Pro Gln Leu -continued

| | | | |
|---|---|---|---|
| gtg cag cca gcc aaa aag cca tat aac aag att gtc tcg cat ttg ttg<br>Val Gln Pro Ala Lys Lys Pro Tyr Asn Lys Ile Val Ser His Leu Leu<br>230 235 240 | | | 896 |
| gtg gct gaa cca gag aag atc tat gcc atg cct gac cct act gtc ccc<br>Val Ala Glu Pro Glu Lys Ile Tyr Ala Met Pro Asp Pro Thr Val Pro<br>245 250 255 | | | 944 |
| gac agt gac atc aaa gcc ctc acc aca ctc tgt gac ttg gct gac cga<br>Asp Ser Asp Ile Lys Ala Leu Thr Thr Leu Cys Asp Leu Ala Asp Arg<br>260 265 270 | | | 992 |
| gag ttg gtg gtt atc att gga tgg gca aaa cat att cca ggc ttc tcc<br>Glu Leu Val Val Ile Ile Gly Trp Ala Lys His Ile Pro Gly Phe Ser<br>275 280 285 290 | | | 1040 |
| aca ctg tcc ctg gca gac cag atg agc ctc ctc cag agt gca tgg atg<br>Thr Leu Ser Leu Ala Asp Gln Met Ser Leu Leu Gln Ser Ala Trp Met<br>295 300 305 | | | 1088 |
| gag att ctg atc ctc ggc gtt gtg tac cga tcg ctt tcg ttt gag gat<br>Glu Ile Leu Ile Leu Gly Val Val Tyr Arg Ser Leu Ser Phe Glu Asp<br>310 315 320 | | | 1136 |
| gaa ctt gtc tat gca gac gat tat ata atg gat gaa gac cag tct aaa<br>Glu Leu Val Tyr Ala Asp Asp Tyr Ile Met Asp Glu Asp Gln Ser Lys<br>325 330 335 | | | 1184 |
| tta gca ggc ctt ctt gac cta aat aat gct atc ctg cag ctg gtg aag<br>Leu Ala Gly Leu Leu Asp Leu Asn Asn Ala Ile Leu Gln Leu Val Lys<br>340 345 350 | | | 1232 |
| aag tac aag agc atg aag cta gag aag gaa gaa ttc gtc acc ctc aaa<br>Lys Tyr Lys Ser Met Lys Leu Glu Lys Glu Glu Phe Val Thr Leu Lys<br>355 360 365 370 | | | 1280 |
| gca ata gct ctt gct aat tca gat tcc atg cat ata gaa gat gtg gaa<br>Ala Ile Ala Leu Ala Asn Ser Asp Ser Met His Ile Glu Asp Val Glu<br>375 380 385 | | | 1328 |
| gct gtg cag aaa ctt cag gat gtg tta cat gag gcc ctg cag gat tac<br>Ala Val Gln Lys Leu Gln Asp Val Leu His Glu Ala Leu Gln Asp Tyr<br>390 395 400 | | | 1376 |
| gag gct ggc cag cac atg gaa gac cct cgc cgt gca ggc aag atg ctg<br>Glu Ala Gly Gln His Met Glu Asp Pro Arg Arg Ala Gly Lys Met Leu<br>405 410 415 | | | 1424 |
| atg acg ctg ccg ctg ctg agg cag acc tcc acc aag gca gtc cag cac<br>Met Thr Leu Pro Leu Leu Arg Gln Thr Ser Thr Lys Ala Val Gln His<br>420 425 430 | | | 1472 |
| ttc tac aac atc aaa ctc gaa ggc aaa gtg ccc atg cac aaa ctt ttt<br>Phe Tyr Asn Ile Lys Leu Glu Gly Lys Val Pro Met His Lys Leu Phe<br>435 440 445 450 | | | 1520 |
| ttg gaa atg ctg gag gcc aag gtc tgactaaaag ccccccctgg gccctcccat<br>Leu Glu Met Leu Glu Ala Lys Val<br>455 | | | 1574 |
| cctgcacgtt gaaagggaa gataaaccca agaatgatgt cgaagaatct tagagtttag | | | 1634 |
| tgaacaacat taaaaatcaa cagactgcac tgatatttta gcagccacag tacgatgcag | | | 1694 |
| cctgcggatt ccgctacatc ttcctgatag gtttcctcta ctttatccca cgatcctctg | | | 1754 |
| gccacatccc tgcattcctc cactcttcct tgttctatta ttatgtttgg cttctttcac | | | 1814 |
| taatagttca ttttccctcc tcccctccct tctcttctcc ctcccctcctc tgtctccccc | | | 1874 |
| ttccttcctt tctcttcctt tccacaatct tctcctcttg ccttgctctc acctctcttc | | | 1934 |
| gctttctcac atctcctccc actctgcgta catagtcaat acctctgatt gtatggaaca | | | 1994 |
| tttctttac ctcttgcatc tcttctccgt ctccttcctc cccactttttt tttgtttgtt | | | 2054 |
| tgtttgtttc ctttccttcc ttctgctgct gaactcttaa tagcagtctc taactggaga | | | 2114 |

```
gagaaagaga gagagatgga agccagccct gccaaaggac agagatccat actatggatg    2174
ccagtgaact tgtcatgaac catgacatcc ccagtgagta aggaatcaaa gagagaaccg    2234
tacctaaagt acattgcaac gcaaacggat caacttagtg cagtattaga ttctaccggg    2294
cagccttcga tcagacaacc taagtggcgg cattggctgc ttctccttgc tttctcatct    2354
agatcagtta cagccatttg attccttaat tcttttgtca agtcttccag gtgttggtta    2414
gtttagctac tatgtaactt tttcagggaa tcctttaagc tttattcatt catgcaatac    2474
tagagagggg taaggatacc gcaacctcgt gctggctttg aacaattgaa cactaatgaa    2534
ggacaaatga accctgaagg aagattttta aaaatgtttc gtttcttctt acaaatggag    2594
atttttttgt accagcttta ccacttttca gccatttatt aatatgggga tttaacttac    2654
tcaagcaata gttgaaggga aggtgcatat taccacggat gcaatttatg ttgtgtgcca    2714
gtctggtccc aaacatcagt ttcttacatg agctccagtt tgcctaaatg ttcactgaca    2774
ccaaggatta gatgatacct gccgtgacac cgagtggtcc catccacgag cactgcacat    2834
gggatcccta tctgtagaat tagcaccagt acacctccct gccgggaggg acagtcgcca    2894
tacggtttct agctgccctc gtggttagga acaagatgct gcctgtatac aaactctgtc    2954
tcagaaggag ctgtgagcca ataccatttc agaggcaata aaggctaagt gccagaattc    3014
aaaccaacca accatcaaag acagcagacg cctgaccaaa ttctaaagtc ctgatccata    3074
ggagtcgatt cacttaggaa tggttgttta aattaacctg caggtttgtt ttgtttcctt    3134
gtttgttttt ttaccaaaag ctaagccaat agatgtgctt tttcaacaag tatggtcaca    3194
gcacgaaggt cagtcaggtt tcagactgta accaggtgta atctaatgaa gaaatcaaat    3254
gtcccctccc gaaacctaca gtcgccgaat aaccagaaac cagtaacctc cgtagaacgc    3314
tttaccaatg gaccagtgtt agtagctgct ctctgtattc tgtggacagt cttattctat    3374
gtacacagat gtaattaaag ttgtactcct aacaaacaaa agaatagttc agcttcaatg    3434
ttccatgttt gctgcgcttt tctgaacttt atgttgcatt cagaaactgt cgtcttgttc    3494
tcgtggtgtt tggattcttg tggtgtgtgc ttttagacac agggtagaat tagagacagt    3554
attggatgta tacttcctca ggagactaca gtagtatatt ctactcctta ccagtaataa    3614
ctaagagatt gaaactccaa aacagtattc attacgatca gacacacatc aaaatcataa    3674
taatattttc aaaaagggga taatttctct aatggtttat tatagaatac caatgtatag    3734
cttagacata aaactttgaa tattcaagaa tatagataag tctaattttt aaatgctgta    3794
tataaggctt ccacctgatc atctctcaga tgttgttatt aactcgctct gtgttgttgc    3854
aaaccttttt ggtgcggact tgcttccaaa actattgcta ctttgtgtgc gttaagcaaa    3914
ataccttgga ctgagggtgt ctcagccctg tgctaggaat actgtgtatc tatcattagc    3974
tatatgggaa tatatcgtag attgtggttc tcagtagaga aagtgactgt agtgtgactc    4034
taggtaaatc atcattagca attcattcgg atggtcaata acttgaaatt gatagctgtg    4094
ataagtttta aaaaattggc aaatccctga ctaaacatca acagaaaata caactcctgg    4154
gggggaaagg tgctcatcct gtaagattct ttcatcatgt aagtgtttga aacattactt    4214
tgcagaaggt ttatgcaggg tttaagttac taccgctcaa taatgctata tatacacaaa    4274
tggaatatag acaatgtatg tacccaccgt ttcactgagt cgcagagaag aatctgagct    4334
tcagaagcca gagcccacaa gtgatcaggt gagacagagg cacatttaag gaaggaggta    4394
caatgtgtag ttctccgttt aaaagacttg gccttttaaa acaacaaata tctcacaact    4454
```

```
atggtgaaaa caacaacagc ttcaagtgtg gatctaaagg aaacgcacag gtttagggta    4514
aataccattt gtaccttgct cgagcaaagt ttattgtttt gttttttttt gttttgtttt    4574
gttttgtttt caagtttcca gcaagaccgt ttagttaatg ccagctgtca ggaagatacc    4634
aaggtgtatg ttttagccat gcaatttgca gttttatttt cctttaggt ttgtccttat     4694 ttaaggcagt gcgattgttt tggcttcttg tagtgactct cgtgttttaa tcaagccaga    4754
ttgttgtatt tattccacta ttttgcattt aaatgatgac ataaaagata taaaaaattt    4814
aaaactgcta tttttcttat agaagagaaa atggatgttg gtgattgtat tttaattatt    4874
taagcatctc tgtttacctg cctgggacaa cattttatgg cagtcttatg tgcaaagatc    4934
gtgaatggac aaaacaaaaa attaaactgc ttacaatgat ccaggagttg cattatagcc    4994
agtagtaaaa ataataatga taattaataa taattaataa taataatgaa accatgtcta    5054
tagctgtagg tgggcatcac atctgtaaag caatcaattg tatattttg tgatgtgtac      5114 catactgtgt gctccagcaa atgtccattt gtgtaaatgt atttatttta tattgtatat    5174
attgttaaat gcaaaaagga gctatgattc tgtgactcca atcagttcag atatgtaact    5234
caaattatta tgccttcag gaggatggta gaacaatatt aaacaagctt ccactttaa      5294 aaaaaaaaaa aaaaaaaa                                                   5312
```

<210> SEQ ID NO 18
<211> LENGTH: 458
<212> TYPE: PRT
<213> ORGANISM: Mus musculus

<400> SEQUENCE: 18

Met Asp Ser Val Glu Leu Cys Leu Pro Glu Ser Phe Ser Leu His Tyr
1               5                   10                  15

Glu Glu Glu Leu Leu Cys Arg Met Ser Asn Lys Asp Arg His Ile Asp
            20                  25                  30

Ser Ser Cys Ser Ser Phe Ile Lys Thr Glu Pro Ser Ser Pro Ala Ser
        35                  40                  45

Leu Thr Asp Ser Val Asn His His Ser Pro Gly Gly Ser Ser Asp Ala
    50                  55                  60

Ser Gly Ser Tyr Ser Ser Thr Met Asn Gly His Gln Asn Gly Leu Asp
65                  70                  75                  80

Ser Pro Pro Leu Tyr Pro Ser Ala Pro Ile Leu Gly Gly Ser Gly Pro
                85                  90                  95

Val Arg Lys Leu Tyr Asp Asp Cys Ser Ser Thr Ile Val Glu Asp Pro
            100                 105                 110

Gln Thr Lys Cys Glu Tyr Met Leu Asn Ser Met Pro Lys Arg Leu Cys
        115                 120                 125

Leu Val Cys Gly Asp Ile Ala Ser Gly Tyr His Tyr Gly Val Ala Ser
    130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
        195                 200                 205

Lys Tyr Lys Arg Arg Ile Asp Ala Glu Asn Ser Pro Tyr Leu Asn Pro
    210                 215                 220

```
Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
            245                 250                 255

Val Pro Asp Ser Asp Ile Lys Ala Leu Thr Thr Leu Cys Asp Leu Ala
        260                 265                 270

Asp Arg Glu Leu Val Val Ile Ile Gly Trp Ala Lys His Ile Pro Gly
    275                 280                 285

Phe Ser Thr Leu Ser Leu Ala Asp Gln Met Ser Leu Leu Gln Ser Ala
290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Asp Tyr Ile Met Asp Glu Asp Gln
                325                 330                 335

Ser Lys Leu Ala Gly Leu Leu Asp Leu Asn Asn Ala Ile Leu Gln Leu
            340                 345                 350

Val Lys Lys Tyr Lys Ser Met Lys Leu Glu Lys Glu Glu Phe Val Thr
        355                 360                 365

Leu Lys Ala Ile Ala Leu Ala Asn Ser Asp Ser Met His Ile Glu Asp
    370                 375                 380

Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Arg Ala Gly Lys
                405                 410                 415

Met Leu Met Thr Leu Pro Leu Leu Arg Gln Thr Ser Thr Lys Ala Val
            420                 425                 430

Gln His Phe Tyr Asn Ile Lys Leu Glu Gly Lys Val Pro Met His Lys
        435                 440                 445

Leu Phe Leu Glu Met Leu Glu Ala Lys Val
    450                 455

<210> SEQ ID NO 19
<211> LENGTH: 5260
<212> TYPE: DNA
<213> ORGANISM: Homo sapiens
<220> FEATURE:
<221> NAME/KEY: CDS
<222> LOCATION: (174)..(1547)

<400> SEQUENCE: 19
aagctccaat cggggcttta agtccttgat taggagagtg tgagagcttt ggtcccaact      60
ggctgtgcct ataggcttgt cactaggaga acatttgtgt taattgcact gtgctctgtc     120
aaggaaactt tgatttatag ctggggtgca caataatgg ttgccggtcg cac atg         176
                                                           Met
                                                            1 gat tcg gta gaa ctt tgc ctt cct gaa tct ttt tcc ctg cac tac gag       224
Asp Ser Val Glu Leu Cys Leu Pro Glu Ser Phe Ser Leu His Tyr Glu
        5                  10                  15 gaa gag ctt ctc tgc aga atg tca aac aaa gat cga cac att gat tcc       272
Glu Glu Leu Leu Cys Arg Met Ser Asn Lys Asp Arg His Ile Asp Ser
     20                  25                  30 agc tgt tcg tcc ttc atc aag acg gaa cct tcc agc cca gcc tcc ctg       320
Ser Cys Ser Ser Phe Ile Lys Thr Glu Pro Ser Ser Pro Ala Ser Leu
 35                  40                  45 acg gac agc gtc aac cac cac agc cct ggt ggc tct tca gac gcc agt       368
Thr Asp Ser Val Asn His His Ser Pro Gly Gly Ser Ser Asp Ala Ser
```

```
              50                  55                  60                  65
ggg agc tac agt tca acc atg aat ggc cat cag aac gga ctt gac tcg        416
Gly Ser Tyr Ser Ser Thr Met Asn Gly His Gln Asn Gly Leu Asp Ser
                     70                  75                  80 cca cct ctc tac cct tct gct cct atc ctg gga ggt agt ggg cct gtc        464
Pro Pro Leu Tyr Pro Ser Ala Pro Ile Leu Gly Gly Ser Gly Pro Val
             85                  90                  95 agg aaa ctg tat gat gac tgc tcc agc acc att gtt gaa gat ccc cag        512
Arg Lys Leu Tyr Asp Asp Cys Ser Ser Thr Ile Val Glu Asp Pro Gln
         100                 105                 110 acc aag tgt gaa tac atg ctc aac tcg atg ccc aag aga ctg tgt tta        560
Thr Lys Cys Glu Tyr Met Leu Asn Ser Met Pro Lys Arg Leu Cys Leu
     115                 120                 125 gtg tgt ggt gac atc gct tct ggg tac cac tat ggg gta gca tca tgt        608
Val Cys Gly Asp Ile Ala Ser Gly Tyr His Tyr Gly Val Ala Ser Cys
130                 135                 140                 145 gaa gcc tgc aag gca ttc ttc aag agg aca att caa ggc aat ata gaa        656
Glu Ala Cys Lys Ala Phe Phe Lys Arg Thr Ile Gln Gly Asn Ile Glu
                150                 155                 160 tac agc tgc cct gcc acg aat gaa tgt gaa atc aca aag cgc aga cgt        704
Tyr Ser Cys Pro Ala Thr Asn Glu Cys Glu Ile Thr Lys Arg Arg Arg
            165                 170                 175 aaa tcc tgc cag gct tgc cgc ttc atg aag tgt tta aaa gtg ggc atg        752
Lys Ser Cys Gln Ala Cys Arg Phe Met Lys Cys Leu Lys Val Gly Met
        180                 185                 190 ctg aaa gaa ggg gtg cgt ctt gac aga gta cgt gga ggt cgg cag aag        800
Leu Lys Glu Gly Val Arg Leu Asp Arg Val Arg Gly Gly Arg Gln Lys
    195                 200                 205 tac aag cgc agg ata gat gcg gag aac agc cca tac ctg aac cct cag        848
Tyr Lys Arg Arg Ile Asp Ala Glu Asn Ser Pro Tyr Leu Asn Pro Gln
210                 215                 220                 225 ctg gtt cag cca gcc aaa aag cca tat aac aag att gtc tca cat ttg        896
Leu Val Gln Pro Ala Lys Lys Pro Tyr Asn Lys Ile Val Ser His Leu
                230                 235                 240 ttg gtg gct gaa ccg gag aag atc tat gcc atg cct gac cct act gtc        944
Leu Val Ala Glu Pro Glu Lys Ile Tyr Ala Met Pro Asp Pro Thr Val
            245                 250                 255 ccc gac agt gac atc aaa gcc ctc act aca ctg tgt gac ttg gcc gac        992
Pro Asp Ser Asp Ile Lys Ala Leu Thr Thr Leu Cys Asp Leu Ala Asp
        260                 265                 270 cga gag ttg gtg gtt atc att gga tgg gcg aag cat att cca ggc ttc       1040
Arg Glu Leu Val Val Ile Ile Gly Trp Ala Lys His Ile Pro Gly Phe
    275                 280                 285 tcc acg ctg tcc ctg gcg gac cag atg agc ctt ctg cag agt gct tgg       1088
Ser Thr Leu Ser Leu Ala Asp Gln Met Ser Leu Leu Gln Ser Ala Trp
290                 295                 300                 305 atg gaa att ttg atc ctt ggt gtc gta tac cgg tct ctt tcg ttt gag       1136
Met Glu Ile Leu Ile Leu Gly Val Val Tyr Arg Ser Leu Ser Phe Glu
                310                 315                 320 gat gaa ctt gtc tat gca gac gat tat ata atg gac gaa gac cag tcc       1184
Asp Glu Leu Val Tyr Ala Asp Asp Tyr Ile Met Asp Glu Asp Gln Ser
            325                 330                 335 aaa tta gca ggc ctt ctt gat cta aat aat gct atc ctg cag ctg gta       1232
Lys Leu Ala Gly Leu Leu Asp Leu Asn Asn Ala Ile Leu Gln Leu Val
        340                 345                 350 aag aaa tac aag agc atg aag ctg gaa aaa gaa gaa ttt gtc acc ctc       1280
Lys Lys Tyr Lys Ser Met Lys Leu Glu Lys Glu Glu Phe Val Thr Leu
    355                 360                 365 aaa gct ata gct ctt gct aat tca gac tcc atg cac ata gaa gat gtt       1328
```

-continued

| | | | | | | | | | | | | | | |
|---|---|---|---|---|---|---|---|---|---|---|---|---|---|---|
| Lys | Ala | Ile | Ala | Leu | Ala | Asn | Ser | Asp | Ser | Met | His | Ile | Glu | Asp | Val |
| 370 | | | | 375 | | | | | 380 | | | | | 385 | |

```
gaa gcc gtt cag aag ctt cag gat gtc tta cat gaa gcg ctg cag gat    1376
Glu Ala Val Gln Lys Leu Gln Asp Val Leu His Glu Ala Leu Gln Asp
            390                 395                 400 tat gaa gct ggc cag cac atg gaa gac cct cgt cga gct ggc aag atg    1424
Tyr Glu Ala Gly Gln His Met Glu Asp Pro Arg Arg Ala Gly Lys Met
        405                 410                 415 ctg atg aca ctg cca ctc ctg agg cag acc tct acc aag gcc gtg cag    1472
Leu Met Thr Leu Pro Leu Leu Arg Gln Thr Ser Thr Lys Ala Val Gln
420                 425                 430 cat ttc tac aac atc aaa cta gaa ggc aaa gtc cca atg cac aaa ctt    1520
His Phe Tyr Asn Ile Lys Leu Glu Gly Lys Val Pro Met His Lys Leu
    435                 440                 445 ttt ttg gaa atg ttg gag gcc aag gtc tgactaaaag ctccctgggc          1567
Phe Leu Glu Met Leu Glu Ala Lys Val
450                 455
```

| | |
|---|---|
| cttcccatcc ttcatgttga aaaagggaaa ataaacccaa gagtgatgtc gaagaaactt | 1627 |
| agagtttagt taacaacatc aaaaatcaac agactgcact gataatttag cagcaagact | 1687 |
| atgaagcagc tttcagattc ctccataggt tcctgatgag tttctttcta ctttctccat | 1747 |
| catcttcttt cctctttctt cccacatttc tctttctctt tatttttcct cctttctttc | 1807 |
| tttcacctcc cttatttctt tgcttctttc attcctagtt cccattctcc tttattttct | 1867 |
| tcccgtctgc ctgccttctt tcttttcttt acctactctc attcctctct tttctcatcc | 1927 |
| ttccccttt ttctaaattt gaaatagctt tagtttaaaa aaaaatcctc ccttcccct | 1987 |
| ttcctttccc tttctttcct ttttcccttt ccttttccct ttcctttcct ttcctcttga | 2047 |
| ccttctttcc atctttcttt ttcttccttc tgctgctgaa cttttaaaag aggtctctaa | 2107 |
| ctgaagagag atggaagcca gccctgccaa aggatggaga tccataatat ggatgccagt | 2167 |
| gaacttattg tgaaccatac tgtccccaat gactaaggaa tcaaagagag agaaccaacg | 2227 |
| ttcctaaaag tacagtgcaa catatacaaa ttgactgagt gcagtattag atttcatggg | 2287 |
| agcagcctct aattagacaa cttaagcaac gttgcatcgg ctgcttctta tcattgcttt | 2347 |
| tccatctaga tcagttacag ccatttgatt ccttaattgt ttttcaagt cttccaggta | 2407 |
| tttgttagtt tagctactat gtaacttttt cagggaatag tttaagcttt attcattcat | 2467 |
| gcaatactaa agagaaataa gaatactgca attttgtgct ggctttgaac aattacgaac | 2527 |
| aataatgaag gacaaatgaa tcctgaagga agatttttaa aaatgttttg tttcttctta | 2587 |
| caaatggaga tttttttgta ccagctttac cacttttcag ccatttatta atatgggaat | 2647 |
| ttaacttact caagcaatag ttgaagggaa ggtgcatatt atcacggatg caatttatgt | 2707 |
| tgtgtgccag tctggtccca aacatcaatt tcttaacatg agctccagtt tacctaaatg | 2767 |
| ttcactgaca caaaggatga gattacacct acagtgactc tgagtagtca catatataag | 2827 |
| cactgcacat gagatataga tccgtagaat tgtcaggagt gcacctctct acttgggagg | 2887 |
| tacaattgcc atatgatttc tagctgccat ggtggttagg aatgtgatac tgcctgtttg | 2947 |
| caaagtcaca gaccttgcct cagaaggagc tgtgagccag tattcattta agaggcaata | 3007 |
| aggcaaatgc cagaattaaa aaaaaaaatc atcaaagaca gaaaatgcct gaccaaattc | 3067 |
| taaaacctaa tccatataag tttattcatt taggaatgtt cgtttaaatt aatctgcagt | 3127 |
| ttttaccaag agctaagcca atatatgtgc ttttcaacca gtattgtcac agcatgaaag | 3187 |
| tcaagtcagg ttccagactg ttaagaggtg taatctaatg aagaaatcaa ttagatgccc | 3247 |

| | |
|---|---|
| cgaaatctac agtcgctgaa taaccaataa acagtaacct ccatcaaatg ctataccaat | 3307 |
| ggaccagtgt tagtagctgc tccctgtatt atgtgaacag tcttattcta tgtacacaga | 3367 |
| tgtaattaaa attgtaatcc taacaaacaa aagaaatgta gttcagcttt tcaatgtttc | 3427 |
| atgtttgctg tgcttttctg aattttatgt tgcattcaaa gactgttgtc ttgttcttgt | 3487 |
| ggtgtttgga ttcttgtggt gtgtgctttt agacacaggg tagaattaga gacaatattg | 3547 |
| gatgtacaat tcctcaggag actacagtag tatattctat tccttaccag taataaggtt | 3607 |
| cttcctaata ataattaaga gattgaaact ccaaacaagt attcattatg aacagataca | 3667 |
| catcaaaatc ataataatat tttcaaaaca aggaataatt tctctaatgg tttattatag | 3727 |
| aataccaatg tatagcttag aaataaaact ttgaatattt caagaatata gataagtcta | 3787 |
| atttttaaat gctgtatata tggctttcac tcaatcatct ctcagatgtt gttattaact | 3847 |
| cgctctgtgt tgttgcaaaa cttttggtg cagattcgtt tccaaaacta ttgctacttt | 3907 |
| gtgtgcttta aacaaaatac cttgggttga tgaaacatca acccagtgct aggaatactg | 3967 |
| tgtatctatc attagctata tgggactata ttgtagattg tggtttctca gtagagaagt | 4027 |
| gactgtagtg tgattctaga taaatcatca ttagcaattc attcagatgg tcaataactt | 4087 |
| gaaatttata gctgtgatag gagttcagaa attggcacat ccctttaaaa ataacaacag | 4147 |
| aaaatacaac tcctgggaaa aaaggtgctg attctataag attatttata tatgtaagtg | 4207 |
| tttaaaaaga ttattttcca gaaagtttgt gcagggttta agttgctact attcaactac | 4267 |
| actatatata aataaaatat atacaatata tacattgttt tcactgtatc acattaaagt | 4327 |
| acttgggctt cagaagtaag agccaaccaa ctgaaaacct gagatggaga tatgttcaaa | 4387 |
| gaatgagata caattttta gttttcagtt taagtaactc tcagcattac aaaagagtaa | 4447 |
| gtatctcaca aataggaaat aaaactaaaa cgtggattta aaaagaactg cacgggcttt | 4507 |
| agggtaaatg ctcatcttaa acctcactag agggaagtct tctcaagttt caagcaagac | 4567 |
| catttactta atgtgaagtt ttggaaagtt ataaaggtgt atgttttagc catatgattt | 4627 |
| taattttaat tttgcttctt ttaggttcgt tcttatttaa agcaatatga ttgtgtgact | 4687 |
| ccttgtagtt acacttgtgt ttcaatcaga tcagattgtt gtatttattc cactattttg | 4747 |
| catttaaatg ataacataaa agatataaaa aatttaaaac tgctattttt cttatagaag | 4807 |
| agaaaatggg tgttggtgat tgtatttta ttatttaagc gtctctgttt acctgcctag | 4867 |
| gaaaacattt tatggcagtc ttatgtgcaa agatcgtaaa aggacaaaaa atttaaactg | 4927 |
| cttataataa tccaggagtt gcattatagc cagtagtaaa aataataata ataataataa | 4987 |
| aaccatgtct atagctgtag atgggcttca catctgtaaa gcaatcaatt gtatattttt | 5047 |
| gtgatgtgta ccatactgtg tgctccagca aatgtccatt tgtgtaaatg tatttatttt | 5107 |
| atattgtata tattgttaaa tgcaaaaagg agatatgatt ctgtaactcc aatcagttca | 5167 |
| gatgtgtaac tcaaattatt atgcctttca ggatgatggt agagcaatat taaacaagct | 5227 |
| tccactttg actgctaaaa aaaaaaaaa aaa | 5260 |

<210> SEQ ID NO 20
<211> LENGTH: 458
<212> TYPE: PRT
<213> ORGANISM: Homo sapiens

<400> SEQUENCE: 20

```
Met Asp Ser Val Glu Leu Cys Leu Pro Glu Ser Phe Ser Leu His Tyr
1               5                   10                  15
```

```
Glu Glu Glu Leu Leu Cys Arg Met Ser Asn Lys Asp Arg His Ile Asp
             20                  25                  30

Ser Ser Cys Ser Ser Phe Ile Lys Thr Glu Pro Ser Ser Pro Ala Ser
         35                  40                  45

Leu Thr Asp Ser Val Asn His His Ser Pro Gly Gly Ser Ser Asp Ala
     50                  55                  60

Ser Gly Ser Tyr Ser Ser Thr Met Asn Gly His Gln Asn Gly Leu Asp
 65                  70                  75                  80

Ser Pro Pro Leu Tyr Pro Ser Ala Pro Ile Leu Gly Gly Ser Gly Pro
                 85                  90                  95

Val Arg Lys Leu Tyr Asp Asp Cys Ser Ser Thr Ile Val Glu Asp Pro
                100                 105                 110

Gln Thr Lys Cys Glu Tyr Met Leu Asn Ser Met Pro Lys Arg Leu Cys
            115                 120                 125

Leu Val Cys Gly Asp Ile Ala Ser Gly Tyr His Tyr Gly Val Ala Ser
        130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
        195                 200                 205

Lys Tyr Lys Arg Arg Ile Asp Ala Glu Asn Ser Pro Tyr Leu Asn Pro
210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270

Asp Arg Glu Leu Val Val Ile Ile Gly Trp Ala Lys His Ile Pro Gly
        275                 280                 285

Phe Ser Thr Leu Ser Leu Ala Asp Gln Met Ser Leu Leu Gln Ser Ala
    290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Asp Tyr Ile Met Asp Glu Asp Gln
                325                 330                 335

Ser Lys Leu Ala Gly Leu Leu Asp Leu Asn Asn Ala Ile Leu Gln Leu
            340                 345                 350

Val Lys Lys Tyr Lys Ser Met Lys Leu Glu Lys Glu Glu Phe Val Thr
        355                 360                 365

Leu Lys Ala Ile Ala Leu Ala Asn Ser Asp Ser Met His Ile Glu Asp
    370                 375                 380

Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Arg Ala Gly Lys
                405                 410                 415

Met Leu Met Thr Leu Pro Leu Leu Arg Gln Thr Ser Thr Lys Ala Val
            420                 425                 430

Gln His Phe Tyr Asn Ile Lys Leu Glu Gly Lys Val Pro Met His Lys
```

```
                435                 440                 445
Leu Phe Leu Glu Met Leu Glu Ala Lys Val
    450                 455
```

<210> SEQ ID NO 21
<211> LENGTH: 4733
<212> TYPE: DNA
<213> ORGANISM: Homo sapiens

<400> SEQUENCE: 21

```
aactggagga cccgtgcttg taagtgctcc cataagccca gaagagcaag ataaacttga      60
aaataagctc aagcagacaa atctccagtg gataaaggtt tccagagctt tacctgagaa     120
acaaggagaa attgaagctc aaataaaaga ccttgggcag cttgaaaaaa gcttgaaga     180
ccttgaagag cagttaaatc atctgctgct gtggttatct cctattagga atcagttgga     240
aatttataac caaccaaacc aagaaggacc atttgacgtt aaggaaactg aaatagcagt     300
tcaagctaaa caaccggatg tggaagagat tttgtctaaa gggcagcatt tgtacaagga     360
aaaaccagcc actcagccag tgaagaggaa gttagaagat ctgagctctg agtggaaggc     420
ggtaaaccgt ttacttcaag agctgagggc aaagcagcct gacctagctc ctggactgac     480
cactattgga gcctctccta ctcagactgt tactctggtg acacaacctg tggttactaa     540
ggaaactgcc atctccaaac tagaaatgcc atcttccttg atgttggagg tacctgctct     600
ggcagatttc aaccgggctt ggacagaact taccgactgg ctttctctgc ttgatcaagt     660
tataaaatca cagagggtga tggtgggtga ccttgaggat atcaacgaga tgatcatcaa     720
gcagaaggca acaatgcagg atttggaaca gaggcgtccc cagttggaag aactcattac     780
cgctgcccaa aatttgaaaa acaagaccag caatcaagag ctagaacaa tcattacgga     840
tcgaattgaa agaattcaga atcagtggga tgaagtacaa gaacaccttc agaaccggag     900
gcaacagttg aacgaaatgt taaaggattc aacacaatgg ctggaagcta aggaagaagc     960
tgagcaggtc ttaggacagg ccagagccaa gcttgagtca tggaaggagg gtccctatac    1020
agtagatgca atccaaaaga aaatcacaga aaccaagcag ttggccaaag acctccgcca    1080
gtggcagaca aatgtagatg tggcaaatga cttggccctg aaacttctcc gggattattc    1140
tgcagatgat accagaaaag tccacatgat aacagagaat atcaatgcct cttggagaag    1200
cattcataaa agggtgagtg agcgagaggc tgctttggaa gaaactcata gattactgca    1260
acagttcccc ctggacctgg aaaagttttct tgcctggctt acagaagctg aaacaactgc    1320
caatgtccta caggatgcta cccgtaagga aaggctccta gaagactcca agggagtaaa    1380
agagctgatg aaacaatggc aagacctcca aggtgaaatt gaagctcaca cagatgttta    1440
tcacaacctg gatgaaaaca gccaaaaaat cctgagatcc ctggaaggtt ccgatgatgc    1500
agtcctgtta caaagacgtt tggataacat gaacttcaag tggagtgaac ttcggaaaaa    1560
gtctctcaac attaggtccc atttggaagc agttctgac cagtggaagc gtctgcacct    1620
ttctctgcag gaacttctgg tgtggctaca gctgaaagat gatgaattaa gccggcaggc    1680
acctattgga ggcgactttc cagcagttca gaagcagaac gatgtacata gggccttcaa    1740
gagggaattg aaaactaaag aacctgtaat catgagtact cttgagactg tacgaatatt    1800
tctgacagag cagcctttgg aaggactaga gaaactctac caggagccca gagagctgcc    1860
tcctgaggag agagcccaga atgtcactcg gcttctacga aagcaggctg aggaggtcaa    1920
tactgagtgg gaaaaattga acctgcactc cgctgactgg cagagaaaaa tagatgagac    1980
```

```
ccttgaaaga ctccaggaac ttcaagaggc cacggatgag ctggacctca agctgcgcca    2040
agctgaggtg atcaagggat cctggcagcc cgtgggcgat ctcctcattg actctctcca    2100
agatcacctc gagaaagtca aggcacttcg aggagaaatt gcgcctctga agagaacgt    2160 gagccacgtc aatgaccttg ctcgccagct taccactttg ggcattcagc tctcaccgta    2220
taacctcagc actctggaag acctgaacac cagatggaag cttctgcagg tggccgtcga    2280
ggaccgagtc aggcagctgc atgaagccca cagggacttt ggtccagcat ctcagcactt    2340
tctttccacg tctgtccagg gtccctggga gagagccatc tcgccaaaca aagtgcccta    2400
ctatatcaac cacgagactc aaacaacttg ctgggaccat cccaaaatga cagagctcta    2460 ccagtctttta gctgacctga ataatgtcag attctcagct tataggactg ccatgaaact    2520
ccgaagactg cagaaggccc tttgcttgga tctcttgagc ctgtcagctg catgtgatgc    2580
cttggaccag cacaacctca gcaaaaatga ccagcccatg gatatcctgc agattattaa    2640
ttgtttgacc actatttatg accgcctgga gcaagagcac aacaatttgg tcaacgtccc    2700
tctctgcgtg gatatgtgtc tgaactggct gctgaatgtt tatgatacgg gacgaacagg    2760
gaggatccgt gtcctgtctt ttaaaactgg catcatttcc ctgtgtaaag cacatttgga    2820
agacaagtac agatacctt tcaagcaagt ggcaagttca acaggatttt gtgaccagcg    2880
caggctgggc ctccttctgc atgattctat ccaaattcca agacagttgg gtgaagttgc    2940
atcctttggg ggcagtaaca ttgagccaag tgtccggagc tgcttccaat ttgctaataa    3000
taagccagag atcgaagcgg ccctcttcct agactggatg agactggaac cccagtccat    3060
ggtgtggctg cccgtcctgc acagagtggc tgctgcagaa actgccaagc atcaggccaa    3120
atgtaacatc tgcaaagagt gtccaatcat tggattcagg tacaggagtc taaagcactt    3180
taattatgac atctgccaaa gctgctttttt ttctggtcga gttgcaaaag gccataaaat    3240
gcactatccc atggtggaat attgcactcc gactacatca ggagaagatg ttcgagactt    3300
tgccaaggta ctaaaaaaca aatttcgaac caaaaggtat tttgcgaagc atccccgaat    3360
gggctacctg ccagtgcaga ctgtcttaga gggggacaac atggaaactc ccgttactct    3420
gatcaacttc tggccagtag attctgcgcc tgcctcgtcc cctcagcttt cacacgatga    3480
tactcattca cgcattgaac attatgctag caggctagca gaaatggaaa acagcaatgg    3540
atcttatcta aatgatagca tctctcctaa tgagagcata gatgatgaac atttgttaat    3600
ccagcattac tgccaaagtt tgaaccagga ctccccctg agccagcctc gtagtcctgc    3660
ccagatcttg atttccttag agagtgagga aagaggggag ctagagagaa tcctagcaga    3720
tcttgaggaa gaaaacagga atctgcaagc agaatatgac cgtctaaagc agcagcacga    3780
acataaaggc ctgtccccac tgccgtcccc tcctgaaatg atgcccacct ctccccagag    3840
tccccgggat gctgagctca ttgctgaggc caagctactg cgtcaacaca aaggccgcct    3900
ggaagccagg atgcaaatcc tggaagacca caataaacag ctggagtcac agttacacag    3960
gctaaggcag ctgctggagc aaccccaggc agaggccaaa gtgaatggca caacggtgtc    4020
ctctccttct acctctctac agaggtccga cagcagtcag cctatgctgc tccgagtggt    4080
tggcagtcaa acttcggact ccatgggtga ggaagatctt tcagtcctc cccaggacac    4140 aagcacaggg ttagaggagg tgatggagca actcaacaac tccttcccta gttcaagagg    4200
acacaatgta ggaagtcttt tccacatggc agatgatttg ggcagagcga tggagtcctt    4260
agtatcagtc atgacagatg aagaaggagc agaataaatg ttttacaact cctgattccc    4320
gcatggtttt tataatattc atacaacaaa gaggattaga cagtaagagt ttacaagaaa    4380
```

```
taaatctata tttttgtgaa gggtagtggt attatactgt agatttcagt agtttctaag    4440
tctgttattg ttttgttaac aatggcaggt tttacacgtc tatgcaattg tacaaaaaag    4500
ttataagaaa actacatgta aaatcttgat agctaaataa cttgccattt ctttatatgg    4560
aacgcatttt gggttgttta aaaatttata acagttataa agaaagattg taaactaaag    4620
tgtgctttat aaaaaaaagt tgtttataaa aacccctaaa aacaaaacaa acacacacac    4680
acacacatac acacacacac acaaaacttt gaggcagcgc attgttttgc atc           4733
```

METHOD FOR INDUCING DIFFERENTIATION OF PLURIPOTENT STEM CELLS INTO SKELETAL MUSCLE OR SKELETAL MUSCLE PROGENITOR CELLS

TECHNICAL FIELD

The present invention relates to a method for inducing differentiation of pluripotent stem cells into skeletal muscle or skeletal muscle progenitor cells.

The present invention also relates to artificial skeletal muscle or skeletal muscle progenitor cells prepared by the above method.

BACKGROUND ART

Cells having pluripotency such as embryonic stem cells (ES cells) or induced pluripotent stem cells (iPS cells) obtained via introduction of undifferentiated cell-specific genes into somatic cells have been reported (U.S. Pat. No. 5,843,780 or WO 2007/069666). Hence, as a method for treating myogenic diseases, and particularly, a method for treating muscular dystrophy, a therapeutic method involving transplanting skeletal muscle progenitor cells resulting from induction of the differentiation of pluripotent stem cells has recently received attention. Similarly, development of a therapeutic agent using homogenous skeletal muscle is also under consideration.

Here, methods for inducing the differentiation of ES cells into skeletal muscle progenitor cells or skeletal muscle have been developed as follows: (1) a method that involves proliferating a single human ES cell by suspension culture, culturing the resulting cells by adhesion culture in a serum free culture solution, isolating CD73 positive cells, further culturing the cells, isolating NCAM positive cells, and proliferating the cells (Barberi T, et al. Nat Med. 13: 642-8, 2007); and (2) a method that involves treating human ES cells with 5-Aza-cytidine (demethylating agent), culturing the treated human ES cells by suspension culture to form embryoid bodies, and then further carrying out adhesion culture (Zheng JK, et al. Cell Res. 16:713-22, 2006), for example.

However, these methods are problematic in that: it is necessary to isolate cells several times and although engraftment of induced skeletal muscle can be confirmed by transplantation into model mice, the resulting amount of the skeletal muscle is extremely low.

DISCLOSURE OF THE INVENTION

Problem to be Solved by the Invention

One object of the present invention is to provide a method for inducing the differentiation of pluripotent stem cells into skeletal muscle or skeletal muscle progenitor cells by the steps of suspension culture, adhesion culture, and dissociation-adhesion culture.

Means for Solving the Problem

The present invention has the following characteristics.
[1] A method for producing artificial skeletal muscle or skeletal muscle progenitor cells from human pluripotent stem cells, comprising the following steps of:
(1) culturing human pluripotent stem cells by suspension culture,
(2) culturing a cell population after suspension culture by adhesion culture,
(3) dissociating cells after adhesion culture; and
(4) culturing dissociated cells by adhesion culture.
[2] The method according to [1], wherein in step (1) above, human pluripotent stem cells are cells of colonies formed by adhesion culture and the colonies are directly subjected to suspension culture.
[3] The method according to [1] or [2], wherein in step (2) above, cells are cultured in a serum free medium containing insulin, transferrin, and sodium selenite.
[4] The method according to any one of [1] to [3], wherein in step (4) above, dissociated cells are cultured at an initial density of 1,000-3,000 cells/cm$^2$.
[5] The method according to any one of [1] to [4], wherein in step (4) above, cells are cultured in a medium containing fetal calf serum and horse serum.
[6] The method according to any one of [1] to [5], wherein in step (1) above, the culture period is 7 days.
[7] The method according to any one of [1] to [6], wherein in step (2) above, the culture period is 14 days.
[8] The method according to any one of [1] to [7], wherein in step (4) above, the culture period is at least 21 days.
[9] The method according to [5], wherein in step (4) above, after the above culture in a medium containing the fetal calf serum and horse serum, the medium is exchanged with a serum free medium containing insulin, transferrin, and sodium selenite, and then cells are further cultured.
[10] The method according to any one of [1] to [9], wherein the human pluripotent stem cells are human embryonic stem (ES) cells or human induced pluripotent stem (iPS) cells.
[11] A kit for producing skeletal muscle or skeletal muscle progenitor cells from human pluripotent stem cells, containing with instructions the following substances:
(1) a serum free medium containing insulin, transferrin, and sodium selenite;
(2) a medium containing fetal calf serum and horse serum; and
(3) a cell dissociation solution.
[12] Artificial skeletal muscle or skeletal muscle progenitor cells, which are prepared from human pluripotent stem cells by the method according to any one of [1] to [10].
[13] The artificial skeletal muscle or skeletal muscle progenitor cells according to [12], containing DNA encoding normal human dystrophin in a form that can be expressed.
[14] Use of the artificial skeletal muscle or skeletal muscle progenitor cells prepared from human pluripotent stem cells by the method according to any one of [1] to [10] in preparation of a medicament for treating a myogenic disease.
[15] Composition comprising the artificial skeletal muscle or skeletal muscle progenitor cells prepared from human pluripotent stem cells by the method according to any one of [1] to [10].

The contents as disclosed in the description and/or drawings of U.S. Provisional Patent Application No. 61/326,929, to which the present application claims priority, are incorporated herein.

Effect of the Invention

Artificial skeletal muscle or skeletal muscle progenitor cells can be prepared by the method according to the present invention.

BRIEF DESCRIPTION OF DRAWINGS

In FIG. 2, open arrowheads indicate myogenin positive cell nuclei and white arrowheads indicate myosin-positive cells.

EMBODIMENTS FOR CARRYING OUT THE INVENTION

Figure 1:
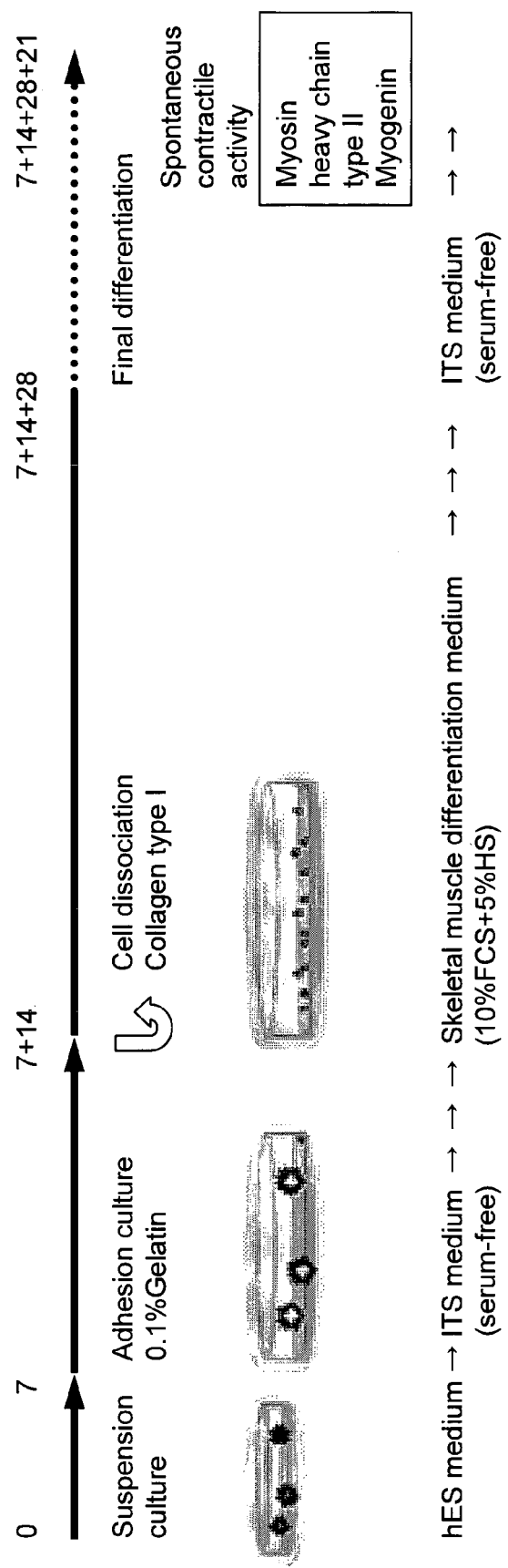
FIG. 1 shows a scheme for culturing, by which skeletal muscle or skeletal muscle progenitor cells are prepared from human pluripotent stem cells.

Hereinafter, the present invention will be described in detail.

The present invention relates to a method for inducing the differentiation of skeletal muscle or skeletal muscle progenitor cells, comprising culturing human pluripotent stem cells by suspension culture, adhesion culture, and then adhesion culture again after dissociation.

<Pluripotent Stem Cells>

Pluripotent stem cells that can be used in the present invention are stem cells having both pluripotency, by which the cells are capable of differentiating into all cells existing in vivo, and proliferation potency. Examples of these pluripotent stem cells include, but are not limited to, embryonic stem (ES) cells, embryonic stem (nuclear transfer ES: ntES) cells from clone embryos obtained by nuclear transplantation, spermatogonial stem cells ("germline stem cells: GS cells"), embryonic germ cells ("EG cells"), and induced pluripotent stem (iPS) cells. Examples of preferable pluripotent stem cells include ES cells, ntES cells, and iPS cells.

(A) Embryonic Stem Cells

ES cells are stem cells having pluripotency and proliferation potency via self-replication, which are established from inner cell mass of early embryos (e.g., blastocysts) of a mammal such as a human or a mouse.

ES cells are stem cells from embryos originated from inner cell mass of blastocysts that are embryos after the morula stage of fertilized eggs. ES cells have so-called pluripotency, by which they are capable of differentiating into all cells composing an adult, and proliferation potency via self-replication. ES cells were discovered in mice in 1981 (M. J. Evans and M. H. Kaufman (1981), Nature 292: 154-156). Thereafter, ES cell lines were also established in primates including humans, monkeys, and the like (J. A. Thomson et al. (1999), Science 282:1145-1147; J. A. Thomson et al. (1995), Proc. Natl. Acad. Sci. U.S.A., 92:7844-7848; J. A. Thomson et al. (1996), Biol. Reprod., 55: 254-259; J. A. Thomson and V. S. Marshall (1998), Curr. Top. Dev. Biol., 38: 133-165).

ES cells can be established by removing inner cell mass from blastocysts of fertilized eggs of a subject animal and then culturing the inner cell mass on fibroblasts as feeders. Also, cell maintenance by subculture can be carried out using a medium supplemented with substances such as a leukemia inhibitory factor (LIF) and a basic fibroblast growth factor (bFGF). Methods for establishment and maintenance of human and monkey ES cells are described in H. Suemori et al. (2006), Biochem. Biophys. Res. Commun., 345: 926-932; M. Ueno et al. (2006), Proc. Natl. Acad. Sci. U.S.A., 103: 9554-9559; H. Suemori et al. (2001), Dev. Dyn., 222: 273-279; and H. Kawasaki et al. (2002), Proc. Natl. Acad. Sci. U.S.A., 99: 1580-1585, for example.

As a medium for preparation of ES cells, a DMEM/F-12 medium supplemented with 0.1 mM 2-mercaptoethanol, 0.1 mM nonessential amino acid, 2 mM L-glutamic acid, 20% KSR, and 4 ng/ml l3-FGF is used, for example. Human ES cells can be maintained under wet atmosphere of 2% $CO_2$/98% air at 37° C. (O. Fumitaka et al. (2008), Nat. Biotechnol., 26: 215-224). Also, it is necessary for ES cells to subculture every 3 to 4 days. At this time, subculture can be carried out using 0.25% trypsin and 0.1 mg/ml collagenase IV in PBS containing 1 mM $CaCl_2$ and 20% KSR, for example.

ES cells can be generally selected by using the expression of a gene marker such as alkaline phosphatase, Oct-3/4 and Nanog as an index. The markers can be detected by Real-time PCR, western-blotting, immunostaining and so on. In particular, for selection of human ES cells, the expression of a gene marker such as OCT-3/4, NANOG and ECAD can be used as an index (E. Kroon et al. (2008), Nat. Biotechnol., 26: 443-452).

Human ES cell lines, such as KhES-1, KhES-2, and KhES-3 are available from the Institute for Frontier Medical Sciences, Kyoto University (Kyoto, Japan).

(B) Spermatogonial Stem Cells

Spermatogonial stem cells are testis-derived pluripotent stem cells, serving as an origin for spermatogenesis. Spermatogonial stem cells can also be induced to differentiate into cells of various lines in a manner similar to that in ES cells. For example, the cells have properties such that a chimeric mouse can be produced when transplanted into mouse blastocysts (M. Kanatsu-Shinohara et al. (2003) Biol. Reprod., 69: 612-616; K. Shinohara et al. (2004), Cell, 119: 1001-1012). Spermatogonial stem cells are self-replicable in a medium containing a glial cell line-derived neurotrophic factor (GDNF) or spermatogonial stem cells can be obtained by repeated subculture of the cells under culture conditions similar to those for ES cells (Masanori Takebayashi et al., (2008), Experimental Medicine, Vol. 26, No. 5 (Extra Number), pp. 41-46, YODOSHA (Tokyo, Japan)).

(C) Embryonic Germ Cells

Embryonic germ cells are cells established from primordial germ cells at the prenatal period and have pluripotency similar to that of ES cells. Embryonic germ cells can be established by culturing primordial germ cells in the presence of substances such as LIF, bFGF, and a stem cell factor (Y. Matsui et al. (1992), Cell, 70: 841-847; J.L. Resnick et al. (1992), Nature, 359: 550-551).

(D) Induced Pluripotent Stem Cells

Induced pluripotent stem (iPS) cells can be prepared by introducing a specific nuclear reprogramming substance in the form of DNA or protein into somatic cells. iPS cells are somatic cell-derived artificial stem cells having properties almost equivalent to those of ES cells, such as pluripotency and proliferation potency via self-replication (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; international publication WO 2007/069666). A nuclear reprogramming substance may be a gene specifically expressed in ES cells, a gene playing an important role in maintenance of undifferentiation of ES cells, or a gene product thereof. Examples of such nuclear reprogramming substance include, but are not particularly limited to, Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, and Esrrg. These reprogramming substances may be used in combination upon establishment of iPS cells. Such combination may contain at least one, two, or three reprogramming substances above and preferably contains four reprogramming substances above.

The nucleotide sequence information of the mouse or human cDNA of each of the above nuclear reprogramming substances and the amino acid sequence information of a protein encoded by the cDNA can be obtained by referring to NCBI accession numbers described in WO 2007/069666. Also, the mouse and human cDNA sequence and amino acid sequence information of L-Myc, Lin28, Lin28b, Esrrb, and Esrrg can be each obtained by referring to the following NCBI accession numbers. A person skilled in the art can prepare desired nuclear reprogramming substances by a conventional technique based on the cDNA sequence or amino acid sequence information.

FLAG. Also, in order to cleave a gene encoding a nuclear reprogramming substance, or a promoter and a gene encoding a nuclear reprogramming substance binding thereto together after introduction into somatic cells, the above vector may have LoxP sequences located before and after the relevant portion. In another preferable embodiment, a method that involves incorporating a transgene into a chromosome using a transposon, causing transferase to act on cells using a plasmid vector or an adenovirus vector, and then completely removing the transgene from the chromosome can be used. An example of a preferable transposon is piggyBac that is a lepidopteran insect-derived transposon (Kaji, K. et al., Nature, 458: 771-775 (2009), Woltjen et al., Nature, 458: 766-770 (2009), WO 2010/012077). Furthermore, a vector may also contain sequences of replication origins for lymphotrophic herpes virus, BK virus, and Bovine papilloma virus and sequences of replication factor thereof, so that the vector is replicated without incorporation into a chromosome so as to be present episomally. For example, EBNA-1 and oriP, or Large T and SV40ori sequences may be contained

| Gene Name | Mouse | | Human | |
|---|---|---|---|---|
| L-Myc | NM_008506 | (SEQ ID NOS: 1 and 2) | NM_001033081 | (SEQ ID NOS: 3 and 4) |
| Lin28 | NM_145833 | (SEQ ID NOS: 5 and 6) | NM_024674 | (SEQ ID NOS: 7 and 8) |
| Lin28b | NM_001031772 | (SEQ ID NOS: 9 and 10) | NM_001004317 | (SEQ ID NOS: 11 and 12) |
| Esrrb | NM_011934 | (SEQ ID NOS: 13 and 14) | NM_004452 | (SEQ ID NOS: 15 and 16) |
| Esrrg | NM_011935 | (SEQ ID NOS: 17 and 18) | NM_001438 | (SEQ ID NOS: 19 and 20) |

These nuclear reprogramming substances may be introduced in the form of protein into somatic cells by a technique such as lipofection, binding with a cell membrane-permeable peptide, or microinjection. Alternatively, they can also be introduced in the form of DNA or RNA into somatic cells by a technique such as a technique using a vector (such as a virus, a plasmid and an artificial chromosome), lipofection, a liposome, or microinjection. Examples of a viral vector include a retrovirus vector, a lentivirus vector (these are according to Cell, 126, pp. 663-676, 2006; Cell, 131, pp. 861-872, 2007; and Science, 318, pp. 1917-1920, 2007), an adenovirus vector (Science, 322, 945-949, 2008), an adeno-associated virus vector, and a Sendai virus vector (Proc Jpn Acad Ser B Phys Biol Sci. 85, 348-62, 2009). Also, examples of an artificial chromosome vector include a human artificial chromosome (HAC), a yeast artificial chromosome (YAC), and a bacterial artificial chromosome (BAC and PAC). As a plasmid, a plasmid for mammalian cells can be used (Science, 322: 949-953, 2008). A vector can contain regulatory sequences such as a promoter, an enhancer, a ribosome binding sequence, a terminator, and a polyadenylation site, so that a nuclear reprogramming substance can be expressed. Examples of a promoter to be used herein include an EF 1 a promoter, a CAG promoter, an SRα promoter, an SV40 promoter, an LTR promoter, a CMV (cytomegalovirus) promoter, an RSV (Rous sarcoma virus) promoter, MoMuLV (Moloney murine leukemia virus) LTR, and an HSV-TK (herpes simplex virus thymidine kinase) promoter. Particularly preferable examples of such a promoter include an EF1α promoter, a CAG promoter, MoMuLV LTR, a CMV promoter, and an SRα promoter. The above vector may further contain, if necessary, a selection marker sequence such as a drug resistance gene (e.g., a kanamycin resistance gene, an ampicillin resistance gene, and a puromycin resistance gene), a thymidine kinase gene, and a diphtheria toxin gene, and a reporter gene sequence such as a green fluorescent protein (GFP), β glucuronidase (GUS), and (WO 2009/115295, WO 2009/157201, and WO 2009/149233). Also, for simultaneous introduction of a plurality of nuclear reprogramming substances, an expression vector that enables polycistronic expression may be used. For polycistronic expression, sequences encoding nuclear reprogramming substances may be linked via an IRES or a foot and mouth disease virus (FMDV) 2A coding region (Science, 322: 949-953, 2008, WO 2009/092042 and WO 2009/152529).

Upon nuclear reprogramming, to improve the efficiency for inducing iPS cells, in addition to the above factors, histone deacetylase (HDAC) inhibitors [e.g., low-molecular-weight inhibitors such as valproic acid (VPA) (Nat. Biotechnol., 26(7): 795-797 (2008)), trichostatin A, sodium butyrate, MC 1293, and M344, and nucleic acid expression inhibitors such as siRNA and shRNA against HDAC (e.g., HDAC1 siRNA Smartpool® (Millipore) and HuSH 29mer shRNA Constructs against HDAC1 (OriGene)], DNA methyltransferase inhibitors (e.g., 5'-azacytidine) (Nat. Biotechnol., 26(7): 795-797 (2008)), G9a histone methyltransferase inhibitors [e.g., low-molecular-weight inhibitors such as BIX-01294 (Cell Stem Cell, 2: 525-528 (2008)) and nucleic acid expression inhibitors such as siRNA and shRNA against G9a (e.g., G9a siRNA (human) (Santa Cruz Biotechnology))], L-channel calcium agonists (e.g., Bayk8644) (Cell Stem Cell, 3, 568-574 (2008)), p53 inhibitors (e.g., siRNA and shRNA against p53) (Cell Stem Cell, 3, 475-479 (2008)), Wnt Signaling activator (e.g., soluble Wnt3a) (Cell Stem Cell, 3, 132-135 (2008)), cytokines such as LIF or bFGF, ALK5 inhibitors (e.g., SB431542) (Nat Methods, 6: 805-8 (2009)), mitogen-activated protein kinase signalling inhibitors, glycogen synthase kinase-3 inhibitors (PloS Biology, 6(10), 2237-2247 (2008)), miRNA such as miR-291-3p, miR-294, and miR-295 (R. L. Judson et al., Nat. Biotech., 27: 459-461 (2009)), for example, can be used.

Examples of a culture medium for inducing iPS cells include (1) DMEM, DMEM/F12, or a DME medium containing 10-15% FBS (these media may further appropriately contain LIF, penicillin/streptomycin, L-glutamine, nonessential amino acids, β-mercaptoethanol, and the like), (2) a medium for ES cell culture containing bFGF or SCF, such as a medium for mouse ES cell culture (e.g., TX-WES medium (Thromb-X)), and a medium for primate ES cell culture (e.g., a medium for primate (human & monkey) ES cells, ReproCELL, Kyoto, Japan).

An example of culture methods is as follows. Somatic cells are brought into contact with nuclear reprogramming substances (DNA, RNA or protein) on a DMEM or DMEM/F12 medium containing 10% FBS at 37° C. in the presence of 5% $CO_2$ and are cultured for about 4 to 7 days. Subsequently, the cells are reseeded on feeder cells (e.g., mitomycin C-treated STO cells or SNL cells). About 10 days after contact between the somatic cells and the nuclear reprogramming substances, cells are cultured in a bFGF-containing medium for primate ES cell culture. After about 30 to about 45 days or more of the contact, iPS cell-like colonies can be formed. Cells may also be cultured under conditions in which the oxygen concentration is as low as 5%-10% in order to increase the efficiency for inducing iPS cells.

Alternatively, cells may be cultured using DMEM containing 10% FBS (which may further appropriately contain LIF, penicillin/streptomycin, L-glutamine, nonessential amino acids, β-mercaptoethanol, and the like) on feeder cells (e.g., mitomycin C-treated STO cells or SNL cells). After about 25 to about 30 days or more of such culture, ES cell-like colonies can be formed.

During the above culture, medium exchange with a fresh medium is performed once a day from day 2 after the start of culture. In addition, the number of somatic cells to be used for nuclear reprogramming is not limited, but ranges from about $5 \times 10^3$ to about $5 \times 10^6$ cells per culture dish (100 cm$^2$).

When a gene including a drug resistance gene is used as a marker gene, cells expressing the marker gene can be selected by culturing the cells in a medium (selective medium) containing the relevant drug. Also, cells expressing the marker gene can be detected when the marker gene is a fluorescent protein gene, through observation with a fluorescence microscope, by adding a luminescent substrate in the case of a luminescent enzyme gene, or adding a chromogenic substrate in the case of a chromogenic enzyme gene.

The term "somatic cells" as used herein may refer to any cells other than germ cells from mammals (e.g., humans, mice, monkeys, pigs, and rats). Examples of such somatic cells include keratinizing epithelial cells (e.g., keratinizing epidermal cells), mucosal epithelial cells (e.g., epithelial cells of the surface layer of tongue), exocrine epithelial cells (e.g., mammary glandular cells), hormone-secreting cells (e.g., adrenal medullary cells), cells for metabolism and storage (e.g., hepatocytes), boundary-forming luminal epithelial cells (e.g., type I alveolar cells), luminal epithelial cells of internal tubules (e.g., vascular endothelial cells), ciliated cells having carrying capacity (e.g., airway epithelial cells), cells for secretion of extracellular matrix (e.g., fibroblasts), contractile cells (e.g., smooth muscle cells), cells of blood and immune system (e.g., T lymphocytes), cells involved in sensation (e.g., rod cells), autonomic nervous system neurons (e.g., cholinergic neurons), sense organ and peripheral neuron supporting cells (e.g., satellite cells), nerve cells and glial cells of the central nervous system (e.g., astroglial cells), chromocytes (e.g., retinal pigment epithelial cells), and progenitor cells thereof (tissue progenitor cells). Without particular limitation concerning the degree of cell differentiation, the age of an animal from which cells are collected, or the like, both undifferentiated progenitor cells (also including somatic stem cells) and terminally-differentiated mature cells can be similarly used as origins for somatic cells in the present invention. Examples of undifferentiated progenitor cells include tissue stem cells (somatic stem cells) such as neural stem cells, hematopoietic stem cells, mesenchymal stem cells, and dental pulp stem cells.

In the present invention, mammals from which somatic cells are collected are not particularly limited and are preferably humans.

(E) Clone embryo-derived ES cells obtained by nuclear transplantation ntES (nuclear transfer ES) cells are clone embryo-derived ES cells prepared by nuclear transplantation techniques, having properties almost the same as those of fertilized egg-derived ES cells (T. Wakayama et al. (2001), Science, 292: 740-743; S. Wakayama et al. (2005), Biol. Reprod., 72: 932-936; J. Byrne et al. (2007), Nature, 450: 497-502). Specifically, ntES cells are the ES cells which are established from the inner cell mass of a blastocyst from a clone embryo that is obtained via substitution of the nucleus of an unfertilized egg with the nucleus of a somatic cell. For preparation of ntES cells, nuclear transplantation techniques (J. B. Cibelli et al. (1998), Nature Biotechnol., 16: 642-646) and the above ES cell preparation techniques are used in combination (Kiyoka Wakayama et al., (2008), Experimental Medicine, Vol. 26, No. 5 (Extra Number), pp. 47-52). Upon nuclear transplantation, the nucleus of a somatic cell is injected into a mammalian enucleated unfertilized egg and then the resultant is cultured for several hours, so that reprogramming can be carried out.

(F) Fusion Stem Cells

Fusion stem cells are prepared by fusing somatic cells to ova or ES cells, so that they have pluripotency similar to that of the ES cells to be fused. Moreover, fusion stem cells also have a gene peculiar to somatic cells (Tada M et al. Curr Biol. 11: 1553-8, 2001; Cowan CA et al. Science. 2005 Aug 26; 309 (5739): 1369-73).

<Method for Inducing Differentiation into Skeletal Muscle or Skeletal Muscle Progenitor Cells>

According to the present invention, the method comprising the following steps can be used for artificially inducing the differentiation of pluripotent cells such as ES cells or iPS cells into skeletal muscle or skeletal muscle progenitor cells;
(1) culturing human pluripotent stem cells by suspension culture,
(2) culturing a cell population after suspension culture by adhesion culture,
(3) dissociating cells after adhesion culture; and
(4) culturing dissociated cells by adhesion culture.

The term "skeletal muscle" as used herein refers to mature muscle including muscle fiber; that is, muscle cells that are multinuclear cells. Also, the term "skeletal muscle progenitor cells" refers to cells that can selectively differentiate into muscle cells, but this does not mean that such cells completely lack differentiation potency into other mesodermal cells such as osteoblasts or fat cells. In the present invention, skeletal muscle progenitor cells include skeletal muscle stem cells (and, possibly, satellite cells).

In the present invention, artificial skeletal muscle or skeletal muscle progenitor cells obtained via induced differentiation may be provided as a cell population containing other cell species or as a purified cell population. Artificial skeletal muscle or skeletal muscle progenitor cells can be identified by detecting the expression of marker genes for skeletal muscle progenitor cells and skeletal muscle, such as MyoD, Myf5, Pax7, myogenin, myosin heavy chain, NCAM, desmin, SkMAct, MF20, M-cadherin, Fgfr4, and VCAME1. In addition to this method, artificial skeletal muscle or skeletal muscle progenitor cells can also be identified using the formation of myotube cells having contractile capacity (e.g., expression of an MRF4 gene) or the like as an index. Here the term "artificial" is used for skeletal muscle or skeletal muscle progenitor cells resulting from in vitro induction of differentiation of human pluripotent cells. Artificial skeletal muscle or skeletal muscle progenitor cells may have properties not identical to, but significantly analogous to those of skeletal muscle or skeletal muscle progenitor cells naturally generated in humans. Artificial skeletal muscle or skeletal muscle progenitor cells that are biocompatible when transplanted in vivo and are capable of compensating and functioning as an alternative for a site of damage are particularly desirable.

(A) Step of Culturing Human Pluripotent Stem Cells by Suspension Culture

In this step, human pluripotent cells obtained as described above are dissociated each other cell or obtained in colony form by an arbitrary method and then suspension culture is carried out. In the preferable invention, colony form of pluripotent stem cells are directly used for suspension culture. In a method for dissociation, cells may be mechanically dissociated or dissociated using a dissociation solution having protease activity and collagenase activity (e.g., Accutase (TM) and Accumax (TM)). Preferably, such a method involves mechanically removing colonies formed under conditions in which cells are cultured while maintaining pluripotency and then subjecting the removed cells directly to suspension culture. Here, colonies to be preferably used herein are cultured for at least 3 days and preferably 5 days before removal.

Here the term "suspension culture" refers to the culture of cells not adhering to a culture dish. Suspension culture can be carried out using a culture dish that has not been artificially treated (e.g., via coating treatment using an extracellular matrix, or the like) in order to improve its properties of adhering to cells or treated (e.g., via coating treatment using polyhydroxyethyl methacrylate (poly-HEMA)) to artificially suppress adhesion. However, the examples are not limited to them.

A medium for suspension culture can be prepared using a medium to be used for culturing animal cells, as a basal medium. Examples of a basal medium include IMDM, a Medium 199 medium, Eagle's Minimum Essential Medium (EMEM), aMEM, Doulbecco's modified Eagle's Medium (DMEM), Ham's F12 medium, an RPMI 1640 medium, Fischer's medium, and mixtures thereof. Preferably, such a mixture is prepared by mixing DMEM and F12 at 1:1. A medium may contain serum or may be serum free. If necessary, for example, a medium may contain one or more serum substitutes, such as albumin, transferrin, Knockout Serum Replacement (KSR) (serum substitute for FBS upon culture of ES cells), an N2 supplement (Invitrogen), a B27 supplement (Invitrogen), fatty acid, insulin, a collagen progenitor, a trace element, 2-mercaptoethanol, 3'-thiolglycerol, as well as one or more substances such as lipids, amino acid, nonessential amino acid, a vitamin, a growth factor, a cytokine, an antibiotic, an antioxidant, pyruvic acid, a buffering agent, and inorganic salts.

An example of such a medium is DMEM/Ham's F12 (mixture) medium containing 20% knockout serum replacement (KSR), 2 mM L-glutamine, and nonessential amino acids.

The temperature for culture ranges from about 30° C. to 40° C. and is preferably about 37° C., but the examples are not limited thereto. Culture is carried out under an atmosphere containing $CO_2$. $CO_2$ concentration preferably ranges from about 2% to 5%. The time for culture ranges from 5 to 9 days, for example, and is more preferably 7 days. Medium exchange is preferably carried out every 2 to 5 days.

(B) Step of Culturing Cell Population by Adhesion Culture

In this step, the cell population after suspension culture, which is obtained in the previous step, is directly cultured in an arbitrary medium using a coated culture dish. Examples of a coating agent include collagen, gelatin, laminin, heparan sulfate proteoglycan, and entactin, or combinations thereof. A preferable example of a coating agent is gelatin.

A medium to be used in this step can be prepared using a medium to be used for culturing animal cells as a basal medium. Examples of a basal medium include IMDM, a Medium 199 medium, Eagle's Minimum Essential Medium (EMEM), aMEM, Doulbecco's modified Eagle's Medium (DMEM), Ham's F12 medium, an RPMI 1640 medium, Fischer's medium, and mixtures thereof. Preferably, such a basal medium is DMEM. A medium desirably contains no serum. If necessary, a medium may contain one or more serum substitutes such as albumin, insulin, transferrin, sodium selenite, ITS-X (Gibco) (containing insulin, transferrin, and sodium selenite), Knockout Serum Replacement (KSR) (serum substitute for FBS upon culture of ES cells), an N2 supplement (Invitrogen), a B27 supplement (Invitrogen), fatty acid, a collagen progenitor, a trace element, 2-mercaptoethanol, and 3'-thiolglycerol, as well as one or more substances such as lipids, amino acid, Glutamax (Gibco), nonessential amino acid, a vitamin, a growth factor, a cytokine, an antibiotic, an antioxidant, pyruvic acid, a buffering agent, and inorganic salts.

An example of a preferable medium contains insulin, transferrin, and sodium selenite, in addition to glutamine and 2-mercaptoethanol.

The temperature for culture ranges from about 30° C. to 40° C. and is preferably about 37° C., but the examples are not limited thereto. Culture is carried out under an atmosphere containing $CO_2$. $CO_2$ concentration preferably ranges from about 2% to 5%. The time for culture ranges from 7 to 21 days, for example, and is more preferably 14 days. Medium exchange is desirably carried out every 2 to 5 days.

(C) Step of Dissociating Cells and Culturing Cells by Adhesion Culture Again

In this step, the cell population after adhesion culture (obtained in the previous step) is dissociated and then cultured in an arbitrary medium using a culture dish coated at a low initial cell density. Examples of a coating agent include collagen, gelatin, laminin, heparan sulfate proteoglycan or entactin, and combinations thereof. In this step, a preferable coating agent is type I collagen.

As a method for dissociating a cell population, mechanical dissociation or a method using a dissociation solution having Trypsin/EDTA or protease activity and collagenase activity (e.g., Accutase (Trademark) and Accumax (Trademark)) may be used.

A medium to be used in this step can be prepared using a medium to be used for culturing animal cells as a basal medium. Examples of a basal medium include IMDM, a Medium 199 medium, Eagle's Minimum Essential Medium (EMEM), aMEM, Doulbecco's modified Eagle's Medium (DMEM), Ham's F12 medium, an RPMI 1640 medium, Fischer's medium, and mixtures thereof. Preferably, such a medium is DMEM. A medium may contain serum. Examples of serum include, but are not particularly limited to, human serum, monkey serum, fetal calf serum, bovine serum, swine serum, horse serum, donkey serum, chicken serum, quail serum, sheep serum, goat serum, dog serum, cat serum, rabbit serum, rat serum, guinea pig serum, and mouse serum. If necessary, a medium may contain one or more serum substitutes such as albumin, insulin, transferrin, sodium selenite, ITS-X (Gibco), Knockout Serum Replacement (KSR) (serum substitute for FBS upon culture of ES cells), an N2 supplement (Invitrogen), a B27 supplement (Invitrogen), fatty acid, a collagen progenitor, a trace element, 2-mercaptoethanol, and 3'-thiolglycerol, as well as one or more substances such as lipids, amino acid, Glutamax (Gibco), nonessential amino acid, a vitamin, a growth factor, a cytokine, an antibiotic, an antioxidant, pyruvic acid, a buffering agent, and inorganic salts.

An example of a preferable medium contains fetal calf serum and horse serum, in addition to nonessential amino acid, glutamine, and 2-mercaptoethanol.

Also, a low cell density ranges from about 1,000 to 3,000 cells/cm$^2$, for example.

The temperature for culture ranges from about 30° C. to 40° C. and is preferably about 37° C., but the examples are not limited thereto. Culture is carried out under an atmosphere containing $CO_2$. $CO_2$ concentration preferably ranges from about 2% to 5%. The time for culture ranges from 21 to 35 days, for example, and is more preferably 28 days. Medium exchange is desirably carried out every 2 to 5 days.

In this step, adhesion culture may further be carried out for 14 to 21 days, after medium exchange with a serum free medium. Such a medium to be used herein preferably contains insulin, transferrin, and sodium selenite, in addition to glutamine and 2-mercaptoethanol.

<Kit for Induction of Differentiation into Skeletal Muscle or Skeletal Muscle Progenitor Cells>

The present invention provides a kit for inducing the differentiation of pluripotent stem cells into skeletal muscle or skeletal muscle progenitor cells. This kit may contain the above medium to be used for induction of differentiation, a dissociation solution (e.g., Trypsin/EDTA or buffer having protease activity and collagenase activity), a coating agent for coating a culture dish (e.g., collagen, gelatin, laminin, heparan sulfate proteoglycan or entactin, or combinations thereof), and the like. This kit may further contain written procedures or instructions for induction of differentiation.

<Skeletal Muscle or Skeletal Muscle Progenitor Cells>

The present invention provides artificial skeletal muscle or skeletal muscle progenitor cells prepared by the method for induction of differentiation as described above.

Artificial skeletal muscle or skeletal muscle progenitor cells can be identified using markers for skeletal muscle progenitor cells and skeletal muscle, such as MyoD, Myf5, Pax7, myogenin, myosin heavy chain, NCAM, Desmin, SkMAct, MF20, M-Cadherin, Fgfr4, and VCAME1.

Skeletal muscle or skeletal muscle progenitor cells may be directly transplanted into a living body after preparation. Preferably, skeletal muscle progenitor cells may be transplanted into a living body. At this time, skeletal muscle cells or skeletal muscle progenitor cells can be purified and separated by a conventional technique such as a flow cytometry method using a fluorescence-labeled specific antibody as described below.

<Application to Screening for Agents for Treating Myogenic Diseases>

The skeletal muscle or the skeletal muscle progenitor cells of the present invention can also be used for screening for compounds (e.g., pharmaceutical compounds, solvents, small molecules, peptides, or polynucleotides) for treating myogenic diseases (e.g., muscular dystrophy and myopathies). For example, a candidate pharmaceutical compound alone or a combination of a candidate pharmaceutical compound and another medical agent is added to the above-induced skeletal muscle or skeletal muscle progenitor cells, so that evaluation can be made based on a change in number of the cells. Here, skeletal muscle or skeletal muscle progenitor cells are preferably cells that present a phenotype similar to that of a myogenic disease to be treated. Particularly preferable skeletal muscle or skeletal muscle progenitor cells are cells obtained by inducing the differentiation of iPS cells prepared from somatic cells from a patient affected with a given disease or ntES cells into which the nuclei of somatic cells from a patient with such a disease have been transplanted.

<Use for Regenerative Medicine>

The artificial skeletal muscle or skeletal muscle progenitor cells of the present invention can be effectively used in the field of regenerative medicine in order to normalize damaged skeletal muscle tissue. Therefore, the cells can be used for treating myogenic diseases.

Examples of myogenic diseases include muscular dystrophy (Duchenne, Becker, congenital, and limb-girdle muscular dystrophy), congenital myopathies, mitochondrial diseases, glycogenosis, myasthenia gravis, and myasthenic syndrome.

Also, when the cells are used as therapeutic medicaments or composition, cell purity is desirably increased. An example of such a method for increasing cell purity is a method for sorting a target cell such as a flow cytometry method. A flow cytometry method involves causing cell particles to flow through the very thin stream of a solution at a high rate, irradiating the same with a laser beam, and then measuring light such as fluorescence emitted from the particles (when the cells are fluorescence-labeled in advance) or scattered light. A cell sorter is provided so as to make it possible to sort and separate a target cell. Fluorescence labeling of cells can be carried out using an antibody (fluorescence-labeled) specific to the skeletal muscle or skeletal muscle progenitor cells, such as an SM/C-2.6 antibody (Fukada S, et al, Exp Cell Res. 296: 245-55, 2004), an anti-M-cadherin antibody, an anti-FGFR4 antibody, an anti-NCAM antibody, and an anti-VCAM1 antibody.

Such cells to be used for regenerative medicine may be patient-derived ES cells, patient-derived iPS cells, or ntES cells prepared using patient-derived nuclei or pluripotent stem cells from others having the same or substantially the same type of HLA. When patient-derived pluripotent stem cells are used for treating a myogenic disease such as muscular dystrophy, a normal disease-related gene such as normal human dystrophin-coding DNA (including a gene, genomic DNA, cDNA, and the like) (e.g., GenBank Accession No. BC150141(SEQ ID NO: 21)) is directly or indirectly introduced into the thus established ES cells, ntES cells, or iPS cells, and then the differentiation of the cells into target skeletal muscle or skeletal muscle progenitor cells can be induced using the method of the present invention. The full-length of a dystrophin gene is 14 kb and the introduction of the gene with the use of a vector such as an artificial chromosome (preferably, the human chromosome (Republication 2008/013067)) is exemplified. In addition to such a method, a method that involves introducing a shortened functional dystrophin gene using an adeno-associated virus vector, a method that involves introducing a mini-dystrophin gene using a retrovirus vector, a Sendai virus vector, or a lentivirus vector, and the like are exemplified.

Techniques described herein for illustrative purposes can be carried out by known methods. ES cells or ntES cells can be directly transformed or transfected with a vector containing DNA encoding normal human dystrophin. Meanwhile, iPS cells can be directly transformed or transfected using such a vector, or iPS cells may be induced after transformation or transfection of somatic cells with such a vector in advance for induction of iPS cells. Transformation or transfection and other general techniques (e.g., gene recombination techniques and PCR amplification techniques) are described in academic documents, patent documents, academic books (Sambrook et al., Molecular Cloning A Laboratory Manual; Ausubel et al., Current Protocols in Molecular Biology), and the like, and thus the disclosures therein can be referred to.

EXAMPLES

The present invention will be further described in detail by examples as follows, but the scope of the present invention is not limited by these examples. ES cells Human ES cells (KhES-1) received from the Institute for Frontier Medical Sciences, Kyoto University (Kyoto, Japan) were cultured by a conventional method (Suemori H, et al. Biochem Biophys Res Commun. 345: 926-32, 2006). Human iPS cells (253G4) received from prof. Yamanaka were cultured by a conventional method (Nakagawa M, et al. Nat Biotechnol. 26: 101-6, 2008).

Induction of differentiation (with feeder cells) into skeletal muscle or skeletal muscle progenitor cells Human ES cells were cultured for 5 days using STO cells as feeder cells, removed in the form of colonies using a dissociation solution for human ES cells [containing Trypsin, 10 mg/ml Collagenase IV, KSR (Invitrogen), 1 M $CaCl_2$/PBS, and PBS], and then subjected to 7 days of suspension culture (embryoid body formation) in a human embryonic stem cell maintenance medium [DMEM/F12 (Sigma)+20% KSR+1% NEAA+2 mM L-glutamine] in a Petri dish. Adhesion culture was then carried out for 14 days in a serum free medium (DMEM+1×ITS-X (Gibco)+1×Glutamax (Gibco)+100 μM 2-mercaptoethanol) on a 0.1% gelatin-coated cell culture dish. Subsequently, embryoid bodies were dissociated using Trypsin/EDTA and then seeded onto a type I collagen-coated dish (BD Bioscience) at a low density (about 1,000 to 3,000 cells/cm²), followed by 3 to 4 weeks of culture using a serum medium [DMEM+10% FCS (fetal calf serum; Sigma)+5% HS (horse serum; Sigma)+1% NEAA+(1×Glutamax)+100 μM 2-mercaptoethanol]. Induction of differentiation might be discontinued for cell transplantation; however, medium exchange with a serum free medium (DMEM+1×ITS-X+(1× Glutamax)+100 μM 2-mercaptoethanol) was carried out and then cells were further cultured for 2 to 3 weeks. The outline of the above processes is shown in FIG. 1. Medium exchange was carried out every 5 days under all conditions.

Figure 2:
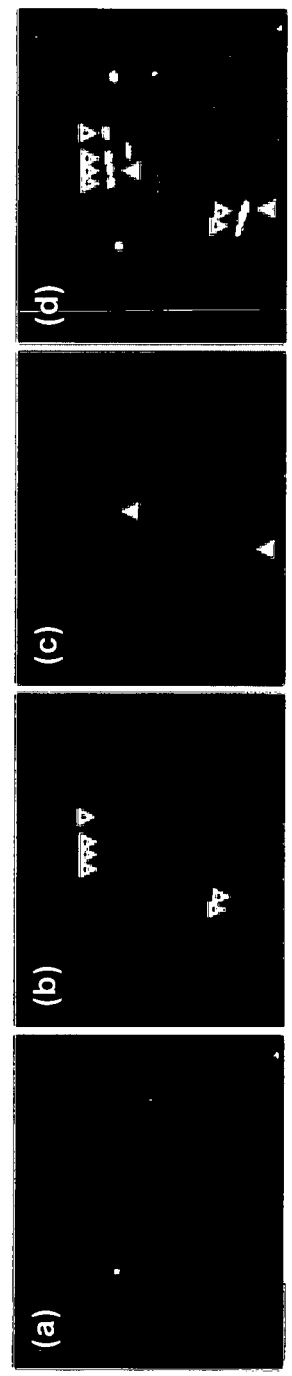
FIG. 2 shows the following immunostaining images of cells on day 70 after induction of differentiation: (a) DAPI (4',6-diamidino-2-phenylindole); (b) myogenin (Clone: F5D); (c) myosin (skeletal muscle); and (d) an image obtained by merging these images.
Figure 3:
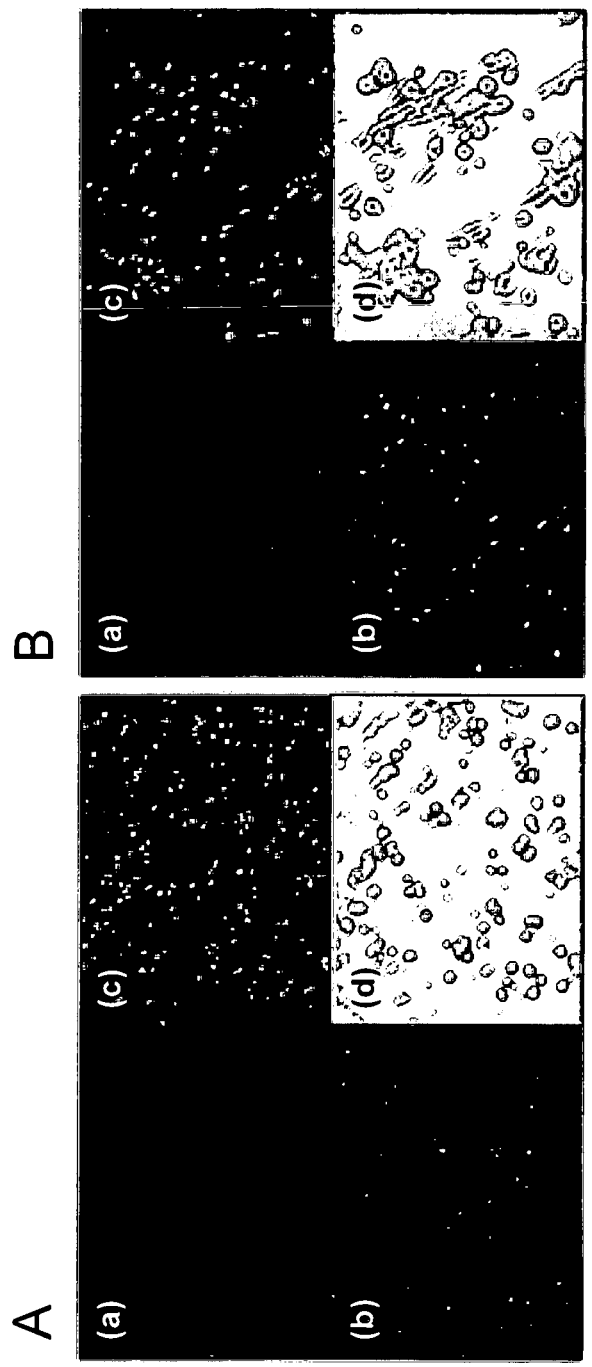
FIG. 3 shows the images of cells on day 70 after induction of differentiation, specifically: an immunostaining images (A) and a phase-contrast images (B) of (a) DAPI (4',6-diamidino-2-phenylindole); (b) myogenin; and (c) myosin (skeletal muscle).

The cells resulting from the induction of differentiation were immunostained using the antibody for a myosin heavy chain II (Sigma, myosin Skeletal M7523) that is a mature skeletal muscle marker, and the antibody for a skeletal muscle transcription factor myogenin (Dako, M3559 (F5D)) thought to be involved in fusion of skeletal muscle cells. Thus, expression of them could be confirmed (FIG. 2 and FIG. 3). Furthermore, spontaneous contractile activity was also observed. As described above, it was demonstrated that preparation of mature skeletal muscle in vitro from human pluripotent cells was successful using the method. At the same time, it was suggested that skeletal muscle progenitor cells had been prepared.

Figure 4:
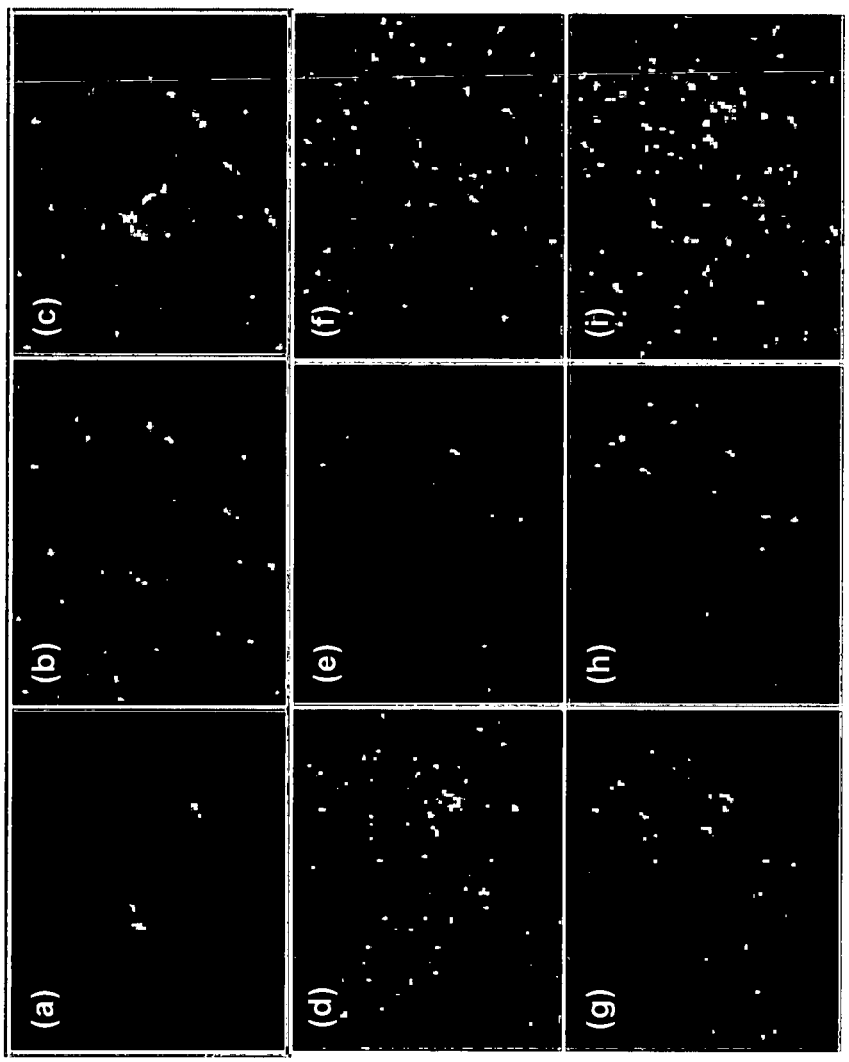
FIG. 4 shows the immunostaining images of muscle tissue on 4 weeks after transplantation of differentiated cells: (a) human Laminin (merosin); (b) murine/human Laminin; (c) merged image of (a) and (b); (d) DAPI (4',6-diamidino-2-phenylindole); (e) human Laminin A/C; (f) murine/human Laminin; (g) merged image of (d) and (e); (h) merged image of (e) and (f); and (i) merged image of (d), (e) and (f).

$5.0 \times 10^5$/20 μL Solution of cells, which were differentiated from human ES cells for 49 days with above method and dissociated with trypsin/EDTA, were directly transplanted into tibialis anterior muscle of skeletal muscle injury model NOG mouse which was treated with Cardiotoxin at 24 hours prior to transplanting and 1.2 Gy total body irradiation. On 4 weeks after transplantation, the engraftment was identified by immunostaining with human specific laminin (merosin) antibody (Novocastra Laboratories) and laminin A/C antibody (Dako) (FIG. 4). Same result could be obtained from the cells differentiated from iPS cells (253G4).

Industrial Applicability

The present invention makes it possible to reduce the frequency of complicated isolation work involving pluripotent stem cells such as ES cells or iPS cells and to prepare skeletal muscle or skeletal muscle progenitor cells. The thus prepared skeletal muscle or skeletal muscle progenitor cells can be used in the field of regenerative medicine for treating myogenic diseases.

All publications, patents, and patent applications cited herein are incorporated herein by reference in their entirety.

The invention claimed is:

1. A method for producing skeletal muscle or skeletal progenitor cells from human pluripotent stem cells comprising:
   a) culturing human pluripotent stem cells in suspension culture such that an embryoid body is formed;
   b) culturing the embryoid body of step (a) on gelatin-coated culture dish in a serum-free medium, wherein the embryoid body adheres to the gelatin-coated culture dish;
   c) dissociating the embryoid body of step (b) such that dissociated cells are obtained; and
   d) culturing the dissociated cells of step (c) on a type I collagen-coated culture dish, wherein the dissociated cells of step (c) adhere to the type I collagen-coated culture dish, and in a differentiation medium comprising serum, thereby producing skeletal muscle or skeletal muscle progenitor cells.

2. The method according to claim 1, wherein the human pluripotent stem cells of step (a) are in the form of pluripotent stem cell colonies produced on an adhesion substrate and the colonies are directly placed into the suspension culture.

3. The method according to claim 1, wherein the serum free medium comprises insulin, transferrin, and sodium selenite.

4. The method according to claim 1, wherein the culturing of the dissociated cells comprises culturing the dissociated cells at an initial density of 1,000-3,000 cells/cm².

5. The method according to claim 1, wherein in step (d) the differentiation medium comprises fetal calf serum and horse serum.

6. The method according to claim 1, wherein the culturing of step (a) occurs for 7 days.

7. The method according to claim 1, wherein the culturing of (b) occurs for 14 days.

8. The method according to claim 1, wherein the culturing step of (d) occurs for at least 21 days.

9. The method according to claim 5, wherein in step (d) further comprises exchanging the differentiation medium with a serum-free medium comprising insulin, transferrin and selenite and further culturing the dissociated cells.

10. The method according to claim 1, wherein the human pluripotent stem cells are human embryonic stem cells or human induced pluripotent stem cells.

11. The method according to claim 2, wherein the serum-free medium of step (b) comprises insulin, transferrin and selenite.

12. The method according to claim 2, wherein the culturing of the dissociated cells comprises culturing the dissociated cells at an initial density of 1,000-3,000 cells/cm².

13. The method according to claim 9, wherein the dissociated cells in step (d) are cultured in the differentiation medium for 28 days and then further cultured in the serum free differentiation medium for 21 days.

* * * * *